US011155550B2

(12) United States Patent
Ma et al.

(10) Patent No.: US 11,155,550 B2
(45) Date of Patent: Oct. 26, 2021

(54) HISTONE DEACETYLASE INHIBITORS AND METHODS OF USE THEREOF

(71) Applicant: Reaction Biology Corp., Malvern, PA (US)

(72) Inventors: Haiching Ma, Malvern, PA (US); Yangbo Feng, Malvern, PA (US); Yuren Wang, Washington Crossing, PA (US)

(73) Assignee: Reaction Biology Corporation, Malvern, PA (US)

( * ) Notice: Subject to any disclaimer, the term of this patent is extended or adjusted under 35 U.S.C. 154(b) by 0 days.

(21) Appl. No.: 16/290,174

(22) Filed: Mar. 1, 2019

(65) Prior Publication Data

US 2019/0270744 A1 Sep. 5, 2019

Related U.S. Application Data

(60) Provisional application No. 62/636,966, filed on Mar. 1, 2018, provisional application No. 62/721,764, filed on Aug. 23, 2018.

(51) Int. Cl.
C07D 471/10 (2006.01)
C07D 491/107 (2006.01)
C07D 491/113 (2006.01)
C07D 498/10 (2006.01)

(52) U.S. Cl.
CPC ....... *C07D 471/10* (2013.01); *C07D 491/107* (2013.01); *C07D 491/113* (2013.01); *C07D 498/10* (2013.01)

(58) Field of Classification Search
CPC .................................................. C07D 471/10
See application file for complete search history.

(56) References Cited

U.S. PATENT DOCUMENTS

| 8,883,816 B2 | 11/2014 | Tafesse |
| 2009/0124578 A1 | 5/2009 | Egle |
| 2017/0044185 A1 | 2/2017 | Ma |

FOREIGN PATENT DOCUMENTS

| WO | 2011142359 | 11/2011 | |
| WO | WO-2011142359 A1 * | 11/2011 | .............. A61P 43/00 |
| WO | 2017004266 | 1/2017 | |

OTHER PUBLICATIONS

SHEN, Dong-Ming, et al. "Discovery of novel, potent, and orally active spiro-urea human glucagon receptor antagonists." Bioorganic & Medicinal Chemistry Letters. (2005), vol. 15, pp. 4564-4569. (Year: 2005).*
Yang, Young-Keun, et al. "Synthesis of a highly metal-selective rhodamine-based probe and its use for the in vivo monitoring of mercury." Nature Protocols. (2007), vol. 2, No. 7, pp. 1740-1745. (Year: 2007).*
Jin, Kang, et al. "Novel indoline-2,3-dione derivatives as inhibitors of aminopeptidase N (APN)." Bioorganic & Medicinal Chemistry Letters. (2013), vol. 21, pp. 2663-2670. (Year: 2013).*
Akhtar, M. W. et al., "Histone Deacetylases 1 and 2 Form a Developmental Switch That Controls Excitatory Synapse Maturation and Function", J. Neurosci., 2009, 29:8288-8297.
All India Institute of Medical Sciences, New Delhi, "Valproate and Levocarnitine in Children wiht Spinal Muscular Atrophy", 2015, ClinicalTrials.gov, 1-3. <https://clinicaltrials.gov/beta/show/NCT01671384?term=nct01671384&>.
Bahari-Javan et al., "HDAC1 links early life stress to schizophrenia-like phenotypes", Proc. Natl. Acad. Sci., 2017, 114: E4686-E4694.
Bayside Health et al., "Safety and Effect on HIV Transcription of Vorinostat in Patients Receiving Suppressive Comination Anti-retroviral Therapy", 2017, ClinicalTrials.gov, 1-3.<https://clinicaltrials.gov/beta/show/NCT01365065?term=nct01365065&>.
Blackwell et al., "The use of diversity profiling to characterize chemical modulators of the histone deacetylases", Life Science, 2008, 82:1050-1058.
Bots et al., "Rational combinations using HDAC inhibitors", Clin. Cancer Res., 2009, 15:3970-3977.
Carmi et al., "Novel Irreversible Epidermal Growth Factor Receptor Inhibitors by Chemical Modulation of the Cysteine-Trap Portion", J. Med. Chem., 2010, 53:2038-2050.
Chen, L., "Medicinal Chemistry of Sirtuin Inhibitors", Curr. Med. Chem., 2011, 18:1936-46.
Falkenberg et al., "Histone deacetylases and their inhibitors in cancer, neurological diseases and immune disorders", Nat. Rev. Drug Discov., 2014, 13:673-691.
Fudras et al. "Synthesis of isothizol-3-one derivatives as inhibitors of histone actetyltransferases (HATs)", Bioorg. Med. Chem., 2009, 17:467-474.
Furdas et al. "Pyrido- and benzisothiazolones as inhibitors of histone acetyltransferases (HATs)", Med. Chem. Commun., 2014, 5:1856-1862.
Gallinari et al., "HDACs, histone deacetylation and gene transcription: from molecular biology to cancer therapeutics", Cell Res., 2007, 17:191-211.
Giannini et al., "Histone deacetylase inhibitors in the treatment of cancer: overview and perspectives", Future Med. Chem., 2012, 4:1439-1460.
Graff, J. et al., "An epigenetic blockade of cognitive functions in the neurodegenerating brain", Nature, 2012, 483:222-226.
Graff, J. et al., "Epigenetic Priming of Memory Updating During Reconsolidation to Attenuate Remote Fear Memories", Cell, 2014, 156:261-276.

(Continued)

Primary Examiner — John S Kenyon
(74) Attorney, Agent, or Firm — Riverside Law LLP

(57) ABSTRACT

The present invention relates to methods of modulating activity of histone deacetylases (HDACs). The present invention also relates to methods of treating HDAC-associated diseases including, but not limited to, cancers, inflammatory disorders, and neurodegenerative disorders. The present invention also provides novel compounds and compositions thereof and methods of preparation of the same. The present invention also includes methods of inhibiting HDACs, and methods of treating HDAC-associated diseases using the compounds of the invention.

7 Claims, 3 Drawing Sheets

(56) References Cited

OTHER PUBLICATIONS

Gregoretti et al., "Molecular Evolution of the Histone Deacetylase Family: Functional Implications of Phylogenetic Analysis", 2004, J. Mol. Biol. 338:17-31.
Grozinger et al., "Deacetylase enzymes: biological functions and the use of small-molecule inhibitors", Chem. Biol., 2002, 9:3-16.
Guan, J. S. et al., "HDAC2 negatively regultes memory formation and synaptic plasticity", Nature, 2009, 459:55-60.
H. Lee Moffitt Cancer Center and Research Institute et al. "Phase I of Histone Deacetylase HDAC) Inhibitor Panobinostat with Ipilimumab with Unresectable III/IV Melanoma", 2017, ClinicalTrials.gov, 1-3. <https://clinicaltrials.gov/beta/show/NCT02032810?term=nct02032810&>.
Hu et al., "Identification of novel isoform-selective inhibitors within class I histone deacetylases", J. Pharmacol. Ther., 2003, 307:720-728.
Kazantsev et al., "Therapeutic application of histone deacetylase inhibitors for central nervous system disorders", Nat. Rev. Drug Discov., 2008, 7:854-868.
Kim et al., "Quantitative Determination of Tumor Blood Flow and Perfusion Via Deuterium Nuclear Magnetic Resonance Spectroscopy in Mice", Cancer Research, 1988, 48:3449-3453.
McQuown, S. C. et al., "Epigenetic Regulation in Substance Use Disorders", Curr. Psychiatr. Rep., 2010, 12:145-153.
Morris, M. J. et al, "Loss of histone deacetylase 2 improves working memory and accelerates extinction learning", J. Neurosci., 2013, 33:6401-6411.
Mottamal et al., "Histone deacetylase inhibitors in clinical studies as templates for new anticancer agents", Molecules, 2015, 20:3898-3941.
Nakagawa et al., "Expression profile of class I histone deacetylases in human cancer tissues", Oncol. Rep., 2007, 18:769-774.
Oehme et al., "Histone deacetylase 8 in neuroblastoma tumorigenesis", Clin. Cancer Res., 2009, 15:91-99.
Parmigiani et al., "HDAC6 is a specific deacetylase of peroxiredoxins and is involved in redox regulation", Proc. Natl. Acad. Sci., 2008, 105:9633-9638.
Santo, L. et al., "Preclinical activity, pharmacodynamic, and pharmacokinetic properties of a selective HDAC6 inhibitor, ACY-1215, in combination with bortezomib in multiple myeloma", Blood, 2012, 119:2579-2589.
Shankar, S. et al., (2008) Histone Deacetylase Inhibitors: Mechanisms and Clinical Significance in Cancer: HDAC Inhibitor-Induced Apoptosis. In: Programmed Cell Death in Cancer Progression and Therapy. Advances in Experimental Medicine and Biology, vol. 615. Springer, Dordrecht, p. 261-298.
Thurn et al., "Rational therapeutic combinations with histone deacetylase inhibitors for the treatment of cancer", Future Oncol., 2011, 7:263-283.
Tsai et al., "Resveratrol reverses morphine-induced neuroinflammation in morphine-tolerant rats by reversal HDAC1 expression", Journal of the Formosan Medical Association, 2016, 115:445-454.
University of Aarhus et al., "Safety and Effect of the HDAC Inhibitor Panobinostat on HIV-1 Expression in Patients on Suppressive HART (CLEAR)", 2014, ClinicalTrials.gov, 1-3. <https://clinicaltrials.gov/beta/show/NCT01680094?term=nct01680094&>.
University of North Carolina, Chapel Hill et al., "The Effect of Vorinostat on HIV RNA Expression in the REsting CD4+ T Cells of HIV+ Pts on Stable ART", 2016, ClinicalTrials.gov, 1-3. <https://clinicaltrials.gov/beta/show/NCT01319383?term=nct01319383&>.
Valente et al., "Small-molecule inhibitors of histone deacetylase for the treatment of cancer and non-cancer diseases: a patent review (2011-2013)", Expert Opin. Ther. Patents, 2014, 24:1-15.
Villalba et al., "Sirtuin activators and inhibitors", Biofactors, 2012, 38:349-359.
Weber, D. M. et al., "Phase I trial of vorinostat combined with bortezomib for the treatment of relapsing and/or refractory multiple myeloma", Clin. Lymphoma Myeloma Leuk., 2012, 12:319-324.
Weïwer et al., "Therapeutic potential of isoform selective HDAC inhibitors for the treatment of schizophrenia", Future Med. Chem., 2013, 5:1491-1508.
Wright et al., "Metabolism Resistant Isothizolone Inhibitors of Cartilage Breakdown", Bioorg. Med. Chem., 1995, 3:227-234.
Yamakawa et al., "The transcription factor Sp3 cooperates with HDAC2 to regulate synaptic function and plasticity in neurons", Cell Reports, 2017, 20:1319-1334.
Yang et al., "The development prospection of HDAC inhibitors as a potential therapeutic direction in Alzheimer's disease", Transl. Neurodegener., 2017, 10:6-19.

\* cited by examiner

HISTONE DEACETYLASE INHIBITORS AND METHODS OF USE THEREOF

CROSS-REFERENCE TO RELATED APPLICATIONS

The present application claims priority to U.S. Provisional Application Ser. Nos. 62/636,966, filed on Mar. 1, 2018 and 62/721,764, filed on Aug. 23, 2018 which are incorporated by reference herein in their entireties.

FIELD

Described herein are compounds as isoform selective histone deacetylase inhibitors, their derivatives, analogs, tautomeric forms, isotope forms, stereoisomers, geometrical isomers, diastereomers, polymorphs, hydrates, solvates, pharmaceutical acceptable salts, metabolites, intermediates and prodrugs thereof, the preparation of these compounds, the pharmaceutical compositions comprising these compounds and the use of these compounds for treating various diseases.

BACKGROUND OF THE INVENTION

Histone deacetylases (HDACs) have emerged as pharmaceutical targets with a broad range of potential indications. Several pan-HDAC inhibitors (not paralogue selective) of different chemotypes, which target several of the 11 paralogues of Zn-dependent HDACs and span different chemotypes, are approved by the FDA or are currently in clinical trials. However, these nonselective agents typically lead to undesired side effects, and considerable efforts are still spent toward the development of more selective chemical probes and drug candidates.

Histone deacetylase proteins are a family of enzymes that control the acetylation state of protein lysine residues, notably lysine residues contained in the N-terminal extensions of core histones. The acetylation state of histones affects gene expression by influencing chromatin conformation. In addition, the stability or biological function of several non-histone proteins is regulated by the acetylation state of specific lysine residues (Gallinari et al., 2007, Cell Res. 17:191-211; Kazantsev and Thompson, 2008, Nat Rev Drug Discov. 7:854-868).

In humans, HDAC proteins comprise a family of 18 members, which are separated into four classes based on size, cellular localization, number of catalytic active sites, and homology to yeast HDAC proteins. Class I includes HDAC1, HDAC2, HDAC3, and HDAC8. Class I HDACs are ubiquitously expressed, largely restricted to the nucleus and in the case of HDACs 1, 2 and 3, known to deacetylate histones. They share a highly conserved and homologous N-terminal catalytic domain. Class II consists of six HDAC proteins that are further divided into two subclasses. Class IIa includes HDAC4, HDAC5, HDAC7, and HDAC9, which each contain a single catalytic active site. Class IIa HDACs display more tissue specific distribution and can translocate between the nucleus and cytoplasm. These enzymes display weak inherent catalytic activity and require higher order protein complexes, often containing HDAC3, to become catalytically competent deacetylases. Class IIb includes HDAC6 and HDAC10, which each contain two active sites, although only HDAC6 has two catalytically competent active sites. The Class IIb HDACs include HDACs 6 and 10 with HDAC6 being predominantly localized to the cytoplasm while little is known about the localization of HDAC10. The Class IIb HDACs uniquely contain two independently active and substrate specific catalytic domains and it is the N-terminal domain of HDAC6 that is responsible for the deacetylation of α-tubulin.

The Class IV HDAC is composed of a single enzyme, HDAC11, with little known about its function; however, it has been detected across a broad range of tissue types including heart, muscle, kidney and testes. HDAC11 is the sole member of class IV, based on phylogenetic analysis. Class I, II, and IV HDAC proteins operate by a metal ion-dependent mechanism, as indicated by crystallographic analysis. In contrast, class III HDAC proteins, referred to as sirtuins (i.e., SIRT1 through SIRT7), operate by a NAD$^+$-dependent mechanism unrelated to the other HDAC proteins (Gregoretti et al., 2004, J Mol Biol. 338:17-31; Grozinger and Schreiber, 2002, Chem Biol. 9:3-16).

Small molecules have been developed with varied inhibitory profiles from several chemical classes including alkanoic acids (sodium butyrate [NaB]), hydroxamic acids (SAHA) and ortho-aminoanilides (MS-275). These compounds are well established inhibitors of primarily the Class I HDACs, and have served as the pharmacological workhorses in clinical, (SAHA [Vorinostat™], MS-275 [Entinostat™] and valproate [Depakote™]) and preclinical studies (vide infra). The majority of inhibitors are nonselective and inhibit multiple isoforms both within and across classes. Although the alkanoic acids (NaB, phenyl butyrate and valproate) have been used extensively as HDAC inhibitors, these compounds display weak inhibitory activity of the Class I HDACs. On the contrary, hydroxamic acids and ortho-aminoanilides are potent inhibitors, and depending on substitution patterns, display Class I and II or sub-Class I selectivity, respectively.

The overexpression of different isoforms of HDACs has been found in several types of cancers, as well as in neurological and inflammatory pathologies. The use of HDAC inhibitors represents a treatment for such diseases (Valente and Mai, 2014, Expert Opin. Ther. Patents, 24:1-15; Falkenberg and Johnstone, 2014, Nat Rev Drug Discov. 13:673-91). The following are examples of HDAC inhibitors that have been tested in clinical trials both as single agents and in combination with chemotherapies and other targeted therapeutics: ACY1215 (Acetylon), CG200745 (Crystal Genomics), 4SC-202 (4SC corporation), CHR-2845 (Chroma Therapeutics), AR-42 (Arno Therapeutics), CUDC-101 (Curis Inc), Givinostat (Italfarmaco), Resminostat (4SC-Corporation), Pracinostat (S*BIO Pte Ltd), Etinostat (Syndax), Abexinostat (Pharmacyclics), Mocetinostat (Methylgene), Belinostat (TopoTarget), Valproic Acid (Instituto Nacional de Cancerologia), Panobinostat (Novartis), Vorinostat (Merck), and Romidepsin (Celgene).

HDAC inhibitors have been combined with a broad range of agents (Bots, & Johnstone, 2009. Clin. Cancer Res. 15, 3970-3977; Mottamal et al, 2015, Molecules, 20, 3898-3941). The following are examples of drugs and treatment that have been tested in combination with HDAC inhibitors: 5-fluorouracil, Bortezomib, Carboplatin, Paclitaxel, Cisplatin, Cyclophosphamide, Doxorubicin, Hydroxycarbamide, Hydroxychloroquine, Leucovorin, Marizomib, Pazopanib, Sorafenib, Temozolomide, and radiation etc. The most prominent example of the empirical testing of HDAC inhibitors in combination is with DNA-damaging chemotherapeutics, which have led to many successful outcomes (Thurn, et al, 2011, Future Oncol. 7, 263-283). HDAC inhibitors have also been successfully combined with DNMT inhibitors. Two Phase I trials have been carried out with vorinostat and bortezomib for the treatment of relapsing and/or refractory multiple myeloma with overall positive responses (Weber D M, Graef T et al 2012, Clin. Lymphoma Myeloma Leuk. 12, 319-324). A Phase III trial is currently assessing VPA (Valproic acid) in combination with levocarnitine in children with spinal muscular atrophy (ClinicalTrials.gov identifier: NCT01671384): Vorinostat, panobinostat and VPA are currently being tested in combination with various antiretroviral therapies (ClinicalTrials.gov identifiers: NCT01680094, NCT01319383 and NCT01365065). A Phase I study combining Panobinostat with Ipilimumab to treat unresectable III/IV melanoma has just started (ClinicalTrials.gov identifiers: NCT02032810). HDAC6-specific inhibitors, rocilinostat (ACY-1215), is being tested clinically for the treatment of multiple myeloma in combination with bortezomib, following promising preclinical results (Santo L, Hideshima T, et al, 2012, Blood; 119: 2579-2589.).

Many of the earlier HDAC inhibitors tested in clinical trials are either pan-inhibitors or have poor isoform selectivity. Thus, there is an interest in identifying HDAC inhibitors exhibiting selectivity within or between the human HDAC isoform classes. Achieving selectivity would not only reduce side effects, but would also provide the ability to target distinct therapeutic areas (Hu et al., 2003, J Pharmacol. Ther. 307: 720-728; Giannini et al., 2012, Future Med Chem. 4:1439-1460; Weïwer et al., 2013, Future Med Chem. 5:1491-1508; Falkenberg and Johnstone, 2014, Nat Rev Drug Discov. 13:673-91).

HDAC6 is a well-characterized class IIb deacetylase that regulates many important biological processes via the formation of complexes with its partner proteins. HDAC6 possesses two catalytic domains and a C-terminal zinc finger domain (ZnF-UBP domain, also known as BUZ) that binds free ubiquitin, as well as mono and polyubiquitinated proteins, with high affinity. HDAC6 is localized predominantly in the cytoplasm, and has been reported as a tubulin deacetylase that has effects on microtubule (MT)-mediated processes through both deacetylase-dependent and deacetylase-independent mechanisms. HDAC6 is important both for cytoplasmic and nuclear functions, including cell motility and controlling cytoskeletal dynamics. Unlike other deacetylases, HDAC6 has unique substrate specificity for non-histone proteins such as $\alpha$-tubulin, HSP90, cortactin, peroxiredoxins, chaperone proteins, $\beta$-Catenin, and hypoxia inducible factor-1$\alpha$ (HIF-1$\alpha$) (Blackwell et al., 2008, Life Science 82:1050-1058; Shnakar and Sirvastava, 2008, Adv Exp Med Biol 615:261-298). HDAC6 also deacetylates protein peroxiredoxins, which are proteins critical in protecting cells from the oxidative effects of $H_2O_2$ (Parmigiani et al., 2008, PNAS 105:9633-9638). However, HDAC6 does not catalyze histone deacetylation in vivo. Therefore, it is a safer drug target since it does not impact DNA biology. As a MT-mediated cytoplasmic enzyme, HDAC6, through complexes with partner proteins, regulates multiple important biological processes, such as cell migration, cell spreading, immune synapse formation, viral infection, the degradation of misfolded proteins and stress granule (SG) formation. HDAC6 is a vital regulator for mitochondrial transport; inhibiting HDAC6 promotes the mitochondrial dynamics in A$\beta$-treated neurons. Inhibiting HDAC6 via deacetylating $\alpha$-tubulin significantly restored the length of the mitochondria shortened by A$\beta$ to a normal level and rescued hippocampal neuron impairment induced by A$\beta$. Mice lacking HDAC6 are viable and have greatly elevated tubulin acetylation in multiple organs. In addition, mice lacking HDAC6 exhibit a moderately impaired immune response and bone homeostasis. In addition, mice lacking HDAC6 exhibit a moderately impaired immune response and bone homeostasis. HDAC6 selective inhibitors, Tubastatin A and Ricolinostat (ACY-1215), have demonstrated the capability of improving microtubule stability and ameliorate cognitive impairment in Alzheimer's diseases mouse by promoting tubulin acetylation, reducing production of A$\beta$ and hyper-phosphorylated tau and facilitating autophagic clearance of A$\beta$ and hyper-phosphorylated tau. Compared to HDAC Pa-inhibitor, such as SAHA, HDAC6 selective inhibitors will have much less toxic effects, which is very important especially for chronic indications. The current most advanced HDAC6 selective HDAC6 inhibitor is Ricolinostat, which has been multiple clinical trials. For example, as a mono agent and combination agent with Bortezomib, Dexamethasone, Pomalidomide and Lenalidomide respectively, Ricolinostat had clinical trials for Multiple Myeloma and in Relapsed-and-Refractory Multiple Myeloma, relapsed/refractory Lymphoid Malignancies; combination with BCR pathway Inhibitors for relapsed chronic lymphocytic leukemia; combination with Nab-paclitaxel for metastatic breast cancer etc. Such diverse functions of HDAC6 suggest that HDAC6 serves a potential therapeutic target for the treatment of a wide range of diseases. HDAC6 selective inhibitors have been tested in preclinical indications for cancers, neurology, inflammation, Gaucher's disease, Parkinson's disease, Huntington's disease; Alzheimer's diseases, depression and anxiety, and pain etc. (Gianniniet et al., 2012, Future Med Chem. 4:1439-1460; Falkenberg and Johnstone, 2014, Nat Rev Drug Discov. 13:673-91; Mottamal et al. 2015 Molecules, 20:3898-3941; Yang et al. 2017 Translational Neurodegeneration, 6:19).

HDAC8, on the basis of sequence homology, is considered to be a class I enzyme, although phylogenetic analysis has shown it to lay near the boundary of the class I and class II enzymes. HDAC8's importance has been revealed by knockdown experiments of selective HDAC isoforms showing it as essential for cell survival. HDAC8 specific inhibition selectively induces apoptosis in T-cell derived lymphoma and leukemic cells. The expression of HDAC8 has been described in a variety of cancer entities e.g. colon, breast lung, pancreas and ovary cancer (Nakagawa et al. 2007, Oncol Rep, 18:769-774). In the highly malignant childhood cancer neuroblastoma high HDAC8 expression significantly correlates with poor prognostic markers and poor overall and event-free survival. In cultured neuroblastoma cells knockdown and pharmacological inhibition of HDAC8 resulted in inhibition of proliferation, reduced clonogenic growth, cell cycle arrest and differentiation (Oehme et al. 2009, Clin Cancer Res, 15:91-99). Furthermore, HDAC8 promotes lung, colon and cervical cancer cell proliferation and may regulate telomerase activity. The three dimensional crystal structure of human HDAC8 was the first to be solved, and 14 human HDAC8 structures co-crystallized with different inhibitors have been described. Currently, HDAC8 selective inhibitors are in preclinical trials for cancer (Giannini G et al., 2012, Future Med Chem. 4:1439-1460; Falkenberg and Johnstone, 2014, Nat Rev Drug Discov. 13:673-91).

Sirtuins 1-7 (SIRT1-7) belong to the third class of deacetylase enzymes, which are dependent on NAD(+) for activity. Sirtuins activity is linked to gene repression, metabolic control, apoptosis and cell survival, DNA repair, development, inflammation, neuroprotection, and healthy aging. Because sirtuins modulation could have beneficial effects on human diseases there is a growing interest in the discovery of small molecules modifying their activities. Sirtuin inhibitors with a wide range of core structures have been identified for SIRT1, SIRT2, SIRT3 and SIRT5 (splitomicin, sirtinol, AGK2, cambinol, suramin, tenovin, salermide, among others). SIRT1 inhibition has been proposed in the treatment of cancer, immunodeficiency virus infections, Fragile X mental retardation syndrome and for preventing or treating parasitic diseases, whereas SIRT2 inhibitors might be useful for the treatment of cancer and neurodegenerative diseases. (Villalba et al 2012, 38(5):349-59; Chen L, Curr Med Chem. 2011; 18(13):1936-46).

Thus, there remains a need in the art for inhibitors of HDACs having high selectivity within and between various HDAC classes, which can serve as therapeutic agents against a variety of diseases and disorders. There also remains a need in the art for novel inhibitors of SIRTs having high selectivity within and between various SIRT classes, which can serve as therapeutic agents against a variety of diseases and disorders. The present invention fulfills this need.

SUMMARY OF THE INVENTION

In one aspect, the invention relates to a compound of Formula I or a salt or solvate thereof:

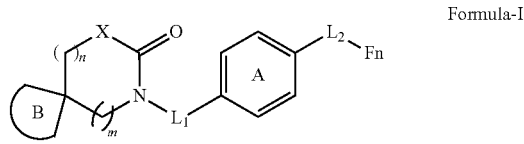

Formula-I wherein in Formula-I:

Ring A is an aromatic ring having 0-2 ring nitrogen atoms;

Ring B is a 3-7 membered saturated or unsaturated carbocyclic ring, or a 3-7 membered saturated or unsaturated heterocyclic ring having 1-3 ring atoms of O, S, SO, $SO_2$, or $NR^a$, and wherein Ring B may optionally be substituted by one or more $R^b$s;

$L_1$ is a bond or a $C_1$-$C_3$ alkyl group optionally substituted by $R^b$;

$L_2$ is a bond, a $C_1$-$C_3$ alkyl group optionally substituted by $R^b$, an alkenyl, or an alkynyl;

X is $CH_2$, O, or $NR^c$;

each $R^a$ and $R^b$ is independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein each $R^d$, $R^e$ and $R^f$ is independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ may be optionally joined to form additional rings; and any $R^a$ and $R^b$ may be optionally joined to form additional rings;

$R^c$ is selected from the group consisting of H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ may be optionally joined to form additional rings;

Fn is selected from the group consisting of Formulae II, III, IV and V:

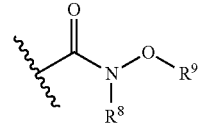

Formula II

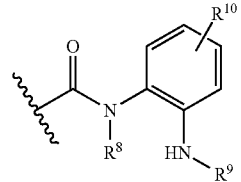

Formula III

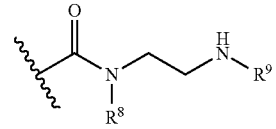

Formula IV

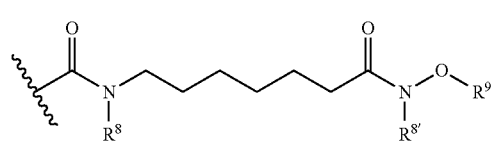

Formula V wherein in Formulae II, III, IV and V:

$R^8$, $R^{8'}$, $R^9$, and $R^{10}$ are each independently selected from the group consisting of H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl may optionally be substituted, and $R^{10}$ can represent single, multiple, or no substitution;

m is an integer from 0-3; and n is an integer from 0-3.

In one embodiment, the compound is selected from the group consisting of
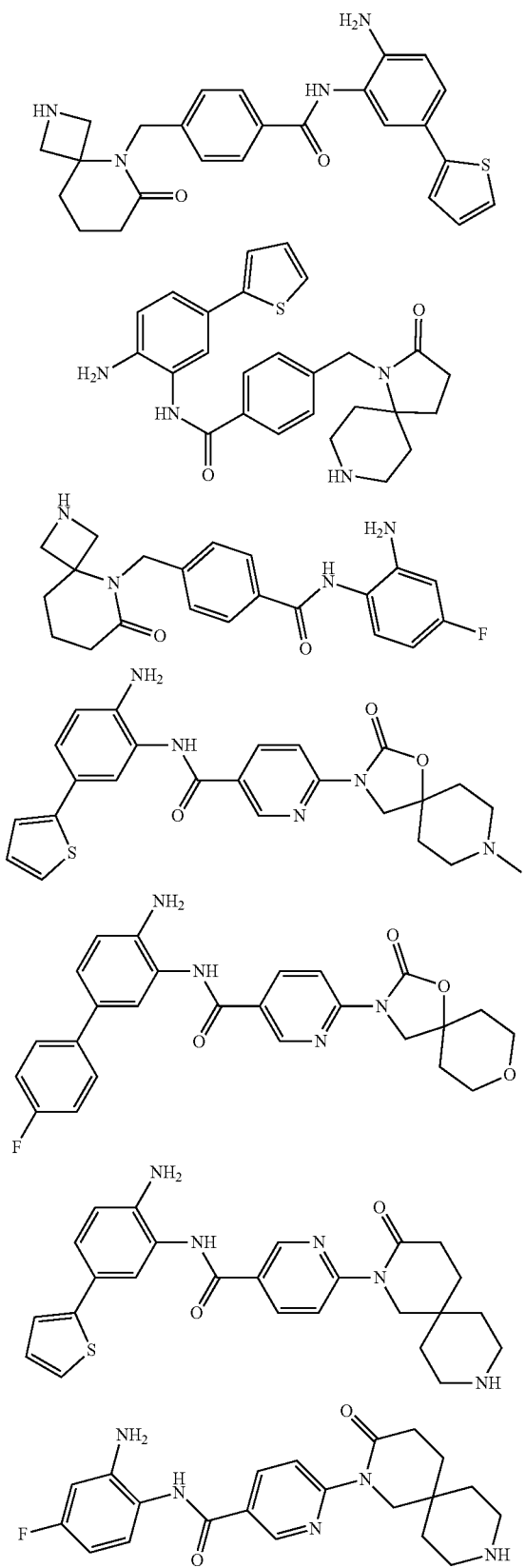
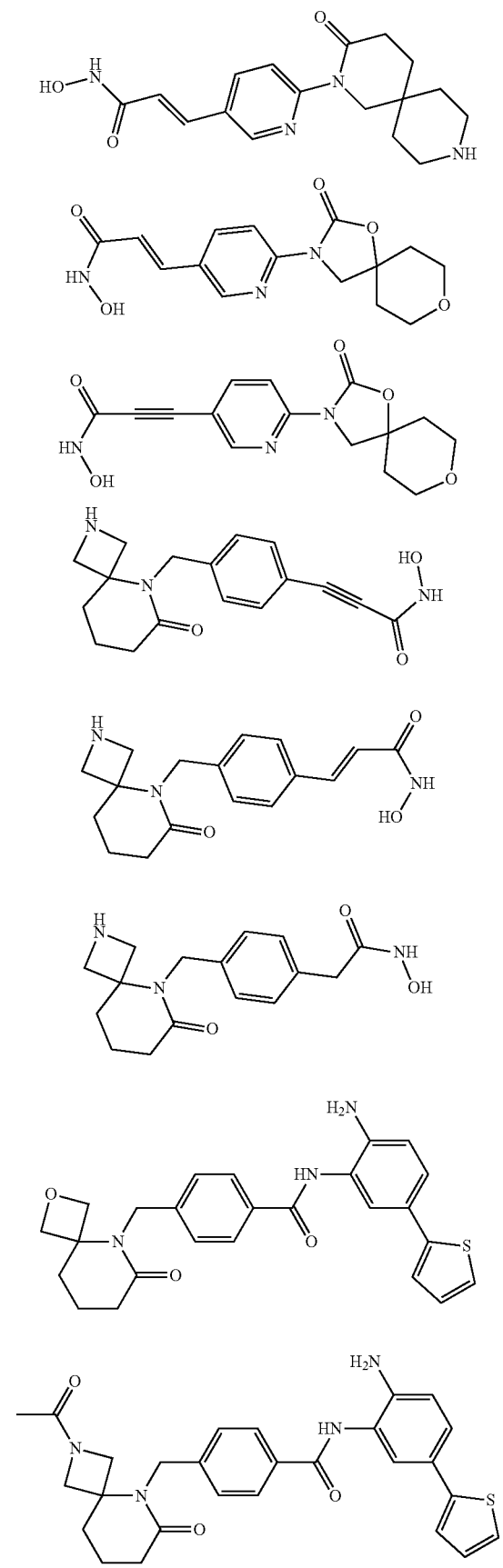

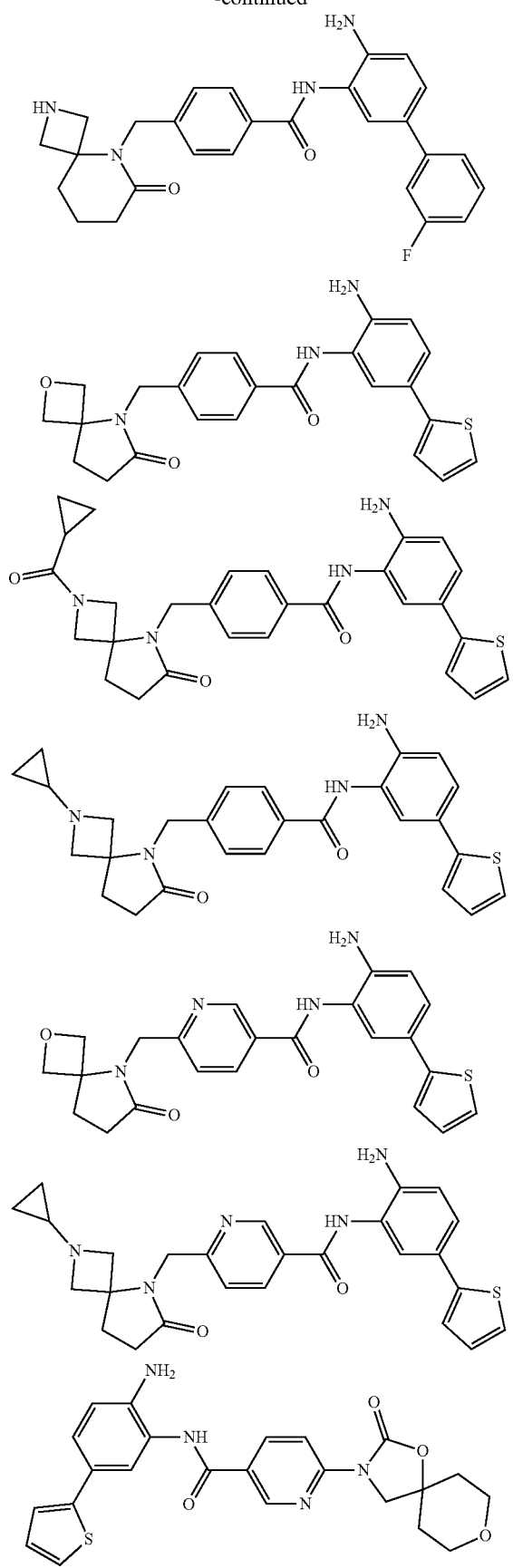
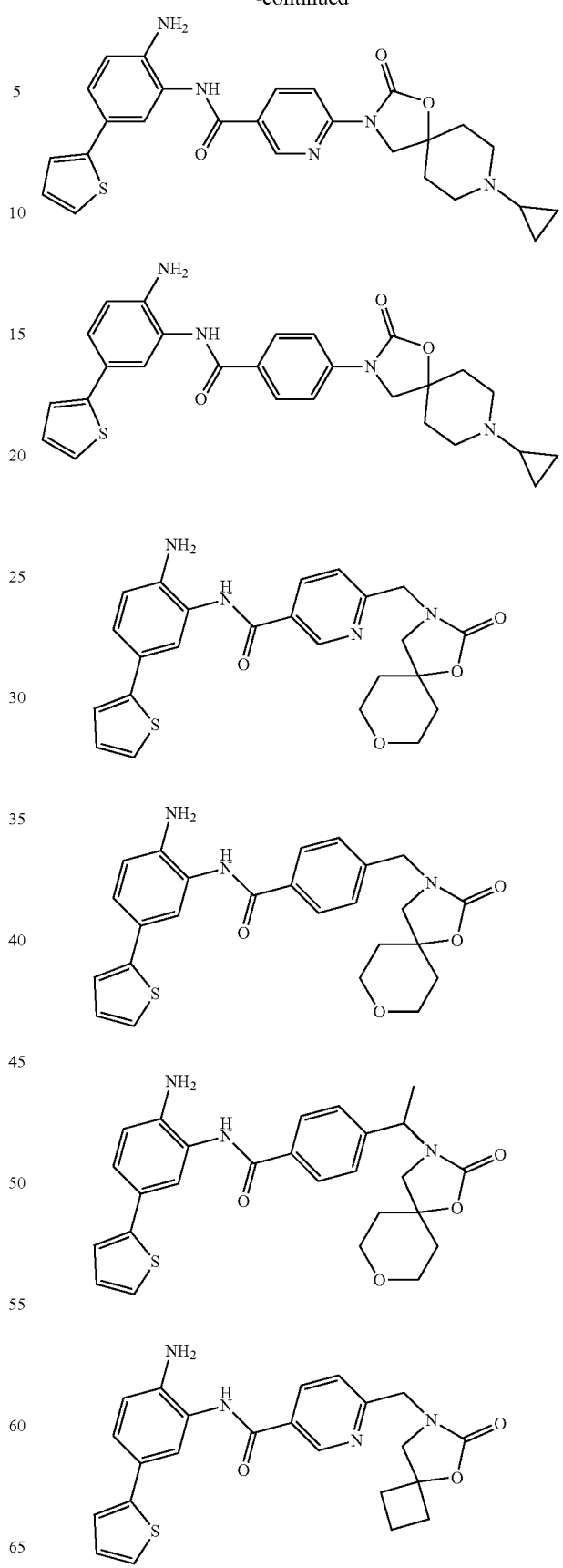

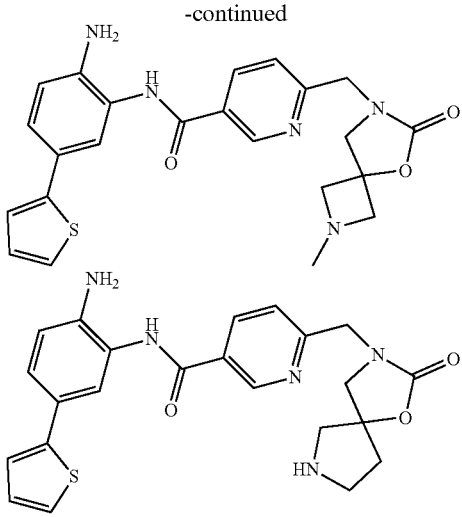

In another aspect, the present invention includes a compound of Formula I-A or Formula I-B, or a salt or solvate thereof:

Formula I-A

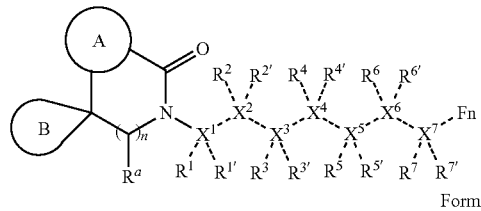

Formula I-B

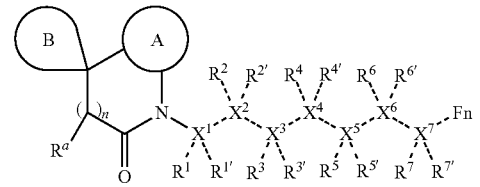

wherein in Formula I-A and Formula I-B:

Ring A is an aromatic ring having 0-3 ring nitrogen atoms, and wherein Ring A may optionally be substituted by one or several $R^b$;

Ring B is a saturated or unsaturated 3-7 membered carbocyclic ring or a saturated or unsaturated 3-7 membered heterocyclic ring having 1-3 ring atoms of O, S, SO, $SO_2$, or $NR^b$, and wherein Ring B may optionally be substituted by one or several $R^c$;

$R^a$, $R^b$ and $R^c$ are each independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ can optionally be joined to form additional rings; and $R^a$, $R^b$ and $R^c$ can optionally be joined to form additional rings;

chain

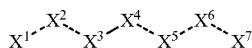

is an uninterrupted chain, wherein any bond can be a single, double or triple bond, consistent with the hybridization state of the connected atoms, and wherein a null selection for any of the $X^1$ to $X^7$ nodes results in a null selection for the adjacent R groups;

$X^1$, $X^2$, $X^3$, $X^4$, $X^5$, $X^6$, and $X^7$ are each independently selected from the group consisting of null, C, CH, $CH_2$, $C(=O)$, O, N, NH, S, $S(=O)$ and $S(=O)_2$;

$R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$ are each independently selected from the group consisting of null, H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ can optionally be joined to form additional rings; and any of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$ can optionally be connected to each other to form various carbocyclic or heterocyclic systems; and Fn is selected from the group consisting of Formulae II, III, IV and V:

Formula II

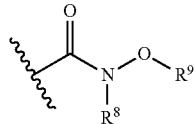

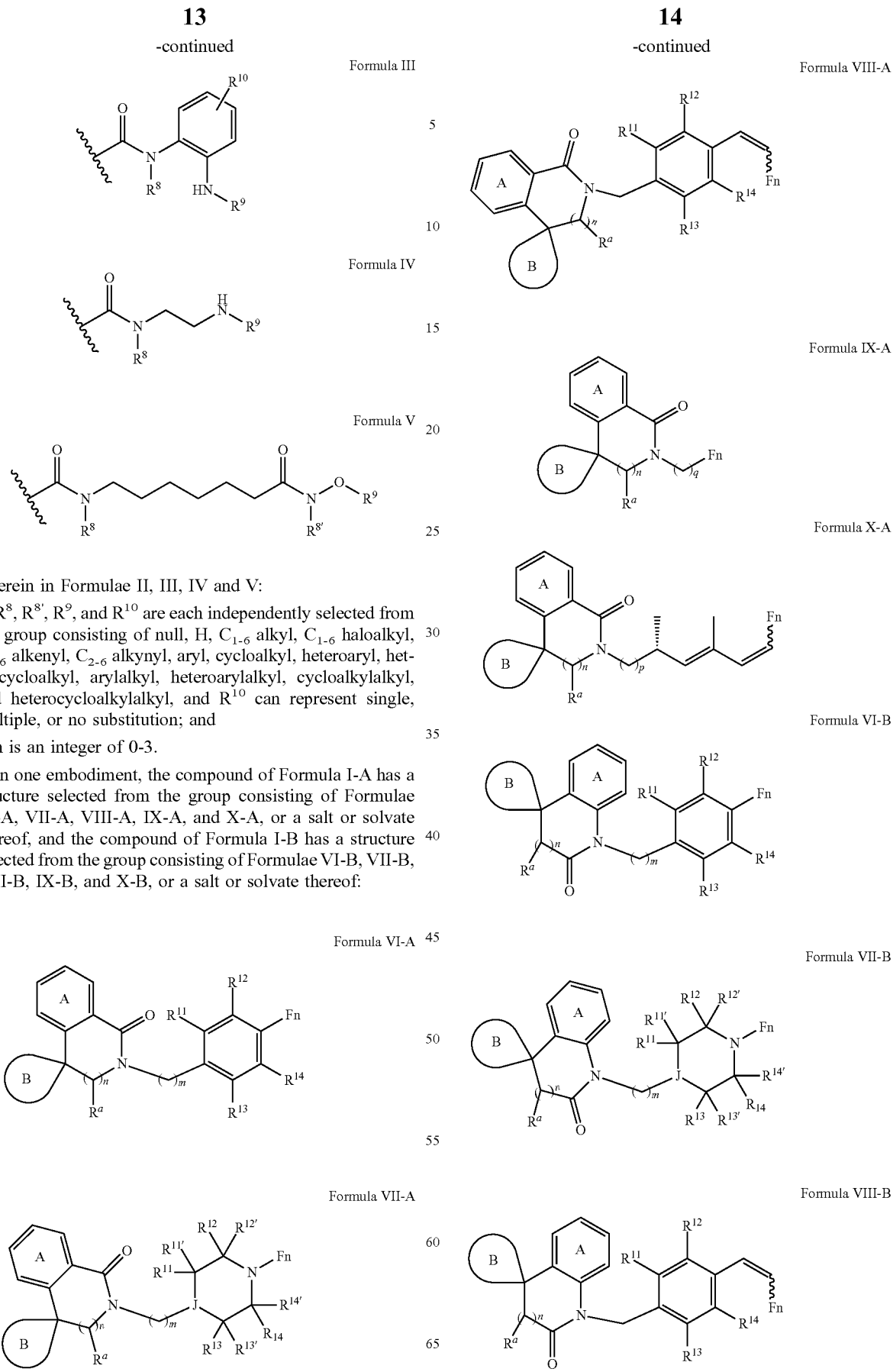

wherein in Formulae II, III, IV and V:

$R^8$, $R^{8'}$, $R^9$, and $R^{10}$ are each independently selected from the group consisting of null, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution; and n is an integer of 0-3.

In one embodiment, the compound of Formula I-A has a structure selected from the group consisting of Formulae VI-A, VII-A, VIII-A, IX-A, and X-A, or a salt or solvate thereof, and the compound of Formula I-B has a structure selected from the group consisting of Formulae VI-B, VII-B, VIII-B, IX-B, and X-B, or a salt or solvate thereof:

Formula IX-B

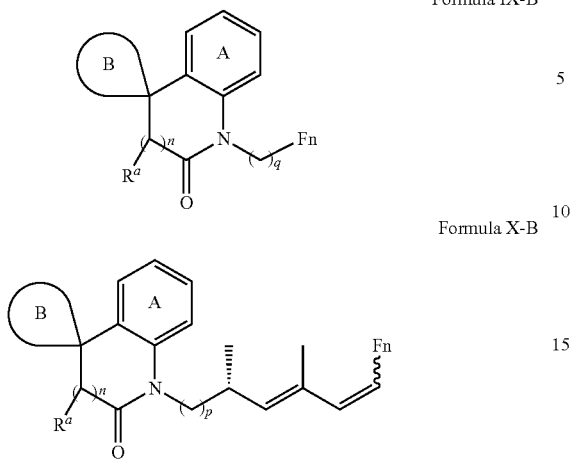

Formula X-B wherein in Formulae VI-A to X-B:

$R^{11}$, $R^{12}$, $R^{13}$, $R^{14}$, and $R^{14'}$ are each independently selected from the group consisting of H, F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, and wherein each R$^d$, R$^e$ and R$^f$ is independently selected from the group consisting of H and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of R$^d$, R$^e$ or R$^f$ can optionally be joined to form additional rings; and any of R$^{11}$, R$^{12}$, R$^{13}$, R$^{14}$, and R$^{14'}$ can optionally be connected to each other to form various carbocyclic or heterocyclic rings;

m is an integer from 0 to 3;

q is an integer from 0 to 7;

p is an integer from 0 to 2;

J is selected from the group consisting of CH and N; and

Fn is selected from the group consisting of Formulae II, III, IV and V:

Formula II

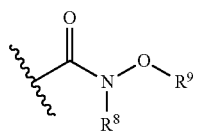

Formula III

Formula IV

Formula V wherein in Formulae II, III, IV and V:

$R^8$, $R^{8'}$, $R^9$, and $R^{10}$ are each independently selected from the group consisting of null, H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution.

In one embodiment, the compound of Formulae VI-A, VII-A, VIII-A, IX-A, and X-A, VI-B, VII-B, VIII-B, IX-B, or X-B is selected from the group consisting of:

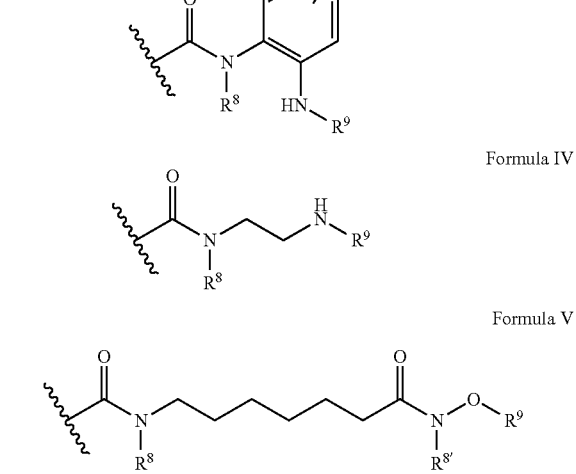

17
-continued
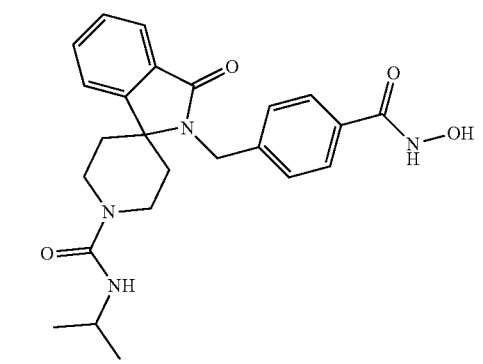
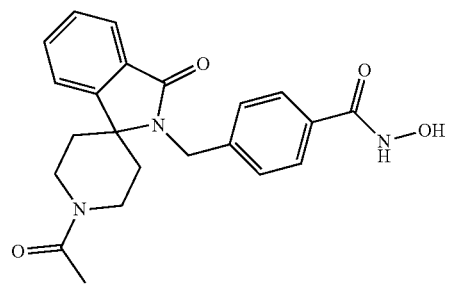
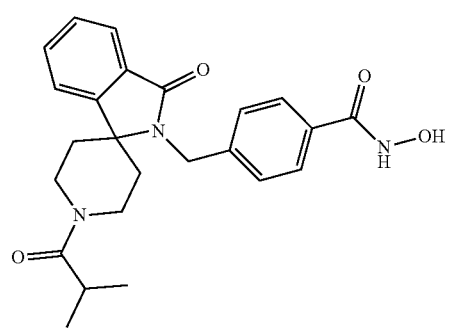
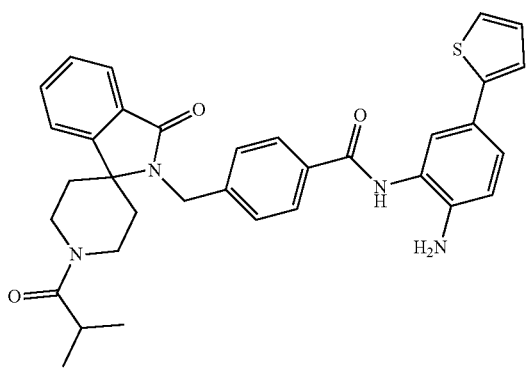
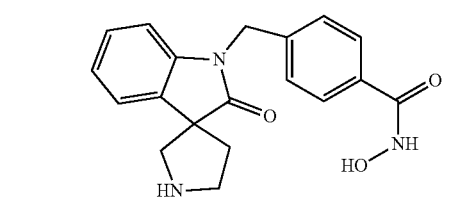
18
-continued
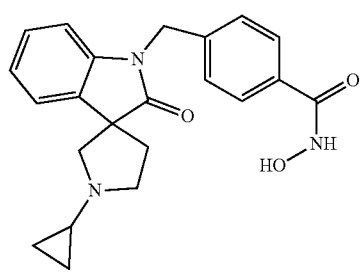
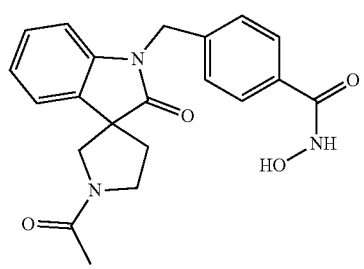
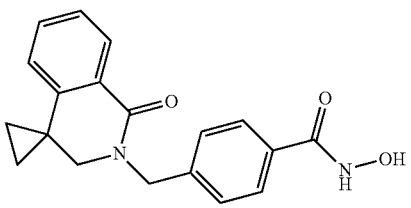
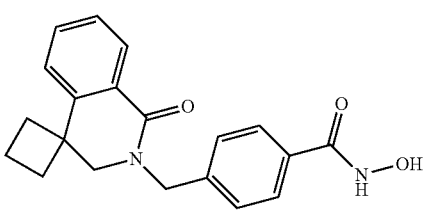
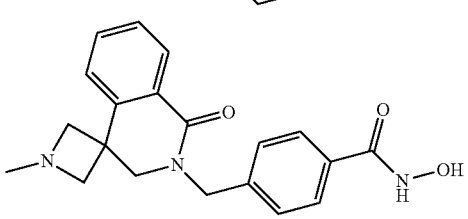
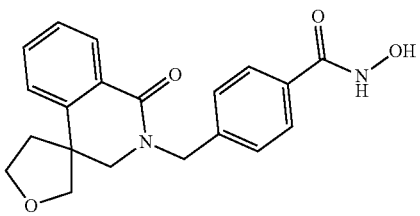
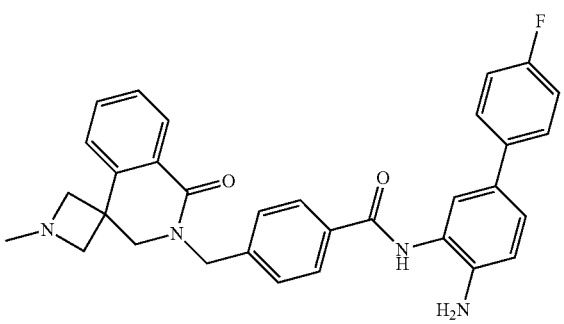

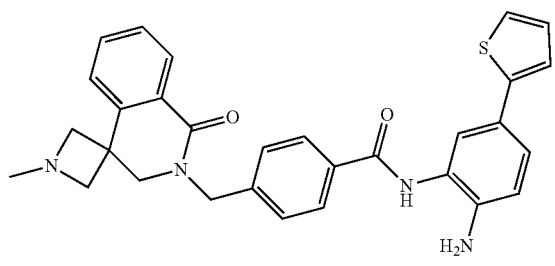
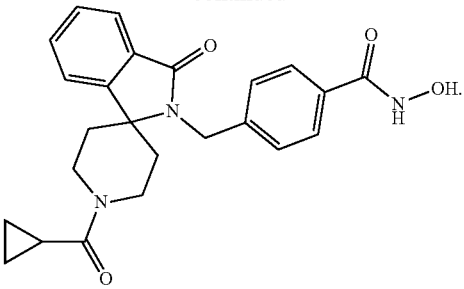
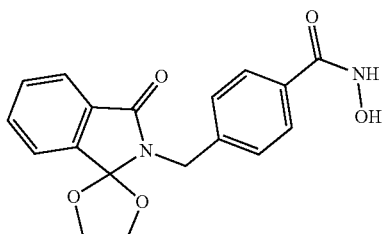
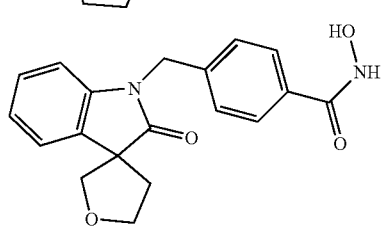
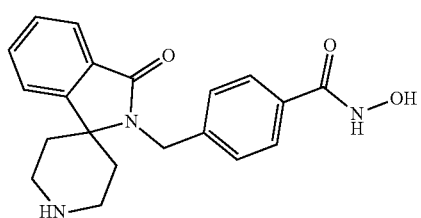
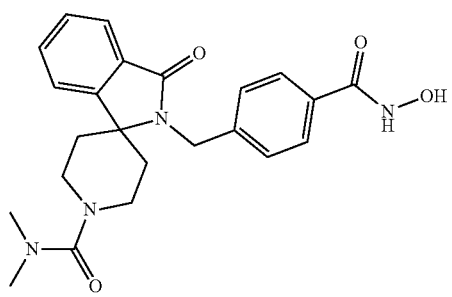
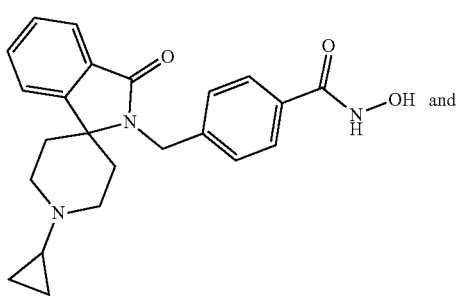

and

The present invention also includes a composition comprising a compound of the invention, or a salt or solvate thereof, and at least one pharmaceutically acceptable carrier.

In one aspect, the invention relates to a composition comprising a compound of Formula I-A, and/or Formula I-B, or a salt or solvate thereof, and at least one pharmaceutically acceptable carrier.

In another aspect, the invention relates to a method of treating a disease or disorder associated with HDACs in a subject, the method comprising administering to the subject a therapeutically effective amount of a compound of Formula I-A, and/or a compound of Formula I-B, or a salt or solvate thereof. In one embodiment, the compound of Formula I-A has a chemical structure selected from the group consisting of Formulae VI-A, VII-A, VIII-A, IX-A, and X-A, or a salt or solvate thereof. In another embodiment, the compound of Formula I-B has a chemical structure selected from the group consisting of Formulae VI-B, VII-B, VIII-B, IX-B, and X-B, or a salt or solvate thereof.

In one embodiment, the compound selectively inhibits HDAC1. In another embodiment, the compound selectively inhibits HDAC2. In one embodiment, the compound selectively inhibits both HDAC1 and HDAC2. In one embodiment, the compound selectively inhibits HDAC3. In one embodiment, the compound selectively inhibits HDAC4. In one embodiment, the compound selectively inhibits HDAC5. In one embodiment, the compound selectively inhibits HDAC6. In one embodiment, the compound selectively inhibits HDAC7. In one embodiment, the compound selectively inhibits HDAC8. In one embodiment, the compound selectively inhibits HDAC9. In one embodiment, the compound selectively inhibits HDAC10. In one embodiment, the compound selectively inhibits HDAC11. In one embodiment, the compound selectively inhibits SIRT1. In one embodiment, the compound selectively inhibits SIRT2. In one embodiment, the compound selectively inhibits SIRT3. In one embodiment, the compound selectively inhibits SIRT4. In one embodiment, the compound selectively inhibits SIRT5. In one embodiment, the compound selectively inhibits SIRT6. In one embodiment, the compound selectively inhibits SIRT7.

The present invention also includes a method of treating a disease or disorder associated with HDACs in a subject. In one embodiment, the method includes administering to the subject a therapeutically effective amount of a compound of the invention, or a salt or solvate thereof. In one embodiment, the subject is a human. In one embodiment, the disease or disorder is cancer. In one embodiment, the disease or disorder is a psychiatric disease or disorder. In one embodiment, the disease or disorder is a neurologic disease or disorder. In one embodiment, the disease or disorder is a neurodegenerative disease or disorder. In one embodiment, the disease or disorder is a neuroinflammation disease or disorder. In one embodiment, the compound is administered to the subject orally, parenterally, intravascularly, intranasally, or intrabronchially.

The present invention also includes a method of inhibiting HDACs in a subject. In one embodiment, the method includes administering to the subject a therapeutically effective amount of a compound of the invention, or a salt or solvate thereof. In one embodiment, the subject has a disease or disorder selected from the group consisting of cancer, a psychiatric disease or disorder, a neurologic disease or disorder, a neurodegenerative disease or disorder, and a neuroinflammation disease or disorder.

In one embodiment, the method further comprises administering to the subject a therapeutically effective amount of an additional therapeutic agent for the treatment of a disease or disorder. In one embodiment, the additional therapeutic agent is selected from the group consisting of an immunomodulatory drug, an immunotherapeutic drug, a DNA-damaging chemotherapeutic, a proteasome inhibitor, an anti-androgen receptor, an antiretroviral drug, a reverse-transcriptase inhibitor, a chemotherapeutic drug, and an immunosuppressant.

In one aspect, the invention relates to a method of immunomodulation for organ transplant, the method comprising administering to a patient a therapeutically effective amount of a compound of the invention or a salt or solvate thereof.

In one aspect, the invention relates to a kit for inhibiting an HDAC, comprising an amount of a compound of Formula I or a salt or solvate thereof, and an instruction manual for the use thereof.

In one aspect, the invention relates to a kit for treating a disease or disorder associated with an HDAC in a subject, comprising an amount of a compound of the invention, or a salt or solvate thereof, and an instruction manual for the use thereof.

In one aspect, the invention relates to a probe for imaging, diagnosing, or theragnosting a disease or disorder associated with an HDAC in a subject, comprising a compound of the invention, or a salt or solvate thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
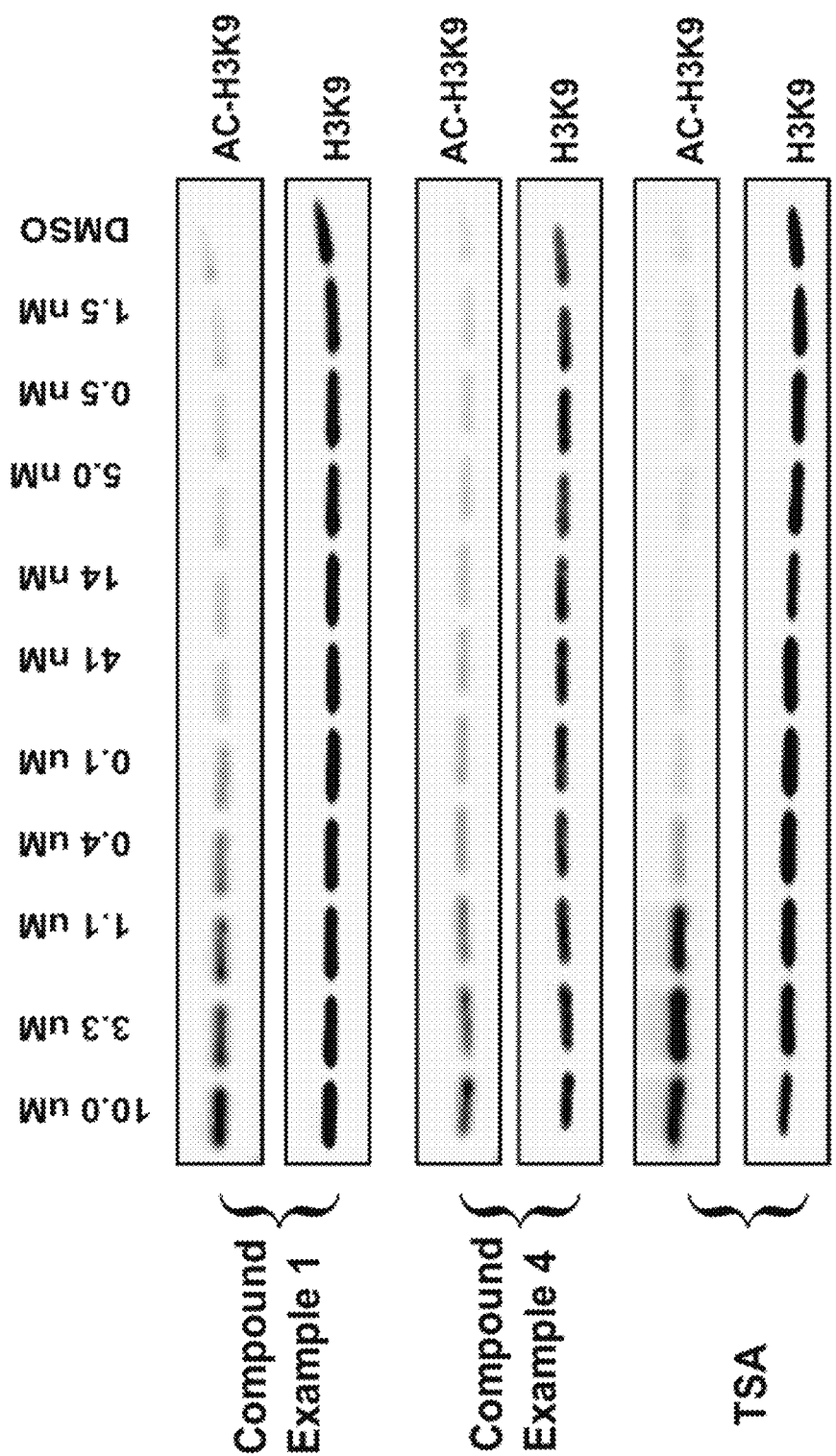
FIG. 1 depicts a Western blot of Compound Example 1 and Compound Example 4.

The present invention provides novel compounds that are useful for modulating the activity of HDACs, and may be useful as therapeutics for various diseases and disorders, including but not limited to cancer, psychiatric disorders, neurologic disorders and neurodegenerative disorders, inflammation, virus infection, and bone and muscle-related disorders such as cancer-induced cachexia.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e., to at least one) of the grammatical object of the article. By way of example, "an element" means one element or more than one element.

The term "about" as used herein when referring to a measurable value such as an amount, a temporal duration, and the like, is meant to encompass variations of ±20% or ±10%, more preferably ±5%, even more preferably ±1%, and still more preferably ±0.1%

The terms "patient," "subject," "individual," and the like are used interchangeably herein, and refer to any animal, including mammals. In certain non-limiting embodiments, the patient, subject or individual is a human.

A "disease" is a state of health of an a subject wherein the subject cannot maintain homeostasis, and wherein if the disease is not ameliorated, the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. As used herein, "treating a disease or disorder" means reducing the frequency and/or severity with which a symptom of the disease or disorder is experienced by an individual.

The term "treat," as used herein, means reducing the frequency and/or severity of a sign or symptom of a disease or disorder experienced by a subject. Thus, "treat" and "treating" are not limited to the case where the subject (e.g., patient) is cured and the disease or disorder is eradicated. Rather, the present invention also contemplates treatment that merely reduces signs or symptoms, improves (to some degree) and/or delays disease or disorder progression. The term "treatment" also refers to the alleviation, amelioration, and/or stabilization of signs or symptoms, as well as a delay in the progression of signs or symptoms of a disease or disorder. As used herein, to "alleviate" a disease or disorder means to reduce the frequency and/or severity of one or more signs and/or symptoms of the disease or disorder.

The term "effective amount" in a subject, as used herein, refers to an amount that provides a therapeutic or prophylactic benefit in the subject. The term "therapeutically effective amount" refers to the amount of the compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the signs and/or symptoms of the disease or disorder being treated. The therapeutically effective amount will vary depending on the compound, the disease or disorder, the severity of the disease or disorder, and the age, weight, etc., of the subject to be treated.

The term "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "composition" refers to a mixture of at least one compound or molecule useful within the invention with one or more different compound, molecule, or material. As used herein "pharmaceutical composition" or "pharmaceutically acceptable composition" refers to specific examples of compositions, wherein at least one compound or molecule useful within the invention is mixed with one or more pharmaceutically acceptable carriers. In some instances, the pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "alkyl," by itself or as part of another substituent means, unless otherwise stated, a straight or branched chain hydrocarbon having the number of carbon atoms designated (i.e., $C_1$-$C_6$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, particularly ethyl, methyl, isopropyl, isobutyl, n-pentyl, n-hexyl and cyclopropylmethyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

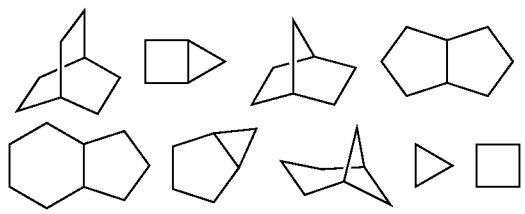

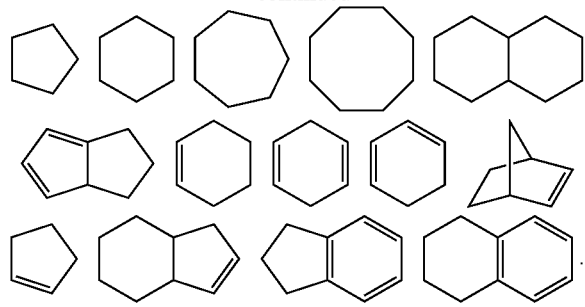

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

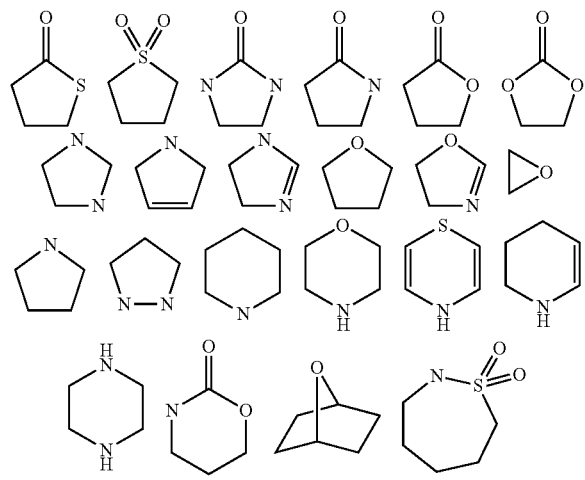

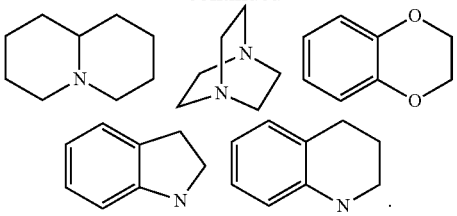

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized $\pi$ (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "heteroaryl" or "heteroaromatic" refers to a heterocycle having aromatic character. A polycyclic heteroaryl may include one or more rings that are partially saturated. Examples include the following moieties:

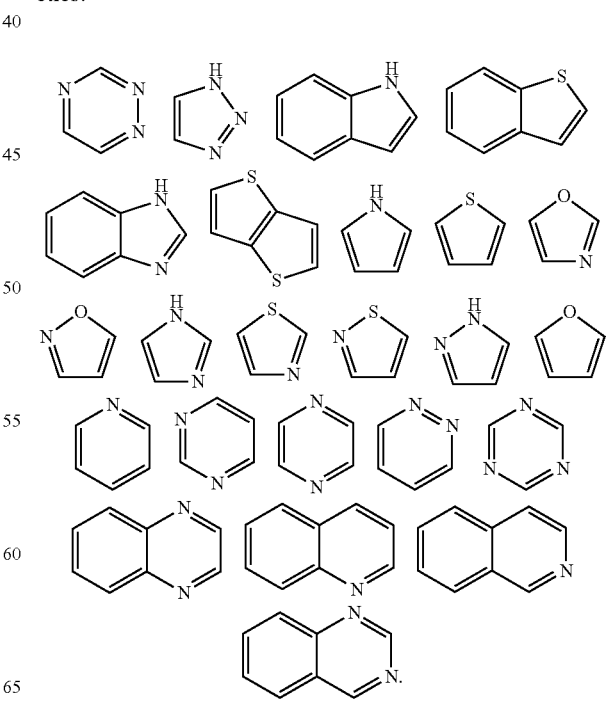

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or pentasubstitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

As used herein, an "instructional material" or "instruction manual" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range and, when appropriate, partial integers of the numerical values within ranges. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds of the Invention

In one aspect, the invention relates to a compound with the chemical structure depicted in Formula I, or a pharmaceutically acceptable salt, or solvate thereof:

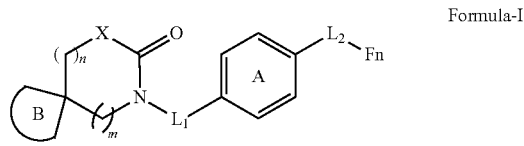

Formula-I wherein in Formula I:

Ring A is an aromatic ring having 0-2 ring nitrogen atoms;

Ring B is a 3-7 membered saturated or unsaturated carbocyclic ring, or a 3-7 membered saturated or unsaturated heterocyclic ring having 1-3 ring atoms of O, S, SO, SO$_2$, or NR$^a$, and wherein Ring B may optionally be substituted by one or more R$^b$s;

L$_1$ is a bond or a C$_1$-C$_3$ alkyl group optionally substituted by R$^b$;

L$_2$ is a bond, a C$_1$-C$_3$ alkyl group optionally substituted by R$^b$, an alkenyl, or an alkynyl;

X is CH$_2$, O, or NR$^c$;

each R$^a$ and R$^b$ is independently selected from the group consisting of H, F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein each $R^d$, $R^e$ and $R^f$ is independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ may be optionally joined to form additional rings; and any $R^a$ and $R^b$ may be optionally joined to form additional rings;

$R^c$ is selected from the group consisting of H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ may be optionally joined to form additional rings;

Fn is selected from the group consisting of Formulae II, III, IV and V:

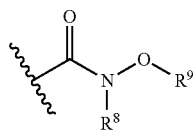

Formula II

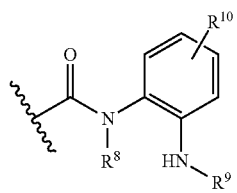

Formula III

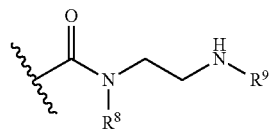

Formula IV

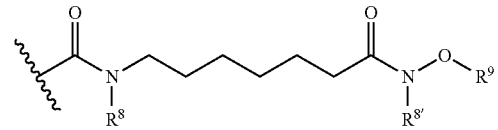

Formula V wherein in Formulae II, III, IV and V:

$R^8$, $R^{8'}$, $R^9$, and $R^{10}$ are each independently selected from the group consisting of H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl may optionally be substituted, and $R^{10}$ can represent single, multiple, or no substitution;

m is an integer from 0-3; and n is an integer from 0-3.

In one embodiment, Ring A is a 6-membered aromatic ring having 0-2 ring nitrogen atoms. In one embodiment, Ring A is phenyl or pyridyl.

In one embodiment, $L_2$ is selected from the group consisting of a bond, a $C_1$ alkyl group, an alkenyl, and an alkynyl.

In one embodiment, Fn is a group of Formula III.

In one embodiment, $R^8$ is H.

In one embodiment, $R^9$ is H.

In one embodiment, $R^{10}$ is selected from the group consisting of H, aryl, substituted aryl, and heteroaryl. In one embodiment, $R^{10}$ is selected from the group consisting of H, substituted phenyl, and thiophenyl.

In one embodiment, $R^{10}$ is selected from the group consisting of

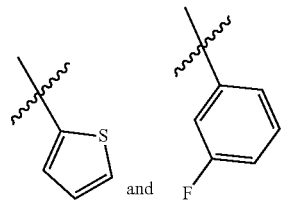

and

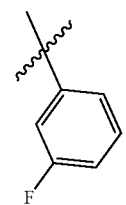

In one embodiment, Fn is a group of Formula II.

In one embodiment, $R^8$ is H.

In one embodiment, $R^9$ is H.

In one embodiment, Fn is selected from the group consisting of

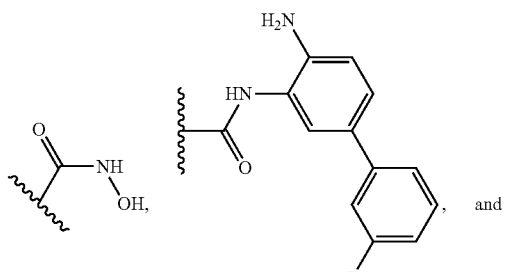

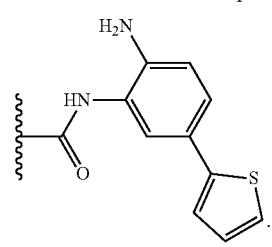

In one embodiment, $L_1$ is selected from the group consisting of a bond, a $C_1$ alkyl group, and a $C_1$ alkyl group substituted with $R^b$. In one embodiment, $L_1$ is selected from the group consisting of a bond, a $C_1$ alkyl group, and a $C_1$ alkyl group substituted with a —CH$_3$ group.

In one embodiment, X is selected from the group consisting of CH$_2$ and O.

In one embodiment, Ring B is selected from the group consisting of

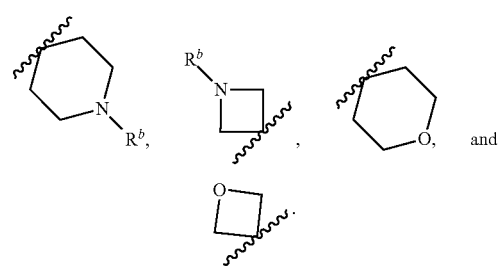

Non-limiting examples of Ring B include

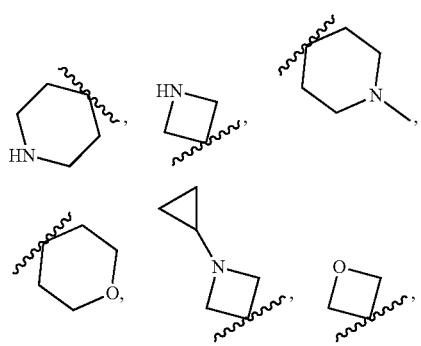

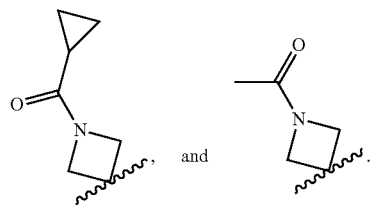

Non-limiting examples of compounds of the invention include

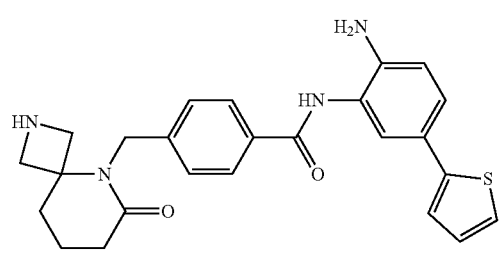 [SMILES: Nc1ccc(-c2cccs2)cc1NC(=O)c1ccc(CN2C(=O)CCCC23CNC3)cc1]

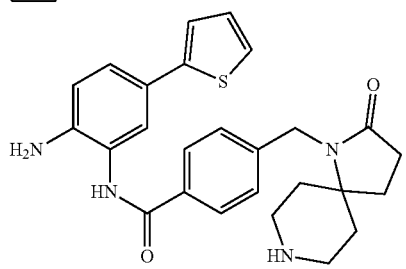

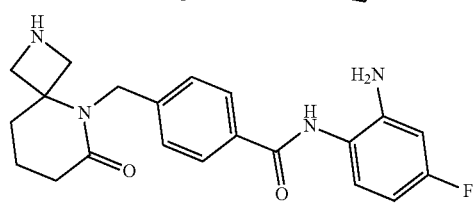

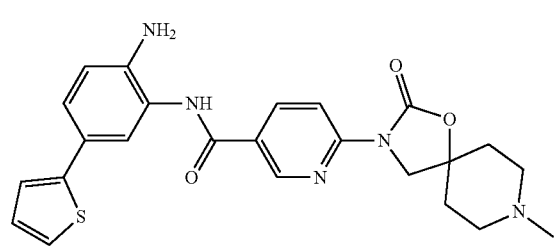

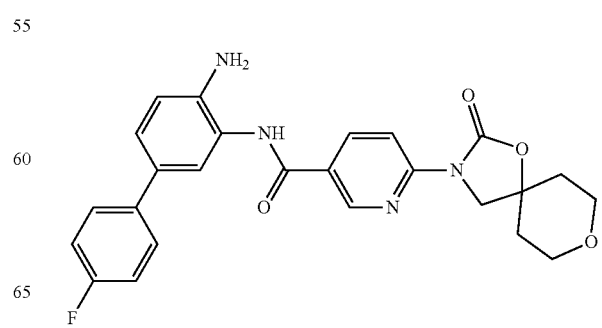

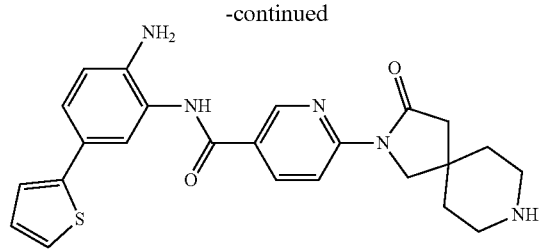
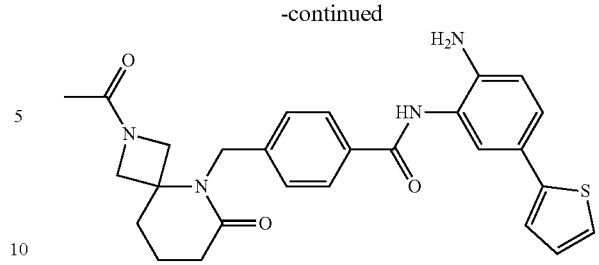
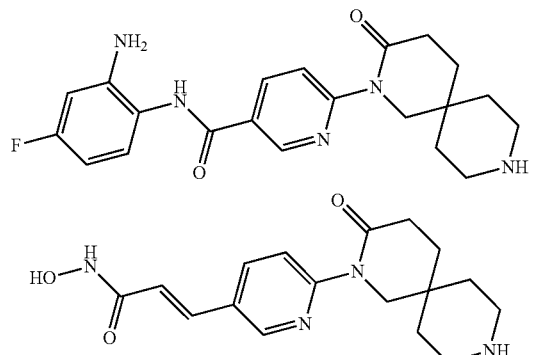
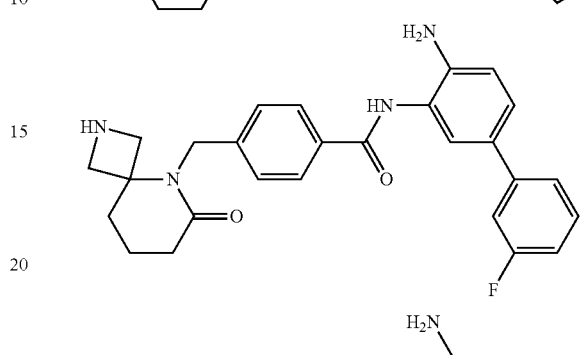
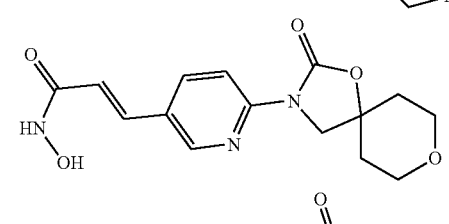
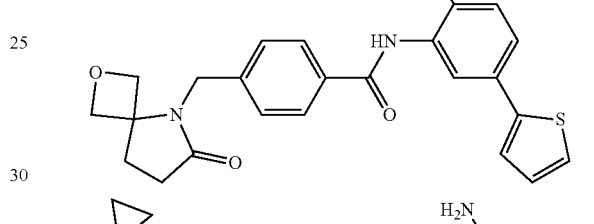
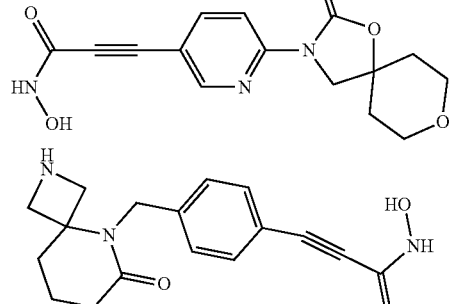
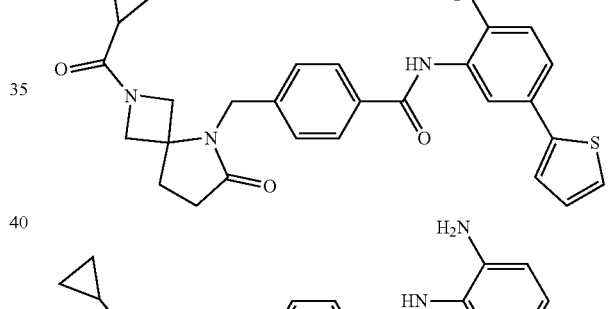
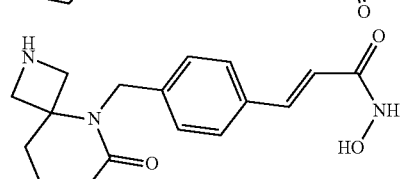
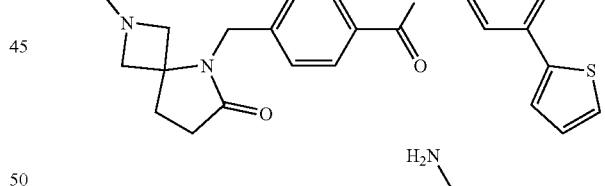
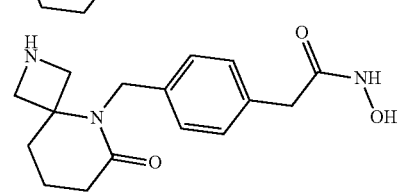
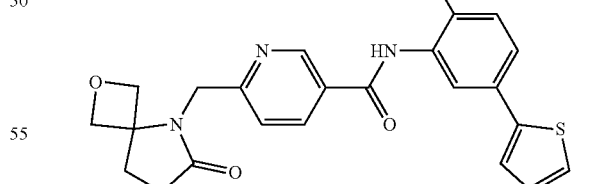
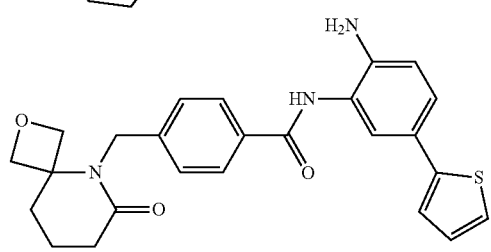
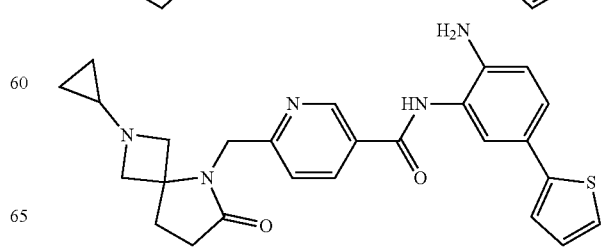

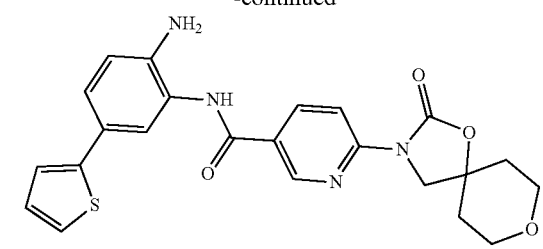
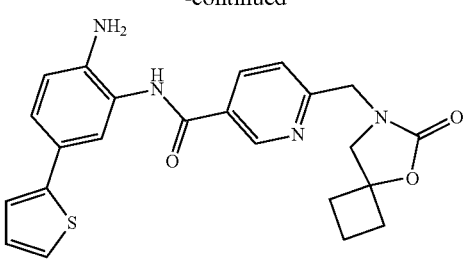
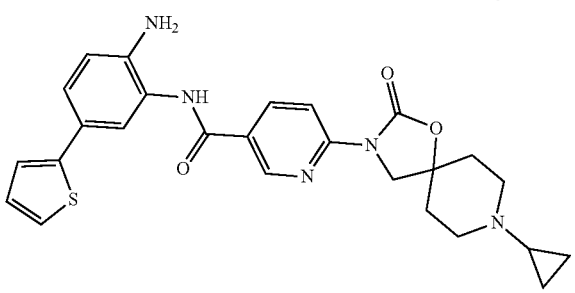
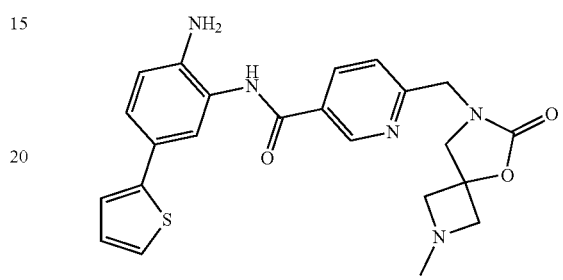
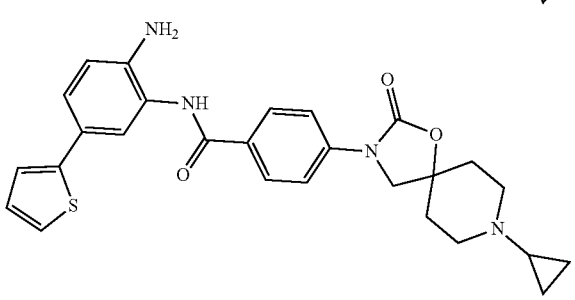
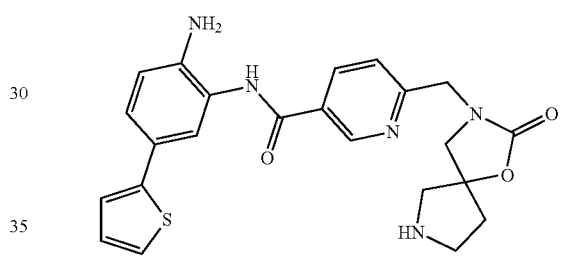
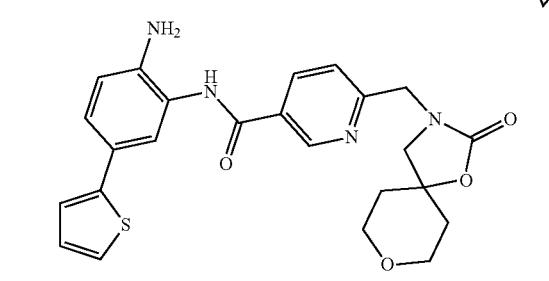
In one embodiment, the compound is
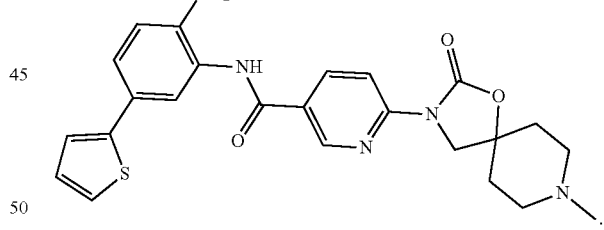
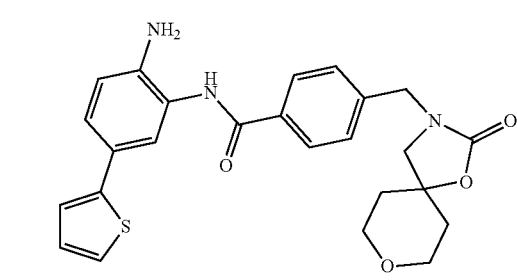
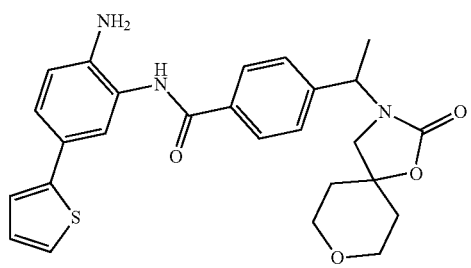
In one aspect, the present invention includes a compound of Formula I-A or Formula I-B, or a salt or solvate thereof:
Formula I-A
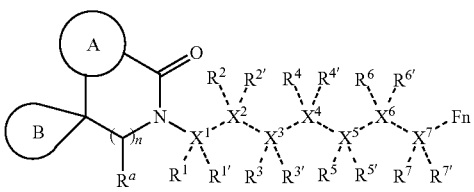

Formula I-B

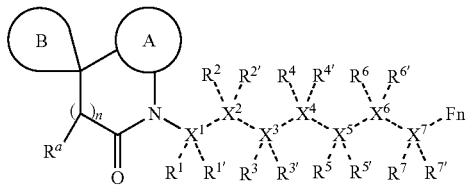

wherein in Formula I-A and Formula I-B:

Ring A is an aromatic ring having 0-3 ring nitrogen atoms, and wherein Ring A may optionally be substituted by one or more $R^b$s;

Ring B is a saturated or unsaturated 3-7 membered carbocyclic ring or a saturated or unsaturated 3-7 membered heterocyclic ring having 1-3 ring atoms of O, S, SO, $SO_2$, or $NR^b$, and wherein Ring B may optionally be substituted by one or more $R^c$s;

$R^a$, $R^b$ and $R^c$ are each independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ can optionally be joined to form additional rings; and $R^a$, $R^b$ and $R^c$ can optionally be joined to form additional rings;

chain $$X^1 - X^2 - X^3 - X^4 - X^5 - X^6 - X^7$$

is an uninterrupted chain, wherein any bond can be a single, double or triple bond, consistent with the hybridization state of the connected atoms, e.g. if $X^2$ is an sp hybridized carbon atom and $X^3$ is also an sp hybridized carbon atom, then the $X^2-X^3$ bond is a triple C—C bond, etc., wherein a null selection for any of the $X^1$ to $X^7$ nodes will result in connecting the adjacent nodes, e.g. if $X^5$ is null, then $X^4$ connects to $X^6$, or if $X^4$ and $X^5$ are both null, then $X^3$ connects with $X^6$, etc., and wherein a null selection for any of the $X^1$ to $X^7$ nodes will result in an automatic null selection for the adjacent R groups, e.g. if $X^3$ is null, then $R^3$ and $R^{3'}$ are both automatically null, etc.;

$X^1$, $X^2$, $X^3$, $X^4$, $X^5$, $X^6$, and $X^7$ are each independently selected from the group consisting of null, C, CH, $CH_2$, $C(=O)$, O, N, NH, S, $S(=O)$ and $S(=O)_2$;

$R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$ are each independently selected from the group consisting of null, H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ can optionally be joined to form additional rings; and any of $R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$ can optionally be connected to each other to form various carbocyclic or heterocyclic systems; and Fn is selected from the group consisting of Formulae II, III, IV and V:

Formula II

Formula III

Formula IV

Formula V wherein in Formulae II, III, IV and V:

$R^8$, $R^{8'}$, $R^9$, and $R^{10}$ are each independently selected from the group consisting of null, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution; and n is an integer of 0-3.

In one embodiment, Ring A is phenyl.

In one embodiment, Ring B is a saturated 3-7 membered heterocyclic ring having 1-3 ring atoms of O, S, SO, $SO_2$, or $NR^b$. In one embodiment, Ring B is selected from the group consisting of: dioxalane, tetrahydrofuran, piperidine, pyrrolidine, and azetidine; wherein Ring B may optionally be substituted by one or several $R^c$.

In one embodiment, Ring B is a saturated 3-7 membered carbocyclic ring. In one embodiment, Ring B is selected from the group consisting of cyclopropane and cyclobutane.

In one embodiment, Ring B is selected from the group consisting of

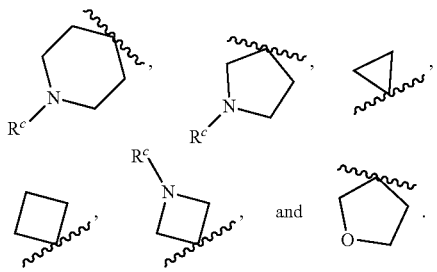

Non-limiting examples of Ring B include

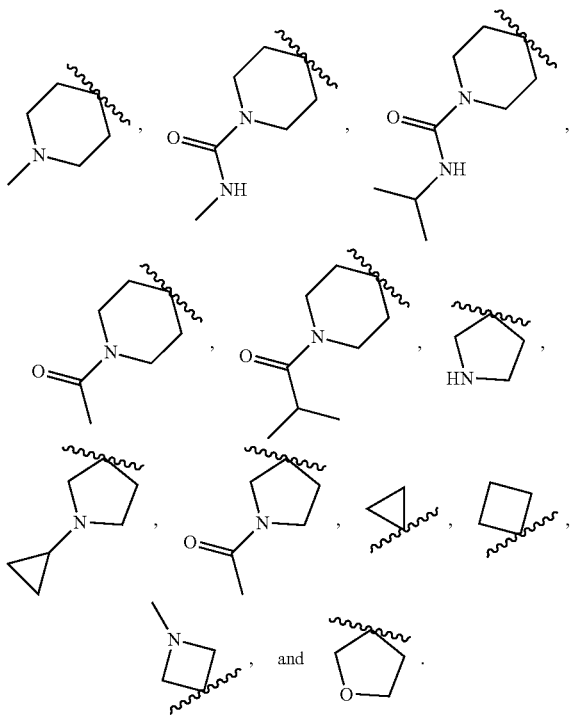

In one embodiment, $R^c$ is selected from the group consisting of hydrogen, alkyl, $C(=O)NR^dR^e$, $C(=O)R^d$, and cycloalkyl. In one embodiment, $R^c$ is hydrogen. In one embodiment, $R^c$ is alkyl. In one embodiment, the alkyl is a methyl group. In one embodiment, $R^e$ is $C(=O)NR^dR^e$ wherein one of $R^d$ or $R^e$ is hydrogen and the other of $R^d$ or $R^e$ is a methyl group. In one embodiment, $R^c$ is $C(=O)NR^dR^e$ wherein one of $R^d$ or $R^e$ is hydrogen and the other of $R^d$ or $R^e$ is an isopropyl group. In one embodiment, $R^c$ is $C(=O)R^d$ wherein $R^d$ is a methyl group. In one embodiment, $R^c$ is $C(=O)NR^dR^e$ wherein $R^d$ and $R^e$ are each a methyl group. In one embodiment, $R^c$ is $C(=O)R^d$ wherein $R^d$ is an isopropyl group. In one embodiment, $R^c$ is $C(=O)R^d$ wherein $R^d$ is a cyclopropane. In one embodiment, $R^c$ is a cycloalkyl group. In one embodiment, the cycloalkyl group is a cyclopropane.

In one embodiment, $R^d$ is selected from the group consisting of hydrogen, alkyl, and cycloalkyl.

In one embodiment, $R^e$ is selected from the group consisting of hydrogen and alkyl.

In one embodiment, at least one of $X^1$, $X^2$, $X^3$, $X^4$, $X^5$, $X^6$, and $X^7$ is not null.

In one embodiment, chain

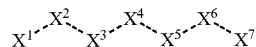

is selected from the group consisting of

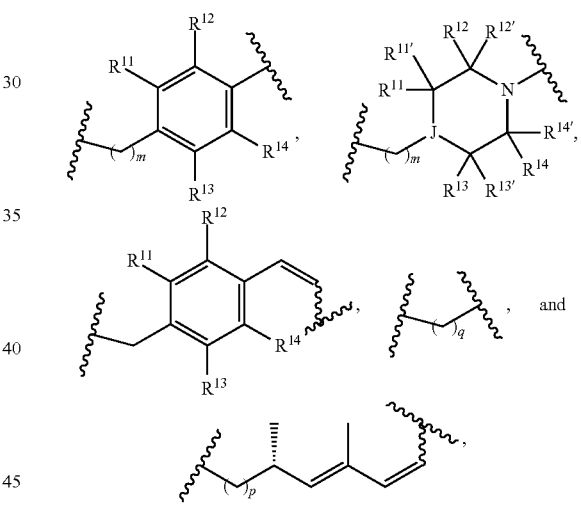

wherein $R^{11}$, $R^{12}$, $R^{13}$, $R^{14}$, and $R^{14'}$ are each independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and S(=O)$_2$NR$^d$R$^e$, and wherein each R$^d$, R$^e$ and R$^f$ is independently selected from the group consisting of H and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of R$^d$, R$^e$ or R$^f$ can optionally be joined to form additional rings; and any of R$^{11}$, R$^{12}$, R$^{13}$, R$^{14}$, and R$^{14'}$ can optionally be connected to each other to form various carbocyclic or heterocyclic rings;

m is an integer from 0 to 3;

q is an integer from 0 to 7;

p is an integer from 0 to 2; and

J is selected from the group consisting of CH and N.

In one embodiment, the compound is a compound of Formula I-A. In another embodiment, the compound is a compound of Formula I-B.

In one embodiment, the compound is selected from the group consisting of Formulae VI-A, VII-A, VIII-A, IX-A, X-A, VI-B, VII-B, VIII-B, IX-B, and X-B, or a salt or solvate thereof:

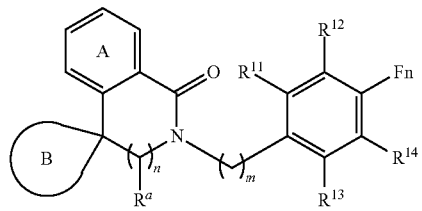

Formula VI-A

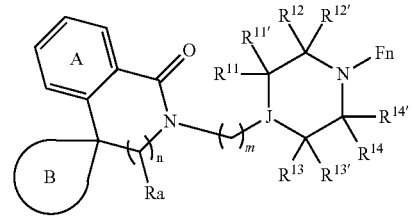

Formula VII-A

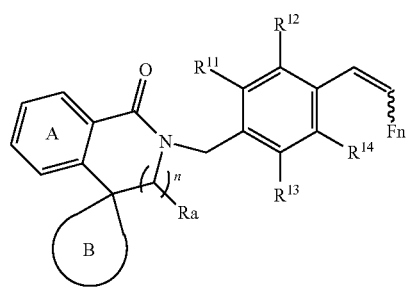

Formula VIII-A

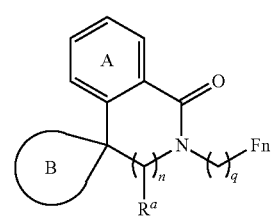

Formula IX-A

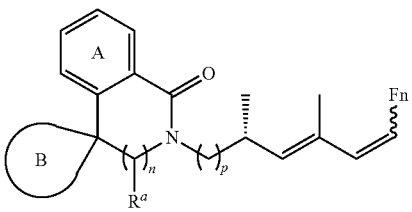

Formula X-A

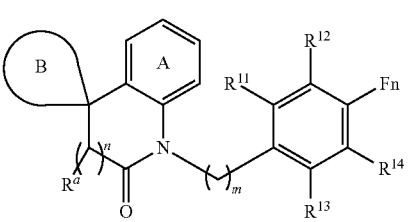

Formula VI-B

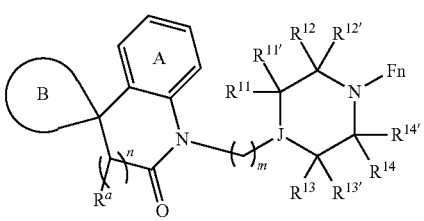

Formula VII-B

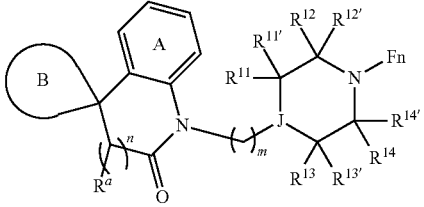

Formula VIII-B

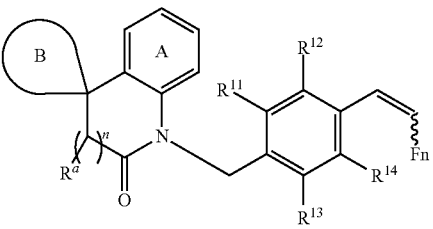

Formula IX-B

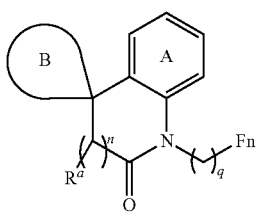

Formula X-B

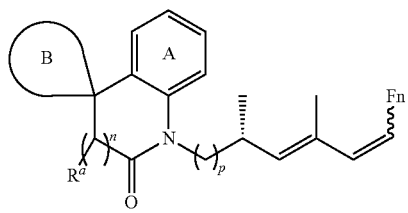

wherein in Formulae VI-A to X-B:

R$^{11}$, R$^{12}$, R$^{13}$, R$^{14}$, and R$^{14'}$ are each independently selected from the group consisting of H, F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein each $R^d$, $R^e$ and $R^f$ is independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ can optionally be joined to form additional rings; and any of $R^{11}$, $R^{12}$, $R^{13}$, $R^{14}$, and $R^{14'}$ can optionally be joined to each other to form various carbocyclic or heterocyclic rings e.g. if $R^{12}$ is $CH_2$ and $R^{13}$ is $OCH_2$, they can join to form a bridged tetrahydrofuran ring, etc.;

m is an integer from 0 to 3;

q is an integer from 0 to 7;

p is an integer from 0 to 2;

J is selected from the group consisting of CH and N; and

Fn is selected from the group consisting of Formulae II, III, IV and V:

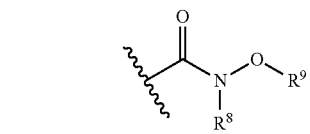

Formula II

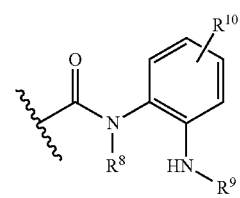

Formula III

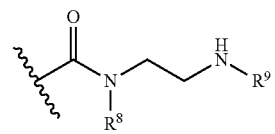

Formula IV

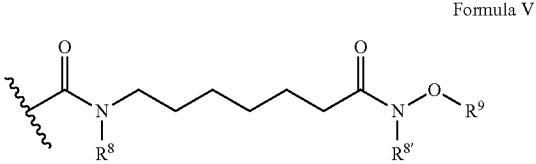

Formula V wherein in Formulae II, III, IV and V:

$R^8$, $R^{8'}$, $R^9$, and $R^{10}$ are each independently selected from the group consisting of null, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution.

In one embodiment, the compound has a chemical structure that contains isotope atoms D, $^{13}C$, and $^{19}F$.

In one embodiment, the compound of Formulae VI-A, VII-A, VIII-A, IX-A, and X-A, VI-B, VII-B, VIII-B, IX-B, or X-B is selected from the group consisting of:

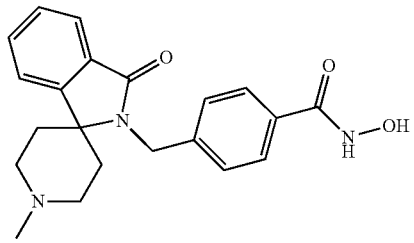

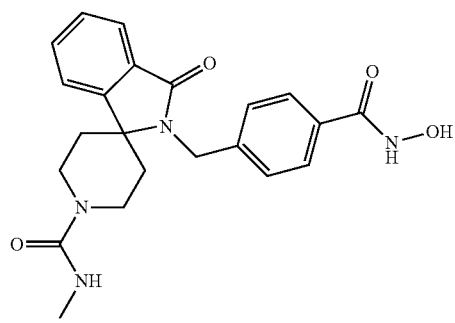

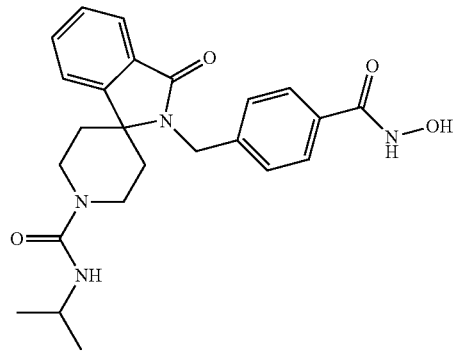

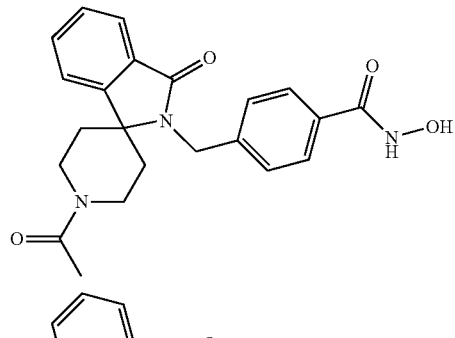

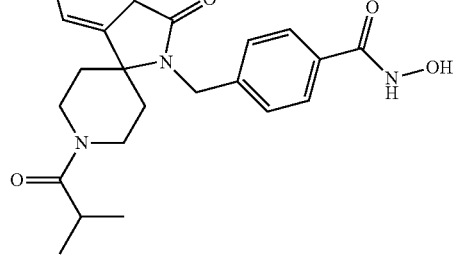

45
-continued
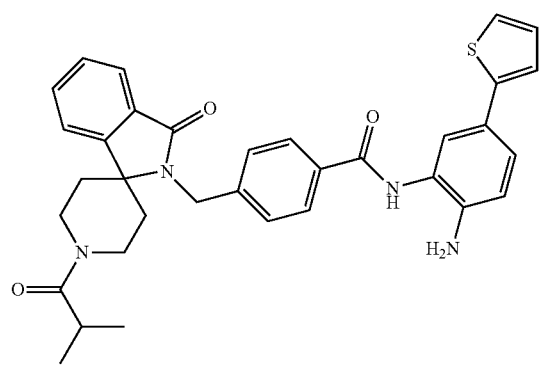
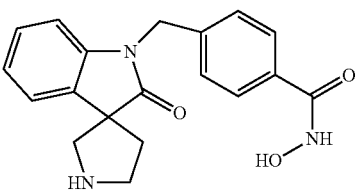
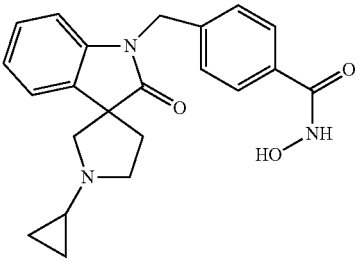
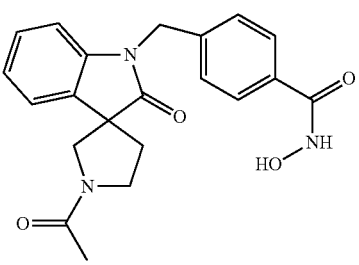
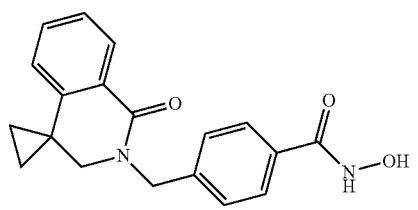
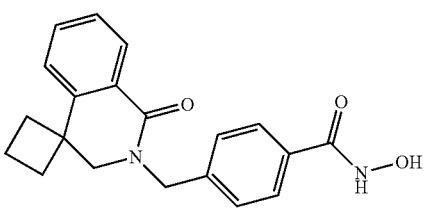
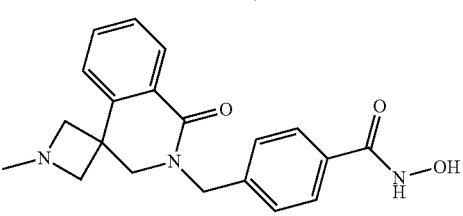
46
-continued
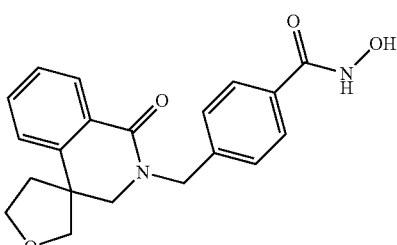
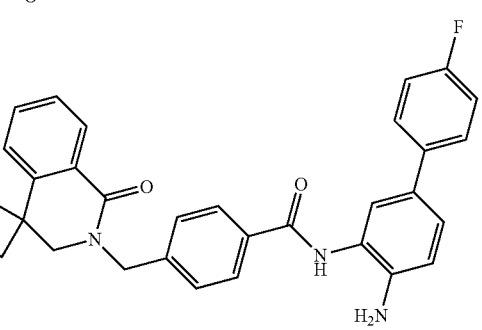
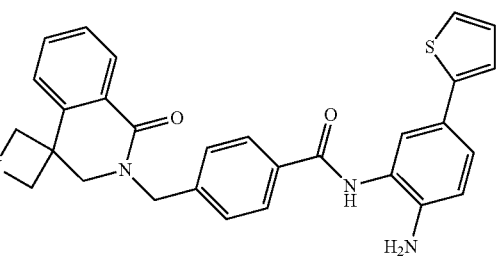
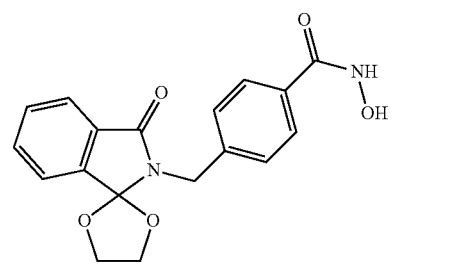
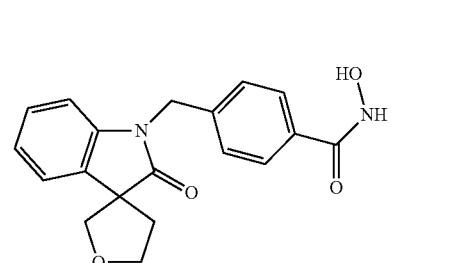
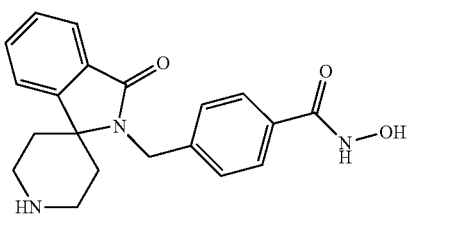

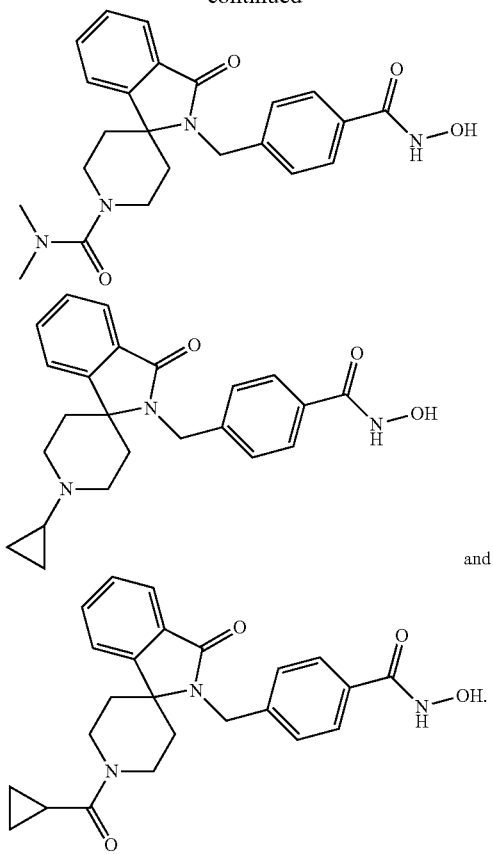

and

Formulations, Prodrugs, and Salts

In one embodiment, the invention provides use of the compounds of the invention for the manufacture and preparation of medicaments for use in therapy. In one embodiment, the present invention provides compounds of useful for the manufacture and preparation of medicaments for use in treating and preventing diseases and disorders. In one embodiment, the diseases or disorders are associated with HDAC. In one embodiment, an effective inhibitor of HDACs retains its activity when mixed with an acceptable pharmaceutical carrier. In one embodiment, the invention further provides novel compounds and novel pharmaceutical compositions comprising the same and at least one pharmaceutically acceptable carrier.

The invention includes prodrugs of the compounds of the invention. "Prodrug," as used herein, means a compound which is convertible in vivo by metabolic means (e.g., by hydrolysis) to a compound of the present invention. Various forms of prodrugs are known in the art, for example, as discussed in Bundgaard, (ed.), Design of Prodrugs, Elsevier (1985); Widder et al. (ed.), Methods in Enzymology, vol. 4, Academic Press (1985); Krogsgaard-Larsen et al. (ed). "Design and Application of Prodrugs," Textbook of Drug Design and Development, Chapter 5, 113-191 (1991), Bundgaard et al., 1992, J. Drug Deliv. Rev. 8:1-38, Bundgaard, 1988, J. Pharm. Sci. 77:285 et seq.; and Higuchi and Stella (eds.), Prodrugs as Novel Drug Delivery Systems, American Chemical Society (1975). In one non-limiting example, the esters and amides of the alpha-carboxylic acid are prepared as prodrugs to improve oral bioavailability, whereby the ester or amide is stable in the stomach and gastrointestinal tract, is optimally transported across the lining of the gastrointestinal tract into the bloodstream, and is then converted by the ubiquitous esterases or amidases in the blood to the carboxylic acid moiety. In another non-limiting example, the ester prodrug is the methyl, ethyl, n-propyl or i-propyl ester. In another non-limiting example, the amide prodrug is the isopropyl amide or the 2,2,2-trifluoroethyl amide.

The compounds useful in the invention may form salts with acids or bases, and such salts are included in the present invention. In one embodiment, the salts are pharmaceutically-acceptable salts. The term "salts" embraces addition salts of free acids or free bases that are compounds useful within the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds useful in the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base with the compound.

Methods of the Invention

In one aspect, the present invention includes methods for inhibiting HDACs. In one embodiment, the invention includes methods for treating, in a subject, a disease or disorder associated with HDACs. In one embodiment, the invention includes methods for inhibiting HDACs in a subject in need thereof. In one embodiment, the method includes administering a compound of the invention to the subject. In one embodiment, the subject is a human. In one embodiment, the subject has a disease or disorder selected from the group consisting of cancer, a psychiatric disease or disorder, a neurologic disease or disorder, a neurodegenerative disease or disorder, and a neuroinflammation disease or disorder.

In one embodiment, the invention includes a method of preventing or treating a disease or disorder, comprising administering a compound of the invention to a subject in need of such prevention or treatment, wherein the amount of the compound is sufficient for the prevention or treatment of the disease or disorder in the subject.

In one aspect, the present invention also includes methods for treating a disease or disorder associated with HDACs in a subject in need thereof. In one embodiment, the subject is a human. In one embodiment, the method includes administering a compound of the invention to the subject.

In one embodiment, the amount of the compound administered is sufficient for the prevention or treatment of the disease or disorder in the subject.

In one embodiment, the method comprises administering to the subject a therapeutically effective amount of a compound of the invention. In one embodiment, the compound is a compound of Formula I, or a salt or solvate thereof. In one embodiment, the compound is a compound of Formula I-A or Formula I-B, or a salt or solvate thereof. In one embodiment, the compound is a compound of Formula I-A, or a salt or solvate thereof. In one embodiment, the compound is a compound of Formula I-B, or a salt or solvate thereof. In one embodiment, the compound of Formula I-A has a structure selected from the group consisting of Formulae VI-A, VII-A, VIII-A, IX-A, and X-A, or a salt or solvate thereof. In one embodiment, the compound of Formula I-B has a structure selected from the group consisting of Formulae VI-B, VII-B, VIII-B, IX-B, and X-B, or a salt or solvate thereof.

In one aspect, the invention relates to a composition comprising a compound of the invention, or a salt or solvate thereof, and at least one pharmaceutically acceptable carrier.

In one aspect, the invention relates to a method of inhibiting HDAC. In one embodiment, the compound of the invention inhibits two or more HDACs. In another embodiment, the compound of the invention inhibits at least one HDAC. In another embodiment, the compound of the invention inhibits only a small group of HDACs. In another embodiment, the compound of the invention inhibits only one class of HDACs. In one embodiment, the compound of the invention selectively inhibits class I HDACs. In another embodiment, the compound of the invention selectively inhibits class IIA HDACs. In another embodiment, the compound of the invention selectively inhibits class IIB HDACs. In another embodiment, the compound of the invention selectively inhibits class III HDACs. In yet another embodiment, the compound of the invention selectively inhibits class IV HDACs.

In one embodiment, the compound of the invention selectively inhibits only part of a class of HDACs. In one embodiment, the compound of the invention inhibits only one HDAC. In one embodiment, the compound of the invention selectively inhibits HDAC1. In one embodiment, the compound of the invention selectively inhibits HDAC2. In one embodiment, the compound of the invention selectively inhibits HDAC3. In one embodiment, the compound of the invention selectively inhibits HDAC4. In one embodiment, the compound of the invention selectively inhibits HDAC5. In one embodiment, the compound of the invention selectively inhibits HDAC6. In one embodiment, the compound of the invention selectively inhibits HDAC7. In one embodiment, the compound of the invention selectively inhibits HDAC8. In one embodiment, the compound of the invention selectively inhibits HDAC9. In one embodiment, the compound of the invention selectively inhibits HDAC10. In one embodiment, the compound of the invention selectively inhibits HDAC11.

In one aspect, the invention relates to a method of inhibiting SIRT. In one embodiment, the compound of the invention inhibits two or more SIRTs. In one embodiment, the compound of the invention inhibits at least one SIRT. In one embodiment, the compound of the invention inhibits only one SIRT. In one embodiment, the compound of the invention selectively inhibits SIRT1. In one embodiment, the compound of the invention selectively inhibits SIRT2. In one embodiment, the compound of the invention selectively inhibits SIRT3. In one embodiment, the compound of the invention selectively inhibits SIRT4. In one embodiment, the compound of the invention selectively inhibits SIRT5. In one embodiment, the compound of the invention selectively inhibits SIRT6. In one embodiment, the compound of the invention selectively inhibits SIRT7.

In one embodiment, the invention provides a method of treating HDAC-associated diseases and disorders. In one embodiment, the method includes administering to a patient a therapeutically effective amount of a compound of the invention. In one embodiment, the invention provides a method of treating a disease or disorder related to the enzymatic control of the acetylation state of protein lysine residues, more specifically those contained in the N-terminal extensions of the core histones. In one embodiment, invention provides a method of treating a disease or disorder associated with the overexpression of one or more HDACs. In one embodiment, the disease or disorder is cancer, such as, but not limited to, multiple myeloma, leukemia, lymphoma, breast cancer, lung cancer, stomach cancer, liver cancer, blood cancer, bone cancer, pancreatic cancer, skin cancer, head or neck cancer, skin or eye melanoma, sarcoma of the uterus, ovarian cancer, rectal cancer, anal cancer, colorectal cancer, fallopian tube carcinoma, endometrium carcinoma, cervical cancer, small intestine cancer, endocrine gland cancer, thyroid cancer, parathyroid gland cancer, renal cell carcinoma, soft tissue sarcoma, urethra cancer, prostate cancer, bronchial cancer, myeloma, neuroma, cutaneous squamous cell carcinoma, or the like.

In one aspect, the invention provides a method of treating a disease or disorder selected from the group consisting of cancer, a psychiatric disease or disorder, a neurologic disease or disorder, a neurodegenerative disease or disorder, and a neuroinflammation disease or disorder. In one embodiment, the method includes administering to a patient a therapeutically effective amount of a compound of the invention.

In one aspect, the invention provides a method of treating a neurological disease or disorder. In one embodiment, the invention provides a method of treating an inflammatory disease or disorder. In other various embodiments, the diseases and disorders include, but are not limited to, diseases and disorders related to cell migration, cell spreading, immune synapse formation, viral infection, the degradation of misfolded proteins and stress granule (SG) formation. In one embodiment, the disease or disorder is Alzheimer's disease. In one embodiment, the disease or disorder is an autoimmune disease or disorder. In other various embodiments, the diseases and disorders treatable by the compound of the invention include, but are not limited to, diseases and disorders related to neurological disease, a neurodegenerative disorder, a neurodegenerative disease, neuroinflammation, pain, epilepsy, stroke, traumatic brain injury, allograft rejection, or a parasite related disease. In one embodiment, the neuroinflammation disease or disorder is the Charcot-Marie-Tooth (CMT) disease. In other embodiments, a disease or disorder is Huntington's disease, Parkinson's disease, ischemic stroke, amyotrophic lateral sclerosis (ALS) and spinal muscular atrophy, pain, anxiety and depression, bone and muscle-related disorders such as cancer-induced cachexia, Gaucher's disease, and neuroblastoma.

In one embodiment, the disease or disorder is a pathological autoimmune disorder such as juvenile oligoarthritis, collagen-induced arthritis, adjuvant-induced arthritis, Sjogren's syndrome, multiple sclerosis, experimental autoimmune encephalomyelitis, inflammatory bowel disease (for example, Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like.

In another aspect, the invention provides a method of immunomodulation for organ transplant. In one embodiment, the method includes administering to a patient a therapeutically effective amount of a compound of the invention. In one embodiment, the method confers improved or superior retention of organ transplants.

In one embodiment of the method of the invention, the compound of the invention is administered in combination with a second therapeutic agent for the treatment of a disease or disorder. In one embodiment, the second therapeutic agent is administered simultaneously, prior to, or after administration of the compound of the invention. In yet another embodiment, the second therapeutic agent is co-administered with the compound of the invention. In one embodiment, the second therapeutic agent is co-administered and co-formulated with the compound of the invention. In one embodiment, the second therapeutic agent is a DNA-damaging chemotherapeutics such as idarubicin and cytarabine for the treatment of AML and MDS. In one embodiment, the second therapeutic agent is a proteasome inhibitor such as bortezomib for the treatment of relapsing and/or refractory multiple myeloma and lymphoma. In another embodiment, the second therapeutic agent is an anti-androgen receptor agent such as bicalutamide for the treatment of prostate cancer.

In some embodiments, one or more additional pharmaceutical agents can be used, such as, for example, immunomodulatory or immunotherapeutic drugs, such as immune checkpoint inhibitor monoclonal antibodies, thalidomide, lenalidomide (Len) and pomalidomide, steroids, such as dexamethasone, anticancer antibodies, such as nivolumab and ipilimumab, proteasome inhibitors, such as bortezomib, salinosporamide, anticancer drugs, such as romidepsin, and taxanes, oncolytic viral therapy agents, such as adenovirus, reovirus, or herpes simplex.

In one embodiment, the second therapeutic agent is a DNA-damaging chemotherapeutics such as idarubicin and cytarabine for the treatment of AML and MDS. In one embodiment, the second therapeutic agent is a proteasome inhibitor such as bortezomib for the treatment of relapsing and/or refractory multiple myeloma and lymphoma. In one embodiment, the second therapeutic agent is an antiandrogen receptor agent such as bicalutamide for the treatment of prostate cancer.

In some embodiments, the second therapeutic agent is an antiretroviral drug. In other embodiments, the second therapeutic agent is a reverse-transcriptase inhibitor. In other embodiments, the second therapeutic agent can be lamivudine, zidovudine, lopinavir, ritonavir, abacavir, tenofovir, emtricitabine, rilpivirine, efavirenz, elvitegravir, cobicistat, dolutegravir, darunavir, atazanavir, and raltegravir.

In some embodiments, the compound of the invention may be administered to a subject in conjunction with (e.g., before, simultaneously, or following) any number of relevant treatment modalities including chemotherapy, such as kinase inhibitors Afatinib, Neratiniab, Lapatinib etc., radiation, immunosuppressive agents, immunomodulators, such as cyclosporin, azathioprine, methotrexate, mycophenolate, Pomalidomide, Lenalidomide and FK506, antibodies, or other immunoablative agents such as CAM PATH, anti-CD3 antibodies, agents targeting programmed death receptor-1 (PD-1) and ligand (PD-L1) or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993; Booth et al, 2017 Oncotarget, 8:90262-90277). In a further embodiment, the compounds of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the compounds of the present invention are administered following B-cell ablative therapy such as agents that react with CD20, e.g., Rituxan.

Without wishing to be bound by any particular theory, it is believed that the ability of the compounds of the invention to regulate the biological activity of HDACs provides methods of treating HDACs related disorders. For example, the compounds of the invention can be used to suppress HDACs activity, whether HDACs are overexpressed or not.

Dosing

The compounds of the invention, alone or in combination with another therapeutic agent, can be administered to a cell, a tissue, or a subject to provide a therapeutic effect. Methods for the safe and effective administration of the compounds of the invention are known to those skilled in the art. For instance, the administration of HDACs inhibitors is described in the literature.

Dosages of the compounds of the invention range from about 0.1 µg/day to 10,000 mg/day, from about 1 µg/day to 1000 mg/day, and from about 10 µg/day to 100 mg/day, and any and all whole or partial increments there between.

Stated in terms of subject body weight, dosages range from about 0.1 µg/kg/day to about 1000 mg/kg/day, from about 10 µg/kg/day to about 500 mg/kg/day, from about 20 µg/kg/day to about 100 mg/kg/day, from about 50 µg/kg/day to about 50 mg/kg/day, and from about 0.10 mg/kg/day to about 5 mg/kg/day, and any and all whole or partial increments there between.

Oral dosages of the compounds of the invention range from about 0.1 µg/day to about 10,000 mg/day, from about 1 µg/day to about 1000 mg/day, from about 10 µg/day to about 100 mg/day, and from about 8 mg/day to about 80 mg/day, and any and all whole or partial increments there between.

Stated in terms of subject body weight, oral dosages range from about 0.1 µg/kg/day to about 1000 mg/kg/day, from about 10 µg/kg/day to about 500 mg/kg/day, from about 20 µg/kg/day to about 100 mg/kg/day, from about 50 µg/kg/day to about 50 mg/kg/day, and from about 0.10 mg/kg/day to about 5 mg/kg/day, and any and all whole or partial increments there between.

The compounds of the invention for administration can be administered in a dose range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 μg to about 3,500 mg, about 5 μg to about 3,000 mg, about 10 μg to about 2,600 mg, about 20 μg to about 2,575 mg, about 30 μg to about 2,550 mg, about 40 μg to about 2,500 mg, about 50 μg to about 2,475 mg, about 100 μg to about 2,450 mg, about 200 μg to about 2,425 mg, about 300 μg to about 2,000, about 400 μg to about 1,175 mg, about 500 μg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, and any and all whole or partial increments there between.

In some embodiments, the dose of the compound of the invention is from about 0.0001 mg to about 25 mg. In some embodiments, a dose of a compound of the invention used in compositions described herein is less than about 100 mg, or less than about 80 mg, or less than about 60 mg, or less than about 50 mg, or less than about 30 mg, or less than about 20 mg, or less than about 10 mg, or less than about 5 mg, or less than about 2 mg, or less than about 0.5 mg. Similarly, in some embodiments, a dose of a second compound as described herein is less than about 1000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments there between.

Enantiomeric or Diastereomeric Forms, and Isotope Substitutions.

It will be understood that when compounds of the invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention that are efficacious in inhibiting HDACs. The isomers resulting from the presence of a chiral center comprise a pair of non-superimposable isomers that are called "enantiomers." Single enantiomers of a pure compound are optically active, i.e., they are capable of rotating the plane of plane polarized light. Enantiomers may be purified from racemic mixtures by well-known chiral separation techniques. According to one such method, a racemic mixture of a compound having the structure of Formula I or a chiral intermediate thereof, is separated into 99% wt % pure optical isomers by HPLC using a suitable chiral column, such as a member of the series of DAICEL® CHIRALPAK® family of columns (Daicel Chemical Industries, Ltd., Tokyo, Japan), operated according to the manufacturer's instructions. By "isolated optical isomer" it is understood a compound that has been substantially purified from the corresponding optical isomer(s) of the same formula. In some embodiments, the isolated isomer is at least about 80% pure by weight. In some embodiments, the isolated isomer is at least about 90% pure by weight. In some embodiments, the isolated isomer is at least about 98% pure by weight. In some embodiments, the isolated isomer is at least about 99% pure, by weight. Diastereoisomeric pairs may be resolved by known separation techniques including normal and reverse phase chromatography, and crystallization.

Isotopic substitutions can be applied to compounds of the invention. Isotope atoms include but not limited to D and T for substitution of H; $C^{13}$ for $C^{12}$; or $F^{19}$ for $F^{18}$.

Pharmaceutical Composition

For administration of a compound of the present invention to a subject, the compound can be suspended in any pharmaceutically acceptable carrier, for example, sterile water or buffered aqueous carriers, such as glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference as if set forth in its entirety herein.

The pharmaceutical compositions comprising a compound of the invention may be prepared, packaged, or sold in the form of a sterile injectable aqueous or oily suspension or solution. This suspension or solution may be formulated according to the known art, and may comprise, in addition to the active ingredient, additional ingredients such as dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

The compositions of the invention are preferably administered to the subject as a pharmaceutical or veterinary composition, which includes systemic and topical formulations. Among these, preferred are formulations suitable for inhalation, or for respirable, buccal, oral, rectal, vaginal, nasal, intrapulmonary, ophthalmic, optical, intracavitary, intratracheal, intraorgan, topical (including buccal, sublingual, dermal and intraocular), parenteral (including subcutaneous, intradermal, intramuscular, intravenous and intraarticular) and transdermal administration, among others. The route(s) of administration will be readily apparent to the skilled artisan and will depend upon any number of factors including the type and severity of the disease being treated, the type and age of the veterinary or human patient being treated.

The compositions of the invention may be administered to the lungs of a subject by any suitable means, but are preferably administered by generating an aerosol or spray comprised of respirable, inhalable, nasal or intrapulmonarily delivered particles comprising the active compound, which particles the subject inhales, i.e., by inhalation administration. The respirable particles may be liquid or solid. Particles comprising the active compound for practicing the present invention should include particles of respirable or inhalable size; that is, particles of a size sufficiently small to pass through the mouth and larynx upon inhalation and into the bronchi and alveoli of the lungs. In general, particles ranging from about 0.05, about 0.1, about 0.5, about 1, about 1.5 to about 5, about 6, about 7, about 8, about 10 microns in size, more particularly particles about 0.5 to less than about 5 microns in size, are respirable or inhalable. When particles of nonrespirable size are included in the aerosol or spray, they tend to deposit in the throat and be swallowed. Thus, the quantity of non-respirable particles in the aerosol or spray is preferably minimized when intended for respirable administration or by inhalation. For nasal or intrapulmonary administration, a particle size in the range of about 10, about 11, about 15, about 20 to about 25, about 30, about 40, about 50, and sometimes even up to about 100 and about 500 microns is preferred to ensure retention in the nasal or pulmonary cavity. Pulmonary instillation is particularly useful in treating newborns.

Liquid pharmaceutical compositions of the compound of the invention for producing an aerosol or spray may be prepared by combining the active compound with a stable vehicle, such as sterile pyrogen free water. Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant which serves to facilitate the formation of an aerosol. A suitable dispersant is lactose, which may be blended with the active compound in any suitable ratio, e.g., a 1 to 1 ratio by weight. Other therapeutic and formulation compounds may also be included, such as a surfactant to improve the state of surfactant in the lung and to help with the absorption of the active agent.

Aerosols of liquid particles comprising an active compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable compositions for use in nebulizer consist of the active ingredient in liquid carrier, the active ingredient comprising up to 40% w/w of the compositions, but preferably less than 20% w/w, and the carrier is typically water or a dilute aqueous alcoholic solution, preferably made isotonic with body fluids by the addition of, for example sodium chloride. Optional additives include preservatives if the composition is not prepared sterile, for example, methyl hydroxybenzoate, antioxidants, flavoring agents, volatile oils, buffering agents and surfactants.

Aerosols of solid particles comprising the active compound may likewise be produced with any sold particulate medicament aerosol generator. Aerosol generators for administering solid particulate medicaments to a subject produce particles which are respirable, as explained above, and they generate a volume of aerosol containing a predetermined metered dose of a medicament at a rate suitable for human administration. Examples of such aerosol generators include metered dose inhalers and insufflators.

Pharmaceutical compositions that are useful in the methods of the invention may be administered systemically in oral solid formulations, ophthalmic, suppository, aerosol, topical or other similar formulations. In addition to the compounds of the invention, or a biological equivalent thereof, such pharmaceutical compositions may contain pharmaceutically-acceptable carriers and other ingredients known to enhance and facilitate drug administration.

The pharmaceutical compositions described herein can be prepared alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

In yet another embodiment, compositions of the invention may be administered to the desired location of a subject by a transdermal patch. A transdermal patch is meant a system capable of delivery of a compound to a subject via the skin, or any suitable external surface, including mucosal membranes, such as those found inside the mouth. Such delivery systems generally comprise a flexible backing, an adhesive and a compound retaining matrix, the backing protecting the adhesive and matrix and the adhesive holding the whole on the skin of the subject. On contact with the skin, the compound-retaining matrix delivers the compound to the skin, the compound then passing through the skin into the subject's system.

Certain embodiments of the invention provide a pharmaceutical preparation/dosage formulation provided in the form of a transdermal patch and formulated for sustained release formulation, in a therapeutically effective amount sufficient to treat a disease associated with activation of an immune cell (e.g., rheumatoid arthritis) in a patient, wherein the dosage formulation, when administered (provided as a patch) to the patient, provides a substantially sustained dose over at least about 2 hours, 4 hours, 6 hours, 8, hours, 12 hours, 20 hours, or at least about 24 hours.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, bolus injections, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

A pharmaceutical composition of the invention may be prepared, packaged, or sold in a formulation suitable for pulmonary administration via the buccal cavity. Such a formulation may comprise dry particles that comprise the active ingredient and that have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful in pulmonary delivery are also useful in intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to a subject, preferably a human, will vary depending upon any number of factors, including but not limited to, the type of animal and type of disease state being treated, the age of the subject and the route of administration.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject, and the like.

Kit and Probes

In some embodiments, the present invention also includes pharmaceutical kits and/or research probes useful, for example, in the treatment or prevention of HDACs associated diseases or disorders such as cancer, neurodegenerative diseases and pathological autoimmune response. In one embodiment, the kit includes a compound of the present invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

In some embodiments, the present invention also includes probes comprising a compound of the invention, useful, for example, in the treatment or prevention of HDACs associated diseases or disorders such as cancer, neurodegenerative diseases and pathological autoimmune response, or in the imaging or theragnostics approaches to HDACs associated diseases or disorders such as cancer, neurodegenerative diseases and pathological autoimmune response. In one embodiment, a probe comprises a compound of the invention further conjugated to a radiolabeled moiety, a fluorescent labeled moiety, or biotin. Any numbers of linkers known in the art can be used for conjugation. In another embodiment, no linker is necessary for conjugation. In some embodiments, a conjugated probe including a compound of the invention is used for research, diagnostic and therapeutic purposes.

In one aspect, the invention provides methods comprising the use of theragnostics, or theranostics, further comprising a compound of the invention. Theragnostics, or theranostics, are compounds, formulations and compositions, capable of functioning as both therapeutic agents and diagnostic agents. For example, a probe of the invention can inhibit or modulate the activity of one or more HDACs, and at the same time provide for the possibility of imaging its distribution in a cell, tissue, organ, or entire body. Modern approaches to theragnostics, or theranostics, have been described by Xie et al., 2010, Adv Drug Deliv Rev, 62(11):1064-1079, and Pene et al., 2009, Crit Care Med., 37(1 Suppl):S50-8, descriptions incorporated herein in their entirety.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The experiments disclosed herein were designed to generate novel HDACs inhibitors, both pan-inhibitors of several or all classes of HDACs, and selective inhibitors between and/or within classes. These inhibitors can serve as novel therapeutic agents for HDACs related diseases and disorders. The materials and methods employed in these experiments are now described.

Example 1: Synthesis of Compounds of the Invention

The compounds of the invention can be prepared by a person skilled in the art of synthetic organic chemistry once armed with the teachings herein. The person skilled in the art knows how to select and implement appropriate synthetic routes. Suitable synthetic methods may be identified by reference to the literature describing synthesis of analogous compounds, and then performing the synthesis of the desired compound following the route used for the analogous compounds, modifying the starting materials, reagents, and reaction conditions as appropriate to synthesizing any particular desired compounds. In addition, reference may be made to sources such as Comprehensive Organic Synthesis, Ed. B. M. Trost and I. Fleming (Pergamon Press 1991), Comprehensive Organic Functional Group Transformations, Ed. A. R. Katritzky, O. Meth Cohn, and C. W. Rees (Pergamon Press, 1996), Comprehensive Organic Functional Group Transformations II, Ed. A. R. Katritzky and R. J. K. Taylor (Editor) (Elsevier, 2nd Edition, 2004), Comprehensive Heterocyclic Chemistry, Ed. A. R. Katritzky and C. W. Rees (Pergamon Press, 1984), and Comprehensive Heterocyclic Chemistry II, Ed. A. R. Katritzky, C. W. Rees, and E. F. V. Scriven (Pergamon Press, 1996), the entire disclosures of which are incorporated herein by reference.

In one embodiment of the invention, the starting materials and intermediates required for the synthesis may be obtained from commercial sources or synthesized according to methods known to those skilled in the art. In various embodiments, a compound of the invention can be synthesized according to Scheme 1, Scheme 2, Scheme 3, Scheme 4, or any variations thereof apparent to one skilled in the art.

Scheme 1

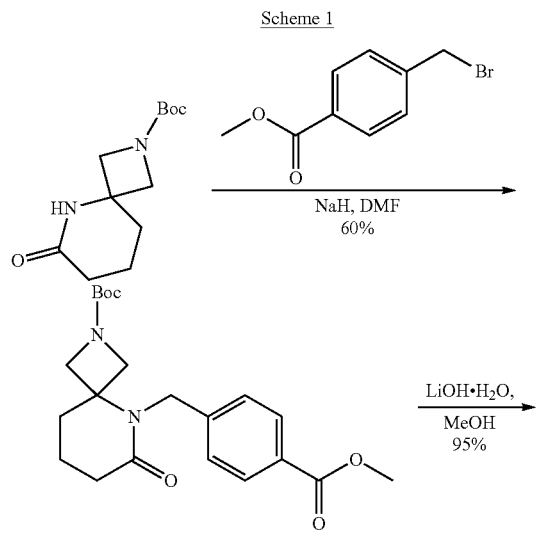

Scheme 2

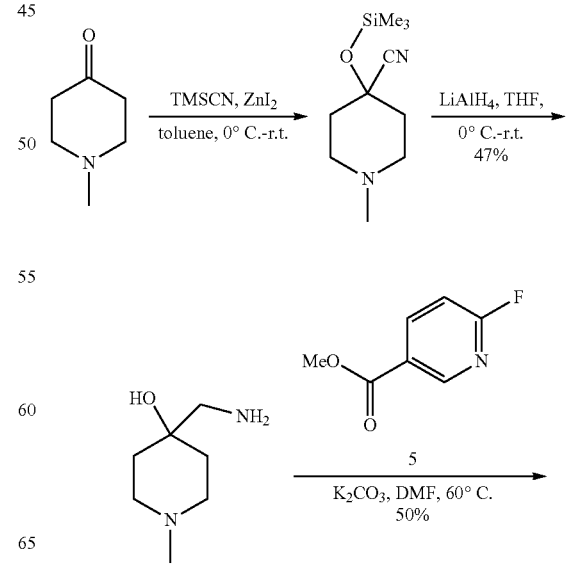

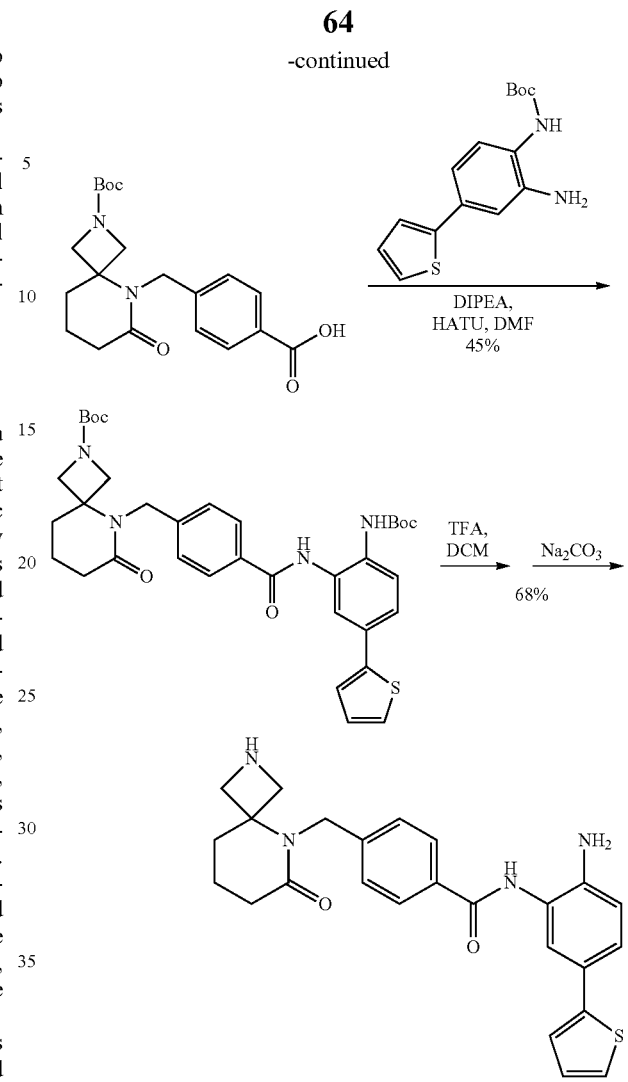

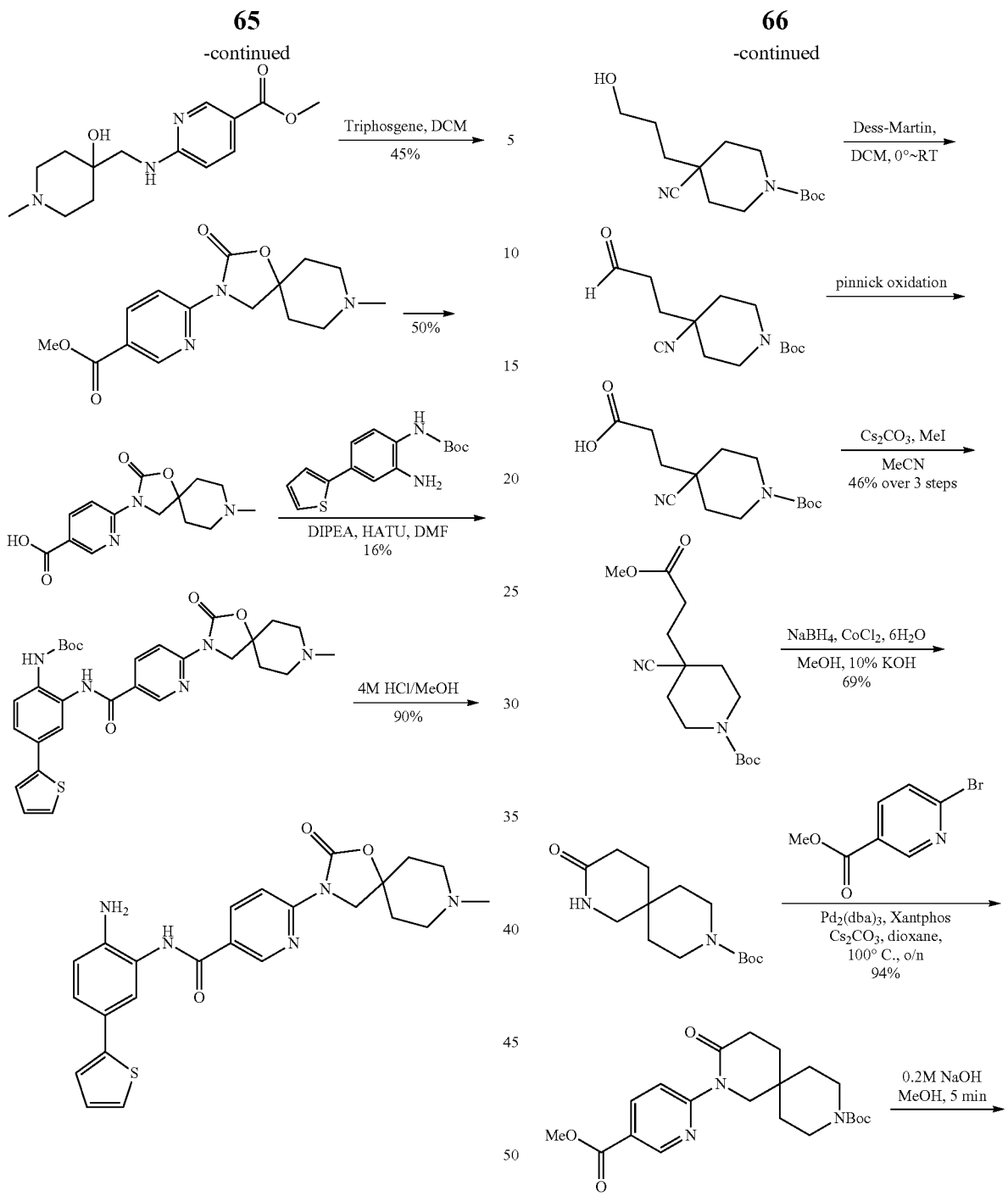
Scheme 3
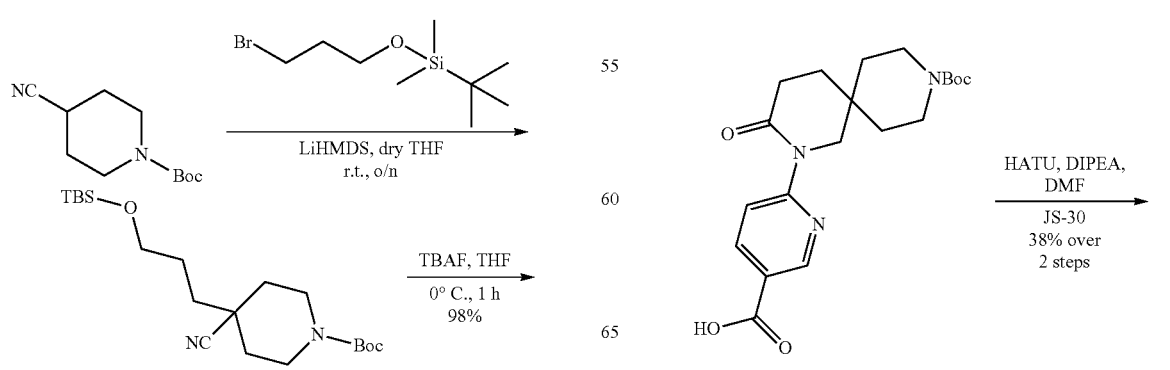

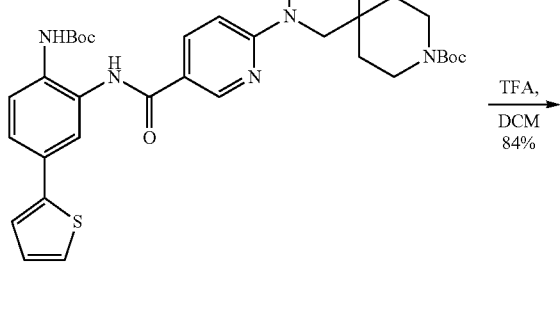

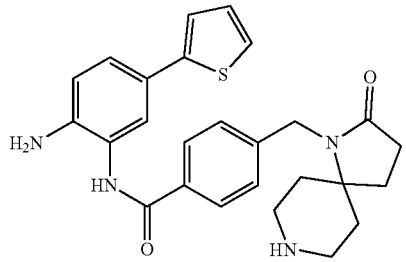 [SMILES: Nc1ccc(-c2cccs2)cc1NC(=O)c1ccc(CN2C(=O)CCC23CCNCC3)cc1]

TFA,
DCM
84%

Compound Example 2. N-(2-amino-5-(thiophen-2-yl)phenyl)-4-((2-oxo-1,8-diazaspiro[4.5]decan-1-yl)methyl)benzamide

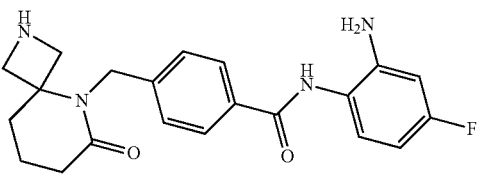 [SMILES: Nc1cc(F)ccc1NC(=O)c1ccc(CN2C(=O)CCCC23CNC3)cc1]

Compound Example 2 was synthesized according to Scheme 1. $^1$HNMR (DMSO-d6, 400 MHz): δ, 9.84 (s, 1H), 8.00 (d, J=8.0 Hz, 2H), 7.48 (s, 1H), 7.41 (d, =8.0 Hz, 2H), 7.35 (d, =4.8 Hz, 1H), 7.28-7.30 (m, 1H), 7.24 (d d, =3.2 Hz, 1H), 7.03-7.06 (m, 1H), 6.81 (d, =8.0 Hz, 1H), 5.20 (s, 2H). 4.43 (s, 2H), 3.13-3.16 (m, 2H), 2.84-2.90 (m, 2H), 2.40-2.44 (m, 2H), 2.12-2.20 (m, 2H), 2.03-2.07 (m, 2H), 1.42-1.45 (m, 2H). LC-MS showed a single peak with purity >95% based on UV absorption at 254 nm. MS: $C_{26}H_{28}N_4O_2S$. Calculated (M+H): 461, obtained MS: 461.

Compound Example 3. N-(2-amino-4-fluorophenyl)-4-((6-oxo-2,5-diazaspiro[3.5]nonan-5-yl)methyl)benzamide

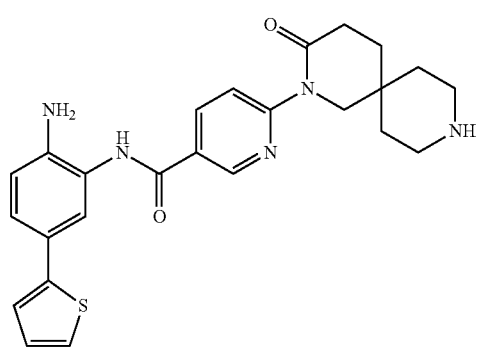

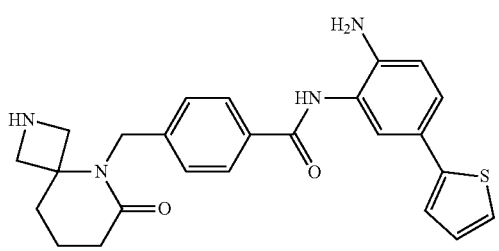

Compound Example 1. N-(2-amino-5-(thiophen-2-yl)phenyl)-4-((6-oxo-2,5-diazaspiro[3.5]nonan-5-yl)methyl)benzamide Compound Example 3 was synthesized according to Scheme 1. $^1$HNMR (400 MHz, DMSO-d6): δ 9.54 (s, 1H), 7.91 (d, J=8.0 Hz, 2H), 7.24 (d, J=8.0 Hz, 2H), 7.11 (t, J=7.4 Hz, 1H), 6.52-6.55 (dd, 1H), 6.35 (t, J=2.4 Hz, 1H), 5.22 (s, 2H), 4.93 (s, 2H), 3.68-3.71 (m, 2H), 3.27-3.34 (m, 4H), 2.38 (t, J=6.4 Hz, 2 Hz), 2.19-2.20 (m, 1H), 1.72-1.75 (m, 2H). LC-MS showed a single peak with purity >95% based on UV absorption at 254 nm. MS: $C_{21}H_{23}FN_4O_2$. Calculated (M+H): 383, obtained MS: 383.

Compound Example 4. N-(2-amino-5-(thiophen-2-yl)phenyl)-6-(8-methyl-2-oxo-1-oxa-3,8-diazaspiro[4.5]decan-3-yl)nicotinamide

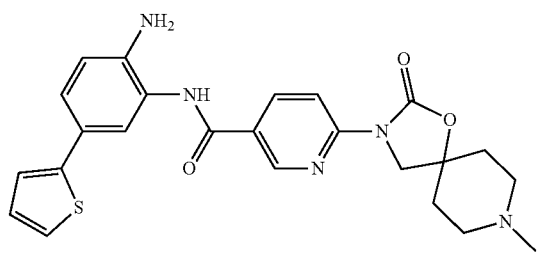 [SMILES: CN1CCC2(CC1)CN(c1ccc(C(=O)Nc3cc(-c4cccs4)ccc3N)cn1)C(=O)O2]

Compound Example 1 was synthesized according to Scheme 1. $^1$HNMR (400 MHz, DMSO-d6): δ 9.70 (s, 1H), 7.93 (d, J=8.0 Hz, 2H), 7.48 (s, 1H), 7.24-7.35 (m, 5H), 7.05 (m, 1H), 6.81 (d, J=8.4 Hz, 1H), 5.16 (s, 2H), 4.94 (s, 2H), 3.63 (d, J=7.6 Hz, 2H), 3.60 (d, J=7.6 Hz, 2H), 2.38 (t, J=6.4 Hz, 2H), 2.18 (m, 2H), 1.73 (m, 2H). LC-MS showed a single peak with purity >95% based on UV absorption at 254 nm. MS: $C_{25}H_{26}N_4O_2S$. Calculated (M+H): 447, obtained MS: 447.

Compound Example 4 was synthesized according to Scheme 2. ¹HNMR (400 MHz, 10% D2O in DMSO-d6): δ 8.99 (s, 1H), 8.44-8.42 (m, 1H), 8.24 (d, J=8.8 Hz, 1H), 7.61 (s, 1H), 7.54-7.52 (m, 1H), 7.48 (d, J=5.2 Hz, 1H), 7.42 (d, J=3.2 Hz, 1H), 7.18-7.13 (m, 2H), 4.25 (s, 0.6H), 4.13 (s, 1.4H), 3.50-3.47 (m, 2H), 3.29-3.18 (m, 2H), 2.86 (s, 3H), 2.37-2.30 (m, 2H), 2.20-2.13 (m, 2H). LC-MS showed a single peak with purity >95% based on UV absorption at 254 nm. MS: $C_{24}H_{25}N_5O_3S$. Calculated (M+H): 464, obtained MS: 464.

Compound Example 5. N-(4-amino-4'-fluoro-[1,1'-biphenyl]-3-yl)-6-(2-oxo-1,8-dioxa-3-azaspiro[4.5]decan-3-yl)nicotinamide

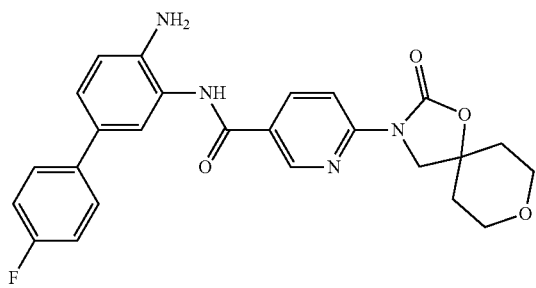 [SMILES: Nc1ccc(-c2ccc(F)cc2)cc1NC(=O)c1ccc(N2CC3(CCOCC3)OC2=O)nc1]

Compound Example 5 was synthesized according to Scheme 2. 1HNMR (400 MHz, DMSO-d6): δ 9.84 (s, 1H), 8.98 (s, 1H), 8.38-8.45 (m, 1H), 8.22 (s, 1H), 7.56-7.62 (m, 2H), 7.50 (d, J=0.42 Hz, 1H), 7.30-7.34 (m, 1H), 7.22 (t, J=8.80 Hz, 2H), 6.86 (d, J=8.40 Hz, 1H), 5.18 (s, 2H), 4.09 (s, 2H), 3.69-3.74 (m, 4H), 1.86-2.00 (m, 4H). LC-MS showed a single peak with purity >95% based on UV absorption at 254 nm. MS: $C_{25}H_{23}FN_4O_4$. Calculated (M+H): 463, obtained MS: 463.

Compound Example 6. N-(2-amino-5-(thiophen-2-yl)phenyl)-6-(3-oxo-2,9-diazaspiro[5.5]undecan-2-yl)nicotinamide

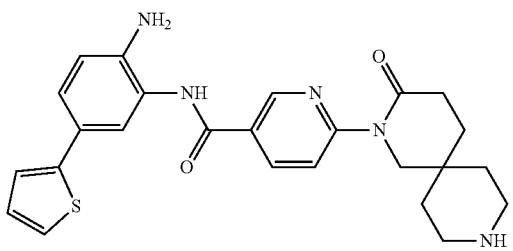 [SMILES: Nc1ccc(-c2cccs2)cc1NC(=O)c1ccc(N2CC3(CCNCC3)CCC2=O)nc1]

Compound Example 6 was synthesized according to Scheme 3. ¹H-NMR (400 MHz, CD3OD): δ 9.04 (s, 1H), 8.35 (dd, J=0.5, 2.2 Hz, 1H), 7.95 (d, J=2.1 Hz, 1H), 7.51 (d, J=0.2 Hz, 1H), 7.37 (dd, J=0.5, 2.1 Hz, 1H), 7.24 (m, 2H), 7.03 (t, J=1.0 Hz, 1H), 6.91 (d, J=2.1 Hz, 1H), 3.95 (s, 2H), 2.86 (m, 4H), 2.64 (t, J=1.7 Hz, 2H), 1.87 (t, J=1.8 Hz, 2H), 1.61 (t, J=1.5 Hz, 4H). LC-MS showed a single peak with purity >95% based on UV absorption at 254 nm. MS: $C_{25}H_{27}N_5O_2S$. Calculated (M+H): 462, obtained MS: 462.

Compound Example 7. N-(2-amino-4-fluorophenyl)-6-(3-oxo-2,9-diazaspiro[5.5]undecan-2-yl)nicotinamide

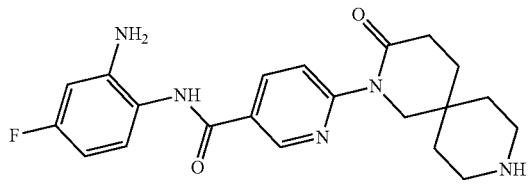 [SMILES: Nc1cc(F)ccc1NC(=O)c1ccc(N2CC3(CCNCC3)CCC2=O)nc1]

Compound Example 7 was synthesized according to Scheme 3. ¹H-NMR (400 MHz, CD3OD): δ 8.91 (s, 1H), 8.24 (dd, J=0.5, 2.2 Hz, 1H), 7.89 (m, 1H), 7.04 (dd, J=1.5, 2.2 Hz, 1H), 6.51 (dd, J=0.5, 2.7 Hz, 1H), 6.34 (dd, J=0.6, 2.1 Hz, 1H), 5.25 (t, J=1.2 Hz, 1H), 3.93 (m, 2H), 3.12 (m, 2H), 2.56 (t, J=1.7 Hz, 2H), 1.94 (m, 2H), 1.84 (t, J=1.8 Hz, 2H), 1.76 (t, J=1.5 Hz, 4H). LC-MS showed a single peak with purity >95% based on UV absorption at 254 nm. MS: $C_{21}H_{24}FN_5O_2$. Calculated (M+H): 398, obtained MS: 398.

Example 2: Dose Dependent Inhibition of HDAC Compounds Prepared in Enzymatic Assays The results described below demonstrate dose dependent inhibition of HDAC compounds prepared in enzymatic assays, and the IC50 values of synthesized and reference compounds in HDAC Enzymatic Assays. Incubation time for HDAC1/2 is 120 min, and 10 min for other HDACs.

Materials and Methods: Enzymes

Human HDAC1 (GenBank Accession No. NM_004964), full-length with a C-terminal His-tag and a C-terminal FLAG-tag, MW=56 kDa, was expressed in a baculovirus expression system.

Human HDAC2 (GenBank Accession No. NM_001527), full-length with a C-terminal His-tag, MW=56 kDa, was expressed in a baculovirus expression system.

Complex of human HDAC3 (GenBank Accession No. NM_003883), full-length with a C-terminal His tag, MW=49.7 kDa, and human NCOR2 (amino acid 395-489) (GenBank Accession No. NM_006312), N-terminal GST tag, MW=37.6 kDa, was co-expressed in a baculovirus expression system.

Human HDAC4 (GenBank Accession No. NM_006037), amino acids 627-1085 with a N-terminal GST tag, MW=75.2 kDa, was expressed in a baculovirus expression system.

Human HDAC5 (GenBank Accession No. NM_005474), full-length with an N-terminal GST tag, MW=150 kDa, was expressed in a baculovirus expression system.

Recombinant human HDAC6 (GenBank Accession No. BC069243), full-length, MW=180 kDa, was expressed by baculovirus in Sf9 insect cells using an N-terminal GST tag.

Human HDAC7 (GenBank Accession No. AY302468), (a.a. 518-end) with an N-terminal GST tag, MW=78 kDa, was expressed in a baculovirus expression system.

Human HDAC8 (GenBank Accession No. NM_018486), full-length with a C-terminal His tag, MW=46.4 kDa, was expressed in a baculovirus expression system.

Human HDAC9 (GenBank Accession No. NM_178423), amino acids 604-1066 with a C-terminal His tag, MW=50.7 kDa, was expressed in a baculovirus expression system.

Human HDAC10 (a.a. 1-481), GenBank Accession No. NM_032019 with a N-terminal GST tag and a C-terminal His tag, MW=78 kDa, was expressed in a baculovirus expression system.

Human HDAC11 (full length) (GenBank Accession No. NM_024827) with a N-terminal GST tag, MW=66 kDa, was expressed in a baculovirus expression system.

Human SIRT1 (Sirtuin 1, hSir2SIRT1)(GenBank Accession No. NM012238): Full length, MW=82 kDa, expressed in E. coli.

Human SIRT2 (Sirtuin 2, hSir2SIRT2) (GenBank Accession No. NM_012237): Full length, MW=43 kDa, expressed in E. coli.

Human SIRT3 (Sirtuin 3) (GenBank Accession No. NM_012239): Amino acids 102-399 (catalytically active), MW=32.7 kDa, expressed in E. coli.

Human SIRT5 (Sirtuin 5) (GenBank Accession No. NM_012241 (isoform 1); residues 37-310, MW=32.3 kDa) expressed in E. coli with an N-terminal His-tag).

The substrate RHKKAc-AMC, RHKAcKAc-AMC and AcK(trifluoroacetyl)-AMC were synthesized by Biomer.

ACY-1215, SAHA, Tubastatin A and Trichostatin A (TSA) was purchased from Selleckchem. TMP269 was purchased from MedKoo Biosciences. Nicotinamide adenine dinucleotide (NAD) was purchased from Tocris.

Materials and Methods: Biochemical Assay Procedure

I. Compound handling: Testing compounds were dissolved in 100% DMSO to a specific concentration. The serial dilution was conducted by epMotion 5070 in DMSO.

II. HDAC reaction buffer: 50 mM Tris-HCl, pH8.0, 137 mM NaCl, 2.7 mM KCl, and 1 mM MgCl2, Added fresh: 1 mg/ml BSA, 1% DMSO.

III. Substrate: Fluorogenic HDAC General Substrate for HDAC1, 2, 3, 6, 10, 11 ans Sirt1, 2 and 3: Arg-His-Lys-Lys(Ac); HDAC8 only substrate: Arg-His-Lys (Ac)-Lys(Ac); Class2A Substrate (HDAC4, 5, 7 and 9): Acetyl-Lys(trifluoroacetyl)-AMC; Sirt5 substrate: Ac-Lys(succinyl)-AMC.

IV. General Reaction Procedure: (Standard IC50 determination)
   a. Delivered 2× enzyme in wells of reaction plate except No Enzyme (No En) control wells. Add buffer in No En wells.
   b. Delivered compounds in 100% DMSO into the enzyme mixture by Acoustic technology (Echo550; nanoliter range). Spin down and pre-incubation.
   c. Delivered 2× Substrate Mixture (Fluorogenic HDAC Substrate and co-factor (500 µM of Nicotinamide adenine dinucleotide (NAD$^+$) in all Sirt assay) in all reaction wells to initiate the reaction. Spin and shake.
   d. Incubated for 1-2 hr. at 30° C. with seal.
   e. Added Developer with Trichostatin A (or TMP269 or NAD$^+$) to stop the reaction and to generate fluorescent color.
   f. Fluorescence was read (excitatory, 360; emission, 460) using the EnVision Multilabel Plate Reader (Perkin Elmer)
   g. Endpoint reading was taken for analysis after the development reaches plateau.

V. Data Analysis: The percentages of enzyme activity (relative to DMSO controls) and IC50 values were calculated using the GraphPad Prism 4 program based on a sigmoidal dose-response equation.

The inhibitory activities of HDAC of compounds of the invention were determined using biochemical HDAC assays. The data are summarized in the Table 1. Compounds were tested at the indicated doses in the biochemical assays of HDAC1, HDAC2, HDAC3, HDAC4, HDAC5, HDAC6, HDAC7, HDAC8, HDAC9, HDAC10, or HDAC11 enzyme. The curve fit and IC50 values were calculated using the GraphPad Prism 4 program based on a sigmoidal dose-response equation.

TABLE 1

Biochemical HDAC assays data for selected compounds.

| cmpd | HDAC1 (µM) | HDAC2 (µM) | HDAC3 (µM) | HDAC6 (µM) | HDAC8 (µM) |
|---|---|---|---|---|---|
| Example 1 Hd | 0.006 | 0.06 | 13 | >20 | >20 |
| Example 2 F4 | 0.014 | 0.146 | >20 | >20 | >20 |
| Example 3 He | 20 | 11.8 | 1.9 | >10 | >10 |
| Example 4 Fa | 0.007 | 0.064 | 17.4 | >20 | >20 |
| Example 5 Fb | 0.023 | 0.115 | >20 | >20 | >20 |
| Example 6 F1 | 0.085 | 0.61 | >20 | >20 | >20 |

Example 3: Modulation of a-Tubulin Acetylation by Compound Example 1 and Compound Example 4 in PC-3 Cells PC-3 cells were treated with the indicated concentrations of Compounds Example 1 and Example 4 or 24 hours as depicted in FIG. 1. The whole cell lysates were subjected to Western blot analyses with anti-Acetylated-tubulin antibody. The blots were then re-probed with anti-alpha-tubulin antibody. FIG. 1 depicts an image of the Western blot.

Example 4: Synthesis of Compounds of Formulae I-A and I-B

The compounds of the invention can be prepared by a person skilled in the art of synthetic organic chemistry once armed with the teachings herein. The person skilled in the art knows how to select and implement appropriate synthetic routes. Suitable synthetic methods may be identified by reference to the literature describing synthesis of analogous compounds, and then performing the synthesis of the desired compound following the route used for the analogous compounds, modifying the starting materials, reagents, and reaction conditions as appropriate to synthesizing any particular desired compounds. In addition, reference may be made to sources such as Comprehensive Organic Synthesis, Ed. B. M. Trost and I. Fleming (Pergamon Press 1991), Comprehensive Organic Functional Group Transformations, Ed. A. R. Katritzky, O. Meth Cohn, and C. W. Rees (Pergamon Press, 1996), Comprehensive Organic Functional Group Transformations II, Ed. A. R. Katritzky and R. J. K. Taylor (Editor) (Elsevier, 2nd Edition, 2004), Comprehensive Heterocyclic Chemistry, Ed. A. R. Katritzky and C. W. Rees (Pergamon Press, 1984), and Comprehensive Heterocyclic Chemistry II, Ed. A. R. Katritzky, C. W. Rees, and E. F. V. Scriven (Pergamon Press, 1996), the entire disclosures of which are incorporated herein by reference.

In one embodiment of the invention, the starting materials and intermediates required for the synthesis may be obtained from commercial sources or synthesized according to methods known to those skilled in the art. In various embodiments, a compound of the invention can be synthesized according to Scheme 5, Scheme 6, Scheme 7, Scheme 8, or any variations thereof apparent to one skilled in the art.
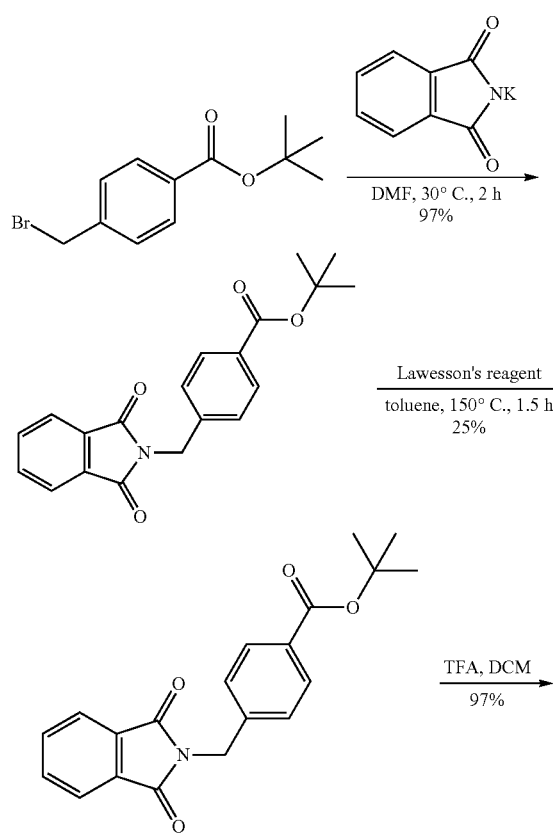
Scheme 5
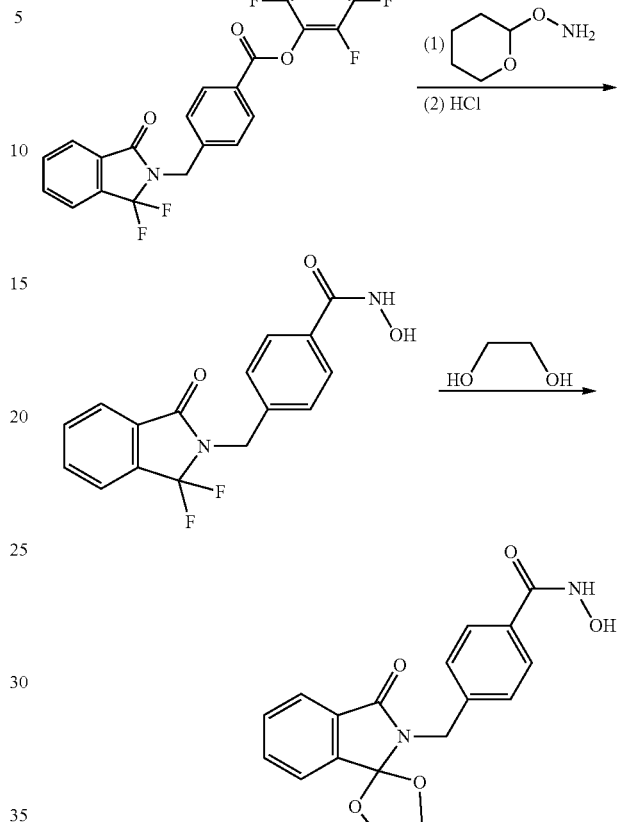
Compound Example 8
Scheme 6
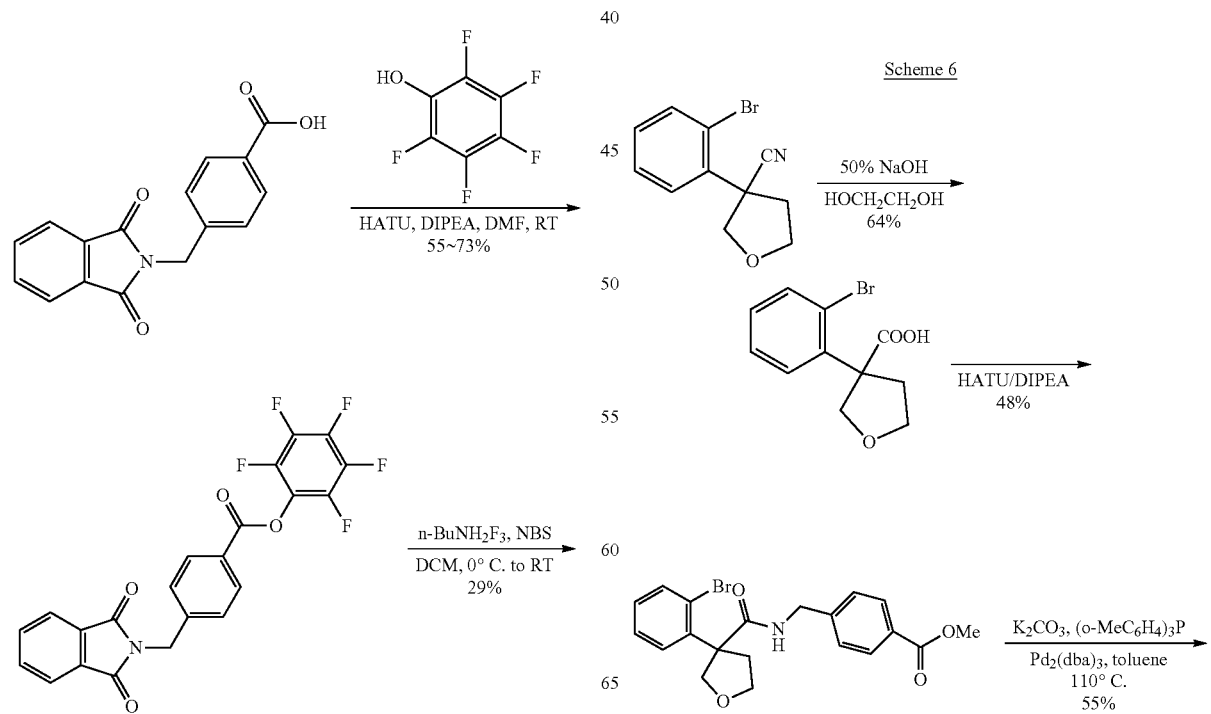

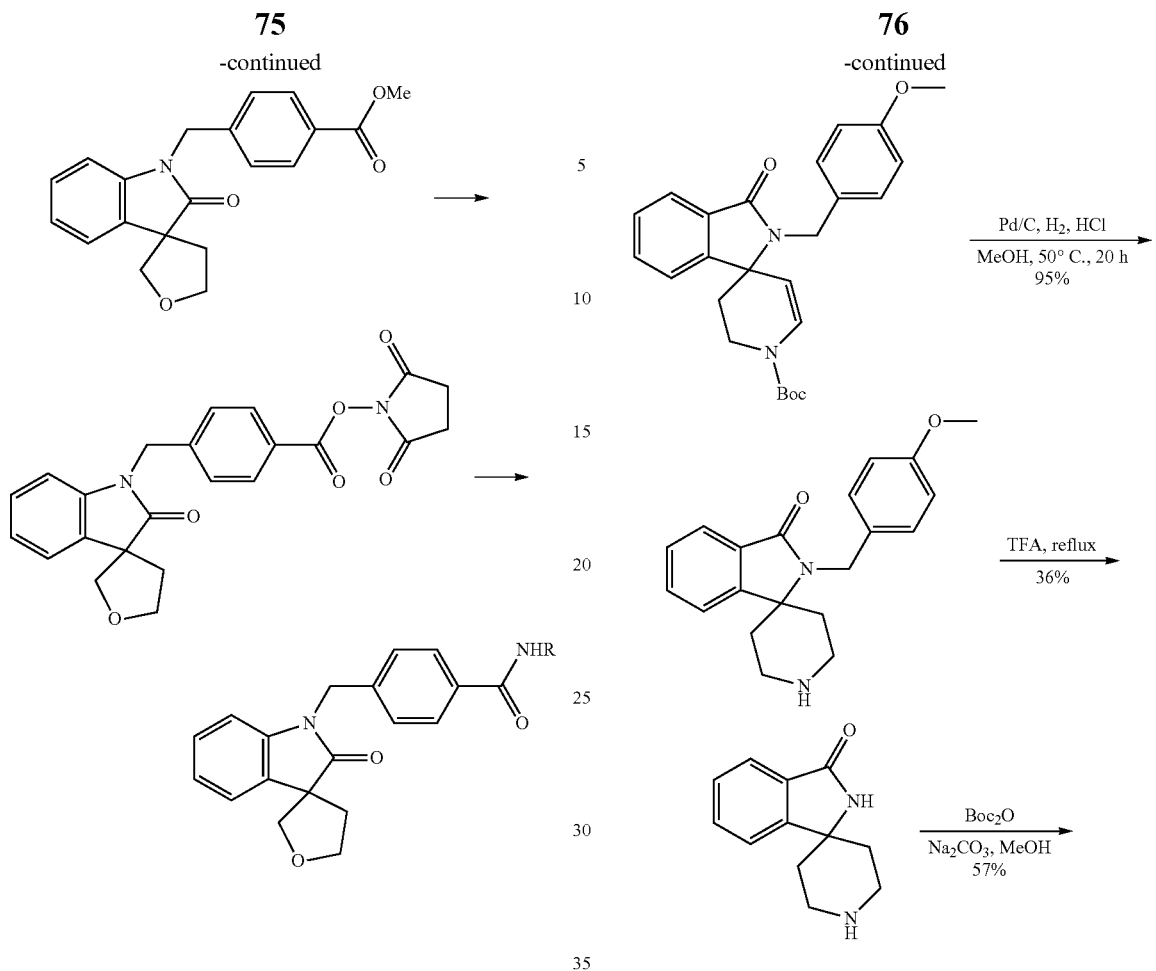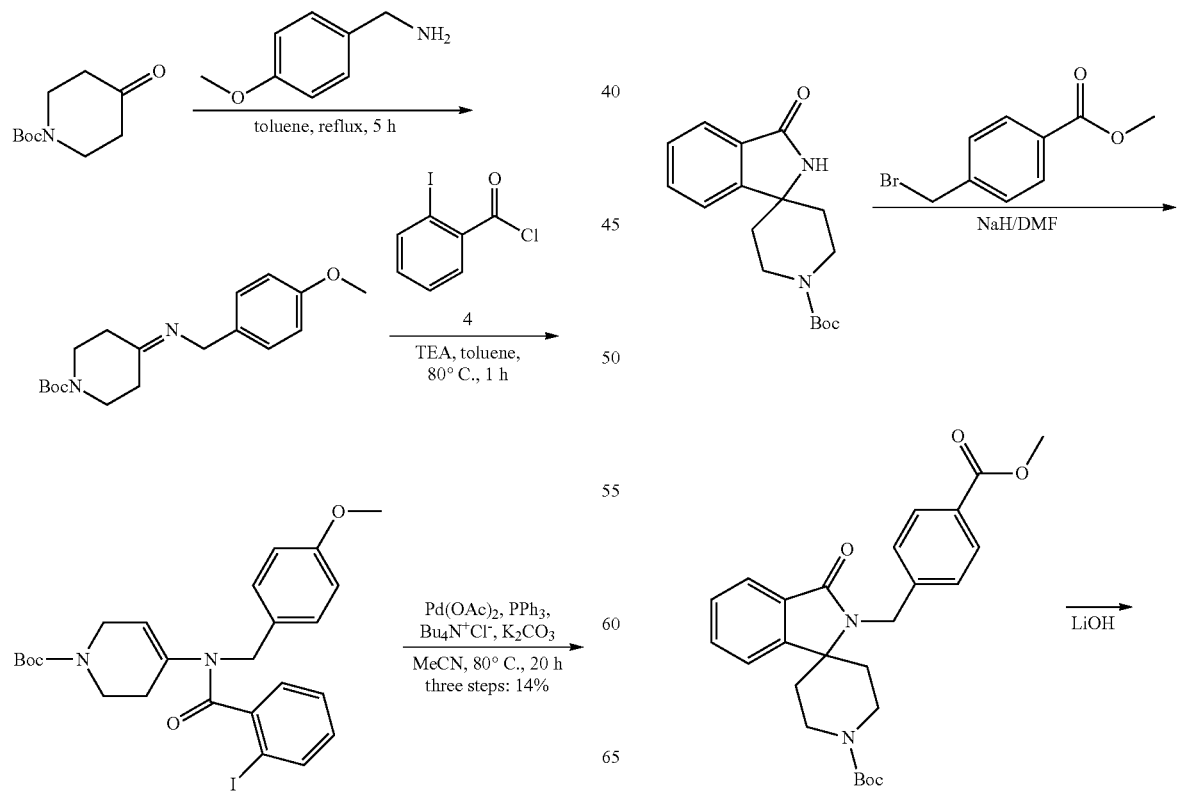

77 78
Scheme 8
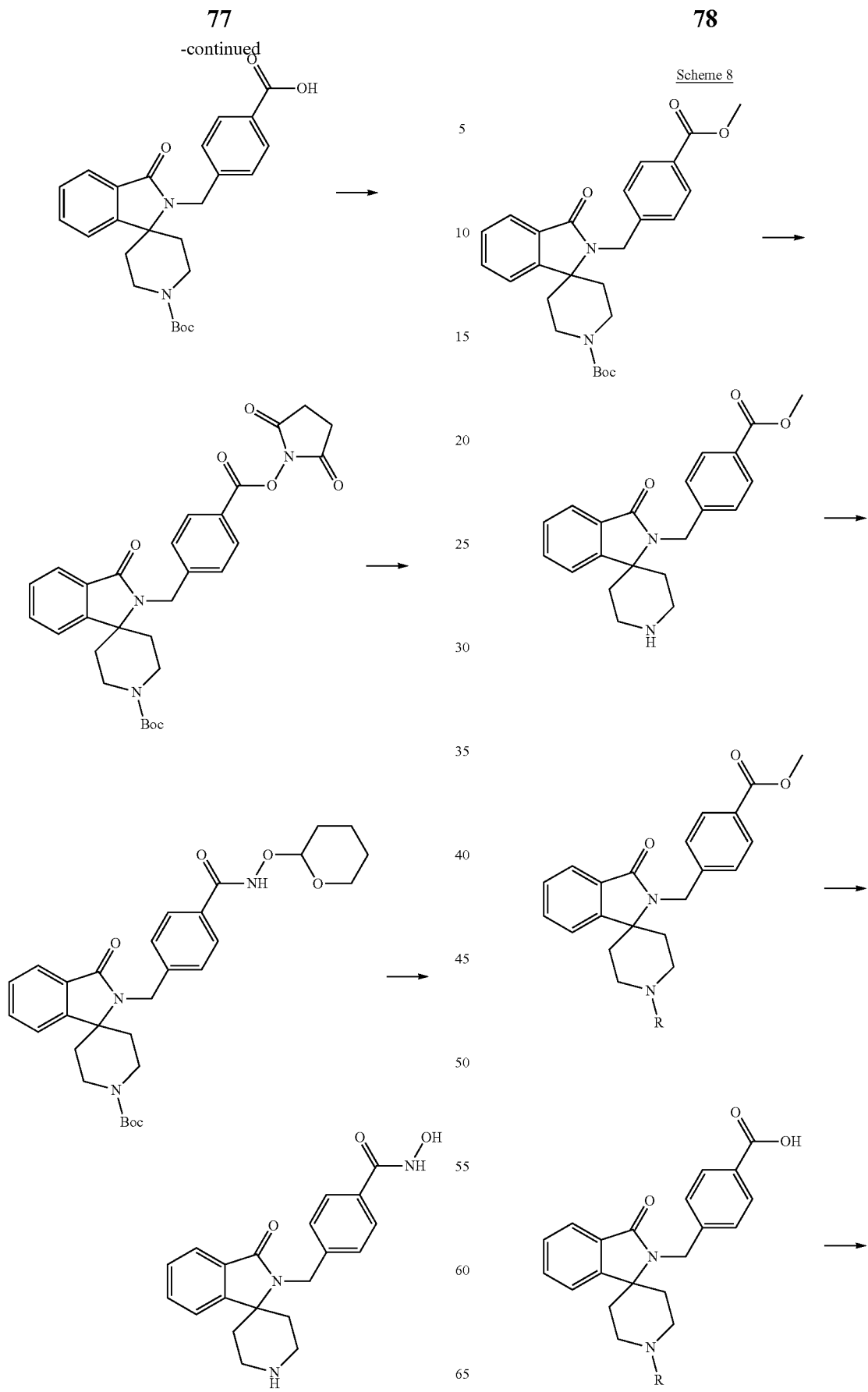

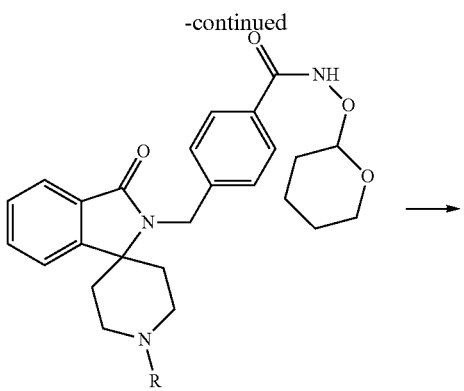

Compound Example 9. N-hydroxy-4-42'-oxo-4,5-dihydro-2H-spiro[furan-3,3'-indolin]-1'-yl)methyl)benzamide

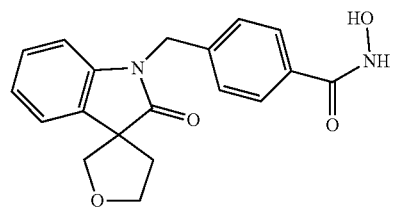 [SMILES: O=C(NO)c1ccc(CN2C(=O)C3(CCOC3)c3ccccc32)cc1]

Compound Example 9 was synthesized according to Scheme 6. ¹H-NMR (400 MHz, DMSO-d6+10% D2O): δ 8.10 (d, J=7.6 Hz, 1H), 7.85 (d, J=7.2 Hz, 1H), 7.65-7.71 (m, 4H), 7.37 (d, J=8.0 Hz, 2H), 4.78 (s, 2H), 3.44 (d, J=8.0 Hz, 4H), 2.39-2.42 (m, 2H), 1.57 (d, J=13.6 Hz, 2H). LC-MS showed a single peak with purity >95% based on UV absorption at 254 nm. MS: $C_{19}H_{18}N_2O_4$. Calculated (M+H): 339, obtained MS: 339.

Compound Example 10. N-hydroxy-4-((3-oxospiro[isoindoline-1,4'-piperidin]-2-yl)methyl)benzamide

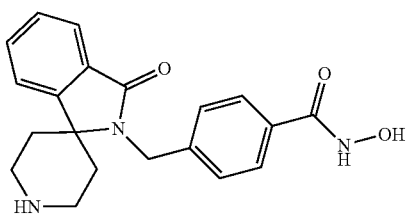 [SMILES: O=C(NO)c1ccc(CN2C(=O)c3ccccc3C23CCNCC3)cc1]

Compound Example 10 was synthesized according to Scheme 7. ¹H-NMR (400 MHz, CDCl3): δ 7.72 (d, J=7.2 Hz, 2H), 7.32-7.37 (m, 3H), 7.18 (t, J=7.2 Hz, 1H), 7.07 (t, J=7.4 Hz, 1H), 6.68 (d, J=7.2 Hz, 1H), 4.96 (s, 1H), 4.25 (t, J=6.4 Hz, 2H), 4.09 (d, J=8.4 Hz, 1H), 3.98 (d, J=8 Hz, 1H), 3.69 (br, 0.5H), 3.11 (br, 0.51H), 2.56-2.62 (m, 1H), 2.18-2.24 (m, 1H), 1.46 (br, 1H). LC-MS showed a single peak with purity >95% based on UV absorption at 254 nm. MS: $C_{20}H_{21}N_3O_3$. Calculated (M+H): 352, obtained MS: 352.

Compound Example 11. 2-(4-(hydroxycarbamoyl)benzyl)-N,N-dimethyl-3-oxospiro[isoindoline-1,4'-piperidine]-1'-carboxamide

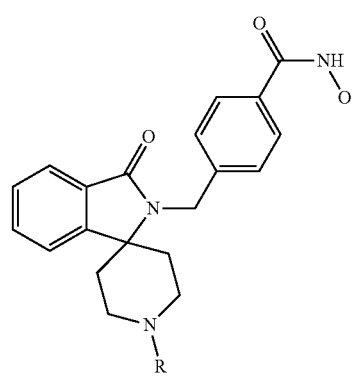

Compound Example 8. N-hydroxy-4-((3-oxospiro[isoindoline-1,2'-[1,3]dioxolan]-2-yl)methyl)benzamide

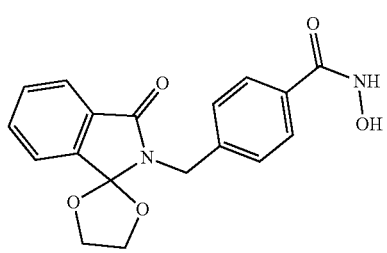

Compound Example 8 was synthesized according to Scheme 5. ¹H-NMR (400 MHz, DMSO-d6+10% D2O): δ 7.72-7.36 (m, 5H), 7.38 (d, J=2.0 Hz, 2H), 4.58 (s, 2H), 4.32-4.22 (m, 4H). LC-MS showed a single peak with purity >95% based on UV absorption at 254 nm. MS: $C_{18}H_{16}N_2O_5$. Calculated (M+H): 341, obtained MS: 341.

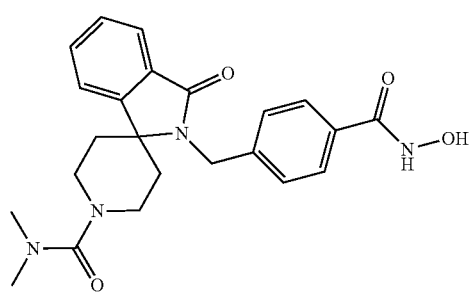 [SMILES: CN(C)C(=O)N1CCC2(CC1)c1ccccc1C(=O)N2Cc1ccc(C(=O)NO)cc1]

Compound Example 11 was synthesized according to Scheme 8. LC-MS showed a single peak with purity >95% based on UV absorption at 254 nm. MS: C23H26N4O4. Calculated (M+H): 423, obtained MS: 423.

Compound Example 12. 4-((1'-cyclopropyl-3-oxospiro[isoindoline-1,4'-piperidin]-2-yl)methyl)-N-hydroxybenzamide

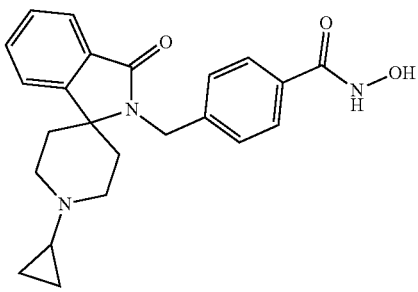 [SMILES: O=C(NO)c1ccc(CN2C(=O)c3ccccc3C23CCN(C2CC2)CC3)cc1]

Compound Example 12 was synthesized according to Scheme 8. LC-MS showed a single peak with purity >95% based on UV absorption at 254 nm. MS: C23H25N3O3. Calculated (M+H): 392, obtained MS: 392.

Compound Example 13. 4-((1'-(cyclopropanecarbonyl)-3-oxospiro[isoindoline-1,4'-piperidin]-2-yl)methyl)-N-hydroxybenzamide

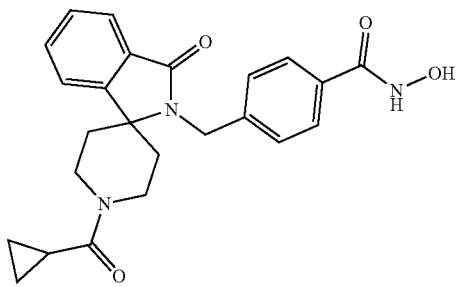 [SMILES: O=C(NO)c1ccc(CN2C(=O)c3ccccc3C23CCN(C(=O)C2CC2)CC3)cc1]

Compound Example 13 was synthesized according to Scheme 8. LC-MS showed a single peak with purity >95% based on UV absorption at 254 nm. MS: C24H25N3O4. Calculated (M+H): 420, obtained MS: 420.

Example 5: Dose Dependent Inhibition of HDAC Compounds Prepared in Enzymatic Assays The results described below demonstrate dose dependent inhibition of HDAC compounds prepared in enzymatic assays, and the IC50 values of synthesized and reference compounds in HDAC Enzymatic Assays. Incubation time for HDAC1/2 is 120 min, and 10 min for other HDACs.
Materials and Methods: Enzymes
Human HDAC1 (GenBank Accession No. NM_004964), full-length with a C-terminal His-tag and a C-terminal FLAG-tag, MW=56 kDa, was expressed in a baculovirus expression system.
Human HDAC2 (GenBank Accession No. NM_001527), full-length with a C-terminal His-tag, MW=56 kDa, was expressed in a baculovirus expression system.
Complex of human HDAC3 (GenBank Accession No. NM_003883), full-length with a C-terminal His tag, MW=49.7 kDa, and human NCOR2 (amino acid 395-489) (GenBank Accession No. NM_006312), N-terminal GST tag, MW=37.6 kDa, was co-expressed in a baculovirus expression system.
Human HDAC4 (GenBank Accession No. NM_006037), amino acids 627-1085 with a N-terminal GST tag, MW=75.2 kDa, was expressed in a baculovirus expression system.
Human HDAC5 (GenBank Accession No. NM_005474), full-length with an N-terminal GST tag, MW=150 kDa, was expressed in a baculovirus expression system.
Recombinant human HDAC6 (GenBank Accession No. BC069243), full-length, MW=180 kDa, was expressed by baculovirus in Sf9 insect cells using an N-terminal GST tag.
Human HDAC7 (GenBank Accession No. AY302468), (a.a. 518-end) with an N-terminal GST tag, MW=78 kDa, was expressed in a baculovirus expression system.
Human HDAC8 (GenBank Accession No. NM_018486), full-length with a C-terminal His tag, MW=46.4 kDa, was expressed in a baculovirus expression system.
Human HDAC9 (GenBank Accession No. NM_178423), amino acids 604-1066 with a C-terminal His tag, MW=50.7 kDa, was expressed in a baculovirus expression system.
Human HDAC10 (a.a. 1-481), GenBank Accession No. NM_032019 with a N-terminal GST tag and a C-terminal His tag, MW=78 kDa, was expressed in a baculovirus expression system.
Human HDAC11 (full length) (GenBank Accession No. NM_024827) with a N-terminal GST tag, MW=66 kDa, was expressed in a baculovirus expression system.
Human SIRT1 (Sirtuin 1, hSir2SIRT1)(GenBank Accession No. NM012238): Full length, MW=82 kDa, expressed in *E. coli.*
Human SIRT2 (Sirtuin 2, hSir2SIRT2)(GenBank Accession No. NM_012237): Full length, MW=43 kDa, expressed in *E. coli.*
Human SIRT3 (Sirtuin 3) (GenBank Accession No. NM_012239): Amino acids 102-399 (catalytically active), MW=32.7 kDa, expressed in *E. coli.*
Human SIRT5 (Sirtuin 5) (GenBank Accession No. NM_012241 (isoform 1); residues 37-310, MW=32.3 kDa) expressed in *E. coli* with an N-terminal His-tag).
The substrate RHKKAc-AMC, RHKAcKAc-AMC and AcK(trifluoroacetyl)-AMC were synthesized by Biomer.
ACY-1215, SAHA, Tubastatin A and Trichostatin A (TSA) was purchased from Selleckchem. TMP269 was purchased from MedKoo Biosciences. Nicotinamide adenine dinucleotide (NAD) was purchased from Tocris.
Materials and Methods: Biochemical Assay Procedure
I. Compound handling: Testing compounds were dissolved in 100% DMSO to a specific concentration. The serial dilution was conducted by epMotion 5070 in DMSO.
II. HDAC reaction buffer: 50 mM Tris-HCl, pH8.0, 137 mM NaCl, 2.7 mM KCl, and 1 mM MgCl2, Added fresh: 1 mg/ml BSA, 1% DMSO.
III. Substrate: Fluorogenic HDAC General Substrate for HDAC1, 2, 3, 6, 10, 11 ans Sirt1, 2 and 3: Arg-His-Lys-Lys(Ac); HDAC8 only substrate: Arg-His-Lys (Ac)-Lys(Ac); Class2A Substrate (HDAC4, 5, 7 and 9): Acetyl-Lys(trifluoroacetyl)-AMC; Sirt5 substrate: Ac-Lys(succinyl)-AMC.

IV. General Reaction Procedure: (Standard IC50 determination)
   a. Delivered 2× enzyme in wells of reaction plate except No Enzyme (No En) control wells. Add buffer in No En wells.
   b. Delivered compounds in 100% DMSO into the enzyme mixture by Acoustic technology (Echo550; nanoliter range). Spin down and pre-incubation.
   c. Delivered 2× Substrate Mixture (Fluorogenic HDAC Substrate and co-factor (500 mM of Nicotinamide adenine dinucleotide ($NAD^+$) in all Sirt assay) in all reaction wells to initiate the reaction. Spin and shake.
   d. Incubated for 1-2 hr. at 30° C. with seal.
   e. Added Developer with Trichostatin A (or TMP269 or $NAD^+$) to stop the reaction and to generate fluorescent color.
   f. Fluorescence was read (excitatory, 360; emission, 460) using the EnVision Multilabel Plate Reader (Perkin Elmer)
   g. Endpoint reading was taken for analysis after the development reaches plateau.
V. Data Analysis: The percentages of enzyme activity (relative to DMSO controls) and IC50 values were calculated using the GraphPad Prism 4 program based on a sigmoidal dose-response equation.

The inhibitory activities of HDAC compounds were determined using biochemical HDAC assays and data are summarized in Table 2. Compounds with indicated doses were tested in the biochemical assays of HDAC1, HDAC2, HDAC3, HDAC4, HDAC5, HDAC6, HDAC7, HDAC8, HDAC9, HDAC10, or HDAC11 enzyme. The curve fit and IC50 values were calculated using the GraphPad Prism 4 program based on a sigmoidal dose-response equation.

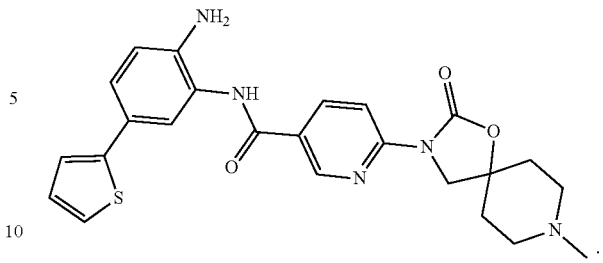

Materials and Methods.

Compound Example 4 mouse plasma PK:
  Dose: 1 mg/kg intravenous (IV) and 7 mg/kg oral dosage (PO)
  Formulation: 0.1 mg/mL IV and 1 mg/mL PO solution in 10/10/80 DMSO/Tween80/Water
  Mice Info: Male C57 Bl/6J Results.

Plasma PK were evaluated in mice after administration of Compound Example 4. Following IV administration, the PK properties show a good half-life ($T_{1/2}$) of 1.2 h, high AUC (~7.3 µM·h), low clearance, and low volume (Table 3). The properties are also fair by oral dosing, with good half-life (1.9 h) and AUC (area under curve) (~16 µM·h), and a reasonable bioavailability (% F) of 31% (Table 4). Maximal half-life ($T_{max}$), maximal concentration ($C_{max}$), observed clearance (Cl_obs), mean residential time (MRT), and volume of distribution (Vss_obs) were also quantified (Tables 3 and 4).

TABLE 2

Biochemical HDAC assay data for selected compounds of Formula I-A and I-B.

| Compound Example | HDAC1 (µM) | HDAC2 (µM) | HDAC3 (µM) | HDAC4 (µM) | HDAC5 (µM) | HDAC6 (µM) | HDAC7 (µM) | HDAC8 (µM) | HDAC9 (µM) | HDAC10 (µM) | HDAC11 (µM) |
|---|---|---|---|---|---|---|---|---|---|---|---|
| 8 | 8.0 | >10 | >10 | | | 0.029 | | 0.40 | | | |
| 9 | 9.1 | 17.2 | 21 | | | 0.0045 | | 1.92 | | | |
| 10 | 6.0 | >10 | 7.0 | | | 0.205 | | 0.710 | | | |
| 11 | >10 | >10 | >10 | 5.0 | 1.55 | 0.035 | 0.85 | 0.52 | 3.2 | >10 | 4.1 |
| 12 | >10 | >10 | 9.26 | >10 | >10 | 0.026 | 3.1 | 1.2 | 6.9 | >10 | 3.6 |

Figure 2:
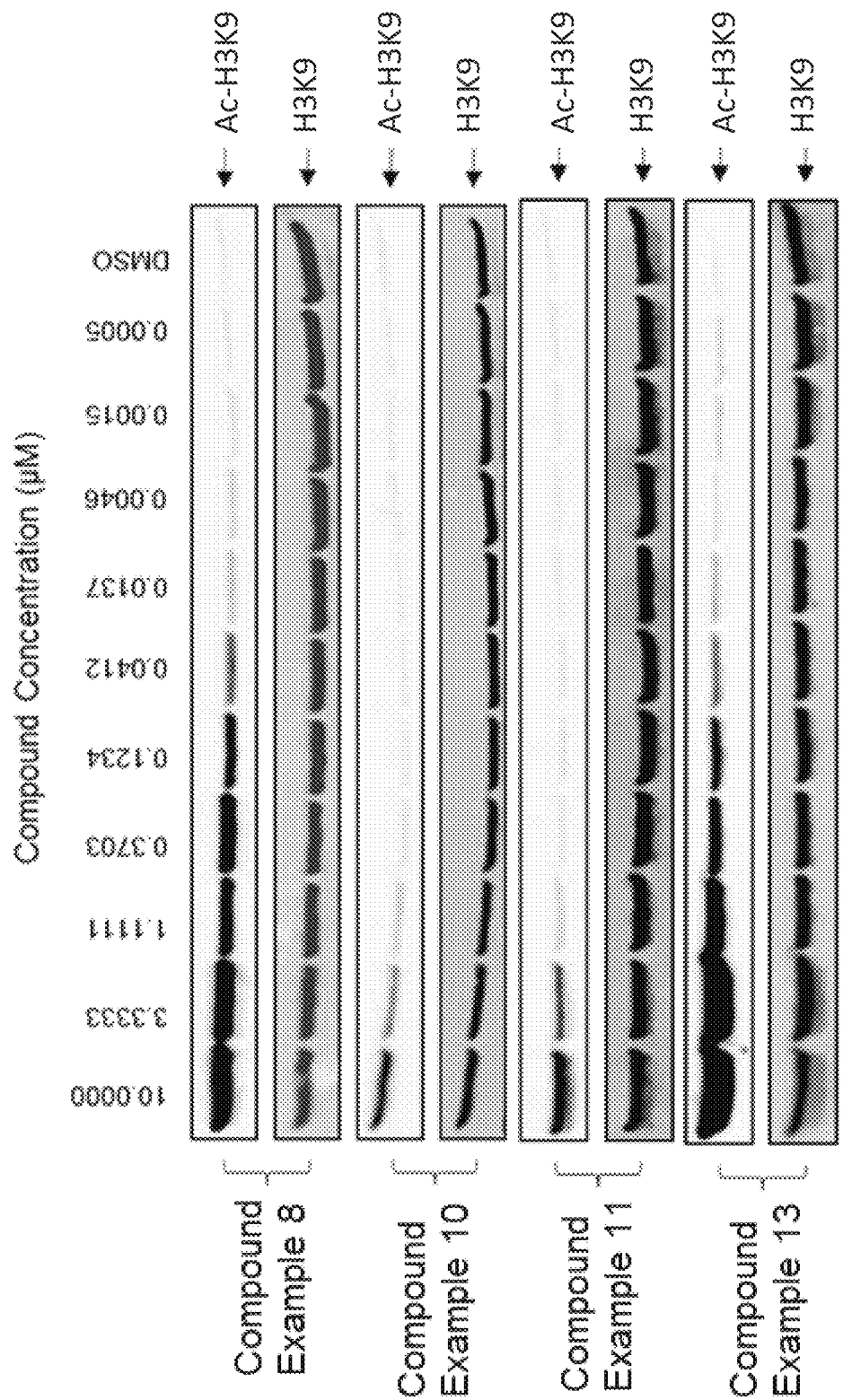
FIG. 2 depicts a Western blot of Compound Example 8, Compound Example 10, Compound Example 11, and Compound Example 13.

Example 6: Modulation of a-Tubulin Acetylation by Some of Inhibitors in PC-3 Cells PC-3 cells were treated with the indicated concentrations of Compound Examples 8, 10, 11, and 13 for 24 hours as depicted in FIG. 2. The whole cell lysates were subjected to Western blot analyses with anti-Acetylated-tubulin antibody (FIG. 2). The blots were then re-probed with anti-alpha-tubulin antibody.

Example 7: In Vivo Pharmacokinetics Studies of N-(2-amino-5-(thiophen-2-yl)phenyl)-6-(8-methyl-2-oxo-1-oxa-3,8-diazaspiro[4.5]decan-3-yl)nicotinamide in Mice In vivo PK (pharmacokinetics) studies were run at Scripps Florida DMPK Core facility. Mouse plasma PK data was obtained using Compound Example 4 (N-(2-amino-5-(thiophen-2-yl)phenyl)-6-(8-methyl-2-oxo-1-oxa-3,8-diazaspiro[4.5]decan-3-yl)nicotinamide)

TABLE 3

Mouse plasma PK data after IV administration of Compound Example 4.

| | Mouse-1 | Mouse-2 | Mouse-3 | Average |
|---|---|---|---|---|
| $T_{1/2}$ (hr) | 0.86 | 1.33 | 1.28 | 1.16 |
| $T_{max}$ (hr) | 0.08 | 0.08 | 0.08 | 0.08 |
| $C_{max}$ (ng/mL) | 1560 | 2490 | 2040 | 2030 |
| $C_{max}$ (µM) | 3.37 | 5.38 | 4.41 | 4.38 |
| $AUC_{last}$ (min*ng/mL) | 212187 | 175879 | 219951 | 202672 |
| AUC last (µM.hr) | 7.64 | 6.33 | 7.92 | 7.30 |
| $AUC_{INF\_obs}$ (min*ng/mL) | 212819 | 177722 | 224191 | 204911 |
| AUC (% Extrap) | 0.30 | 1.04 | 1.89 | 1.08 |
| Cl_obs (mL/min/kg) | 4.70 | 5.63 | 4.46 | 4.93 |

TABLE 3-continued

Mouse plasma PK data after IV administration of Compound Example 4.

|  | Mouse-1 | Mouse-2 | Mouse-3 | Average |
|---|---|---|---|---|
| $MRT_{INF\_obs}$ (hr) | 1.76 | 1.74 | 1.97 | 1.82 |
| Vss_obs (L/kg) | 0.50 | 0.59 | 0.53 | 0.54 |

TABLE 4

Mouse plasma PK data after oral administration of Compound Example 4.

|  | Mouse-1 | Mouse-2 | Mouse-3 | Average |
|---|---|---|---|---|
| $T_{1/2}$ (hr) | 1.65 | 2.25 | 1.78 | 1.90 |
| $T_{max}$ (hr) | 1.00 | 1.00 | 1.00 | 1.00 |
| $C_{max}$ (ng/mL) | 3200 | 1930 | 2350 | 2493 |
| $C_{max}$ (µM) | 6.91 | 4.17 | 5.08 | 5.39 |
| $AUC_{last}$ (min*ng/mL) | 654948 | 303573 | 369340 | 442620 |
| $AUC_{last}$ (µM.hr) | 23.58 | 10.93 | 13.30 | 15.93 |
| $AUC_{INF\_obs}$ (min*ng/mL) | 690882 | 335315 | 388640 | 471613 |
| AUC (% Extrap) | 5.20 | 9.47 | 4.97 | 6.54 |
| Cl_obs (mL/min/kg) | 10.13 | 20.88 | 18.01 | 16.34 |
| % F | N/A | N/A | N/A | 31% |

Example 8: Brain Exposure Experiments Using N-(2-amino-5-(thiophen-2-yl)phenyl)-6-(8-methyl-2-oxo-1-oxa-3,8-diazaspiro[4.5]decan-3-yl)nicotinamide (Compound Example 4)

Brain exposure experiments were performed wherein mice were exposed to Compound Example 4 at an IV dosage of 1 mg/kg (Table 5). The results showed that Compound Example 4 expressed very low brain penetration 1 hour after exposure.

TABLE 5

Brain exposure experiments of Compound Example 4 in mice

| Mouse # | Plasma (ng/mL) | µM | Brain (ng/mL) | µM |
|---|---|---|---|---|
| 7 | 1660 | 3.59 | 61.9 | 0.13 |
| 8 | 1030 | 2.22 | 0 | 0.00 |
| 9 | 1620 | 3.50 | 73 | 0.16 |
| Average | 1436.7 | 3.10 | 67.5 | 0.15 |

Example 9: Determination of the Efficacy of Y-5Fa and Compound Example 4 in the HCT-116 Xenograft Model Using Female CD-1 Nude Mice IX.a Animal model background. A mouse HCT-116 xenograft tumor model was used to evaluate the efficacy of Compound Example 4.

IX.b Animal testing details.
  III.b1 Animal
    A. Species: Mouse
    B. Strain: CD-1 nude
    C. Source: Charles River Laboratories
    D. Age at Initiation of Treatment: Approximately 6 to 7 weeks of age
    E. Weight at Initiation of Treatment: Approximately 15 to 20 grams.
    F. Number and Sex: 40 females for each compound.
    G. Identification: Individual caged identified by cage card.
    H. Acclimation: For at least three days.
    I. Randomization: Based on tumor volume. Only healthy animals are included.
  IX.b2 Husbandry
    A. Housing: Animals are housed of two per cage in plastic boxes.
    B. Diet: Certified Rodent Diet #5002 (LabDiet) ad libitum, unless otherwise specified.
    C. Water: Ad libitum.
    D. Contaminants: There are no known contaminants in the diet or water at levels that might interfere with this study.
    E. Environment: Environmental controls for the animal room are set to maintain 18 to 26° C., a relative humidity of 30 to 70%, a minimum of 10 air changes/hour, and a 12-hour light/12-hour dark cycle.
  IX.b3 Vehicle articles
    A. Identification: 40% PEG-400 (v/v), 25% HPβCD (w/v) and 35% Purified Water
    B. Lot Numbers: The lot numbers are maintained in the raw data.
    C. Purity: The lot number are recorded as provided by the manufacturer.
    D. Stability: The expiration date provided by the manufacturer is recorded.
    E. Storage Conditions: Are provided by the manufacturer.
    F. Characteristics: Information on synthesis methods, composition, or other characteristics that define the control article is on file with the manufacturer.
  IX.b4 Experimental design and procedures
    A. Preparation of mouse cancer cell lines.
    HCT-116 cell lines are cultured and prepared according to the ATCC product sheet.
    B. Establishment of Tumors.
      1. 80 female CD-1 nude mice (6-7 weeks).
      2. Implantation: Cancer cells are injected subcutaneously into right flank. For HCT-116 cells: 5×10E6 cells in 50λ PBS and 50λ Matrigel in each female CD-1 nude mice.
      3. Staging: Once tumors reach approximately 50 mm³ in volume (measured with digital caliper), mice are randomized into 7 treatment groups of at least 10 mice per group based on their tumor volumes. The calculation of tumor volume uses the formula: W×W×L/2.
    C. Treatment Regimen.
      1. Tumor measurements are recorded three times on Monday, Wednesday and Friday each week.
      2. Mouse body weight is recorded once on Monday each week.
      3. Daily dose is given by oral gavage, including weekends.
      4. The dose is adjusted according to the body weight measurement.

D. Study Group and Dose Levels (Table 5):

TABLE 5

Mice study groups and dosages.

| Group | Animal ID | Establishment of Tumors | Treatment (oral gavage, 10 mL/kg) |
|---|---|---|---|
| 1 | 1 to 10 | For 40 mice: (s.c injection) 5x10E6 HCT-116 cells in 50 μL PBS and 50 μL Matrigel Mice are randomized and divided into four groups: 10 mice/group | Vehicle |
| 2 | 41 to 50 | | Compound Example 4 50 mL/kg |
| 3 | 51 to 60 | | Compound Example 4 100 mL/kg |
| 4 | 61 to 70 | | Compound Example 4 200 mL/kg |

E. Monitoring.
1. Record signs of distress daily.
2. Record mouse body weights as described above.
3. Record tumor measurements as described above.
F. Measurements.
1. Measurements of tumor sizes are continued to the end of this study.
2. Mice are sacrificed at completion of dosing regimen or mice are sacrificed when tumor size is more than 2000 mm$^3$.
G. Data Collection. At the end of the three-week dosing period, mice are sacrificed, blood, and tumors collected.
IX.b5 Tissue sample collections A. Blood/plasma collection: On Day 7, blood samples are collected from first 3 animals in each group at 90 minutes after dosing and approximately 50 μL of plasma is obtained and frozen over dry ice.

At the end of the three-week dosing period, blood samples are collected from second 3 animals in each group at 90 minutes after dosing and at minimum 100 uL of plasma is obtained and frozen over dry ice.

Figure 3:
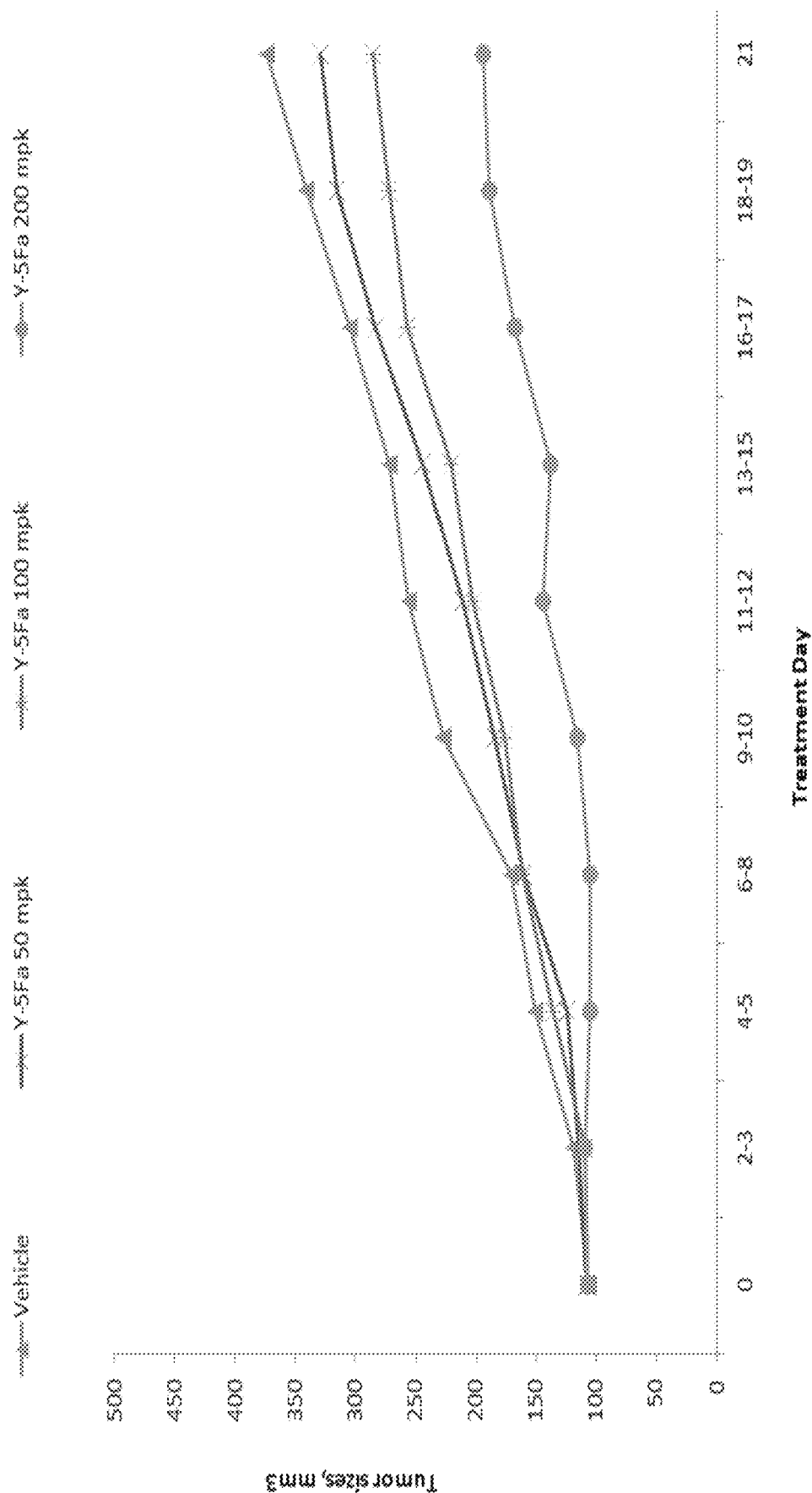
FIG. 3 depicts in vivo efficacy studies of Compound Example 4 in a Y-5Fa xenograft mouse model.

B. Tumor collection: The entire tumor is removed, weighed, and recorded. Around 200 mg of tumor from 3 animals in each group are cut, weighed, and frozen over dry ice for PK analysis.
IX.c In vivo efficacy testing results The efficacy of treating tumors with 50 mg/kg, 100 mg/kg, and 200 mg/kg dosages of Compound Example 4 was studied and results are shown in FIG. 3.

The disclosures of each and every patent, patent application, and publication cited herein are hereby incorporated herein by reference in their entirety. While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:
1. A compound of Formula I, or a salt or solvate thereof:

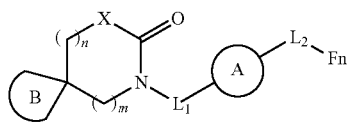

Formula I wherein in Formula I:
Ring A is an aromatic ring having 0-2 ring nitrogen atoms;
Ring B is a 3-7 membered saturated or unsaturated carbocyclic ring, or a 3-7 membered saturated or unsaturated heterocyclic ring having 1-3 ring atoms of O, S, SO, SO$_2$, or NR$^a$, and wherein Ring B may optionally be substituted by one or more R$^b$s;
L$_1$ is a bond or a C$_1$-C$_3$ alkyl group optionally substituted by R$^b$;
L$_2$ is a bond, a C$_1$-C$_3$ alkyl group optionally substituted by R$^b$, an alkenyl, or an alkynyl;
X is CH$_2$, O, or NR$^c$;
each R$^a$ is independently selected from the group consisting of H, F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, and wherein each R$^d$, R$^e$ and R$^f$ is independently selected from the group consisting of H, and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of R$^d$, R$^e$ or R$^f$ may be optionally joined to form additional rings;
each R$^b$ is independently selected from the group consisting of H, F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, NO$_2$, OR$^d$, OC(=O)R$^d$, OC(=O)OR$^d$, OC(=O)NR$^d$R$^e$, CR$^d$R$^e$R$^f$, CR$^d$R$^e$OR$^f$, C(=O)R$^d$, C(=O)NR$^d$R$^e$, C(=O)OR$^d$, NR$^d$R$^e$, NR$^d$C(=O)R$^e$, NR$^d$C(=O)OR$^e$, NR$^d$C(=O)NR$^e$R$^f$, NR$^d$S(=O)$_2$R$^e$, NR$^d$S(=O)$_2$NR$^e$R$^f$, SR$^d$, S(=O)R$^d$, S(=O)$_2$R$^d$, and S(=O)$_2$NR$^d$R$^e$, and wherein each R$^d$, R$^e$ and R$^f$ is independently selected from the group consisting of H, and optionally substituted C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ may be optionally joined to form additional rings;

wherein any $R^a$ and $R^b$ may be optionally joined to form additional rings;

$R^c$ is selected from the group consisting of H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ may be optionally joined to form additional rings;

Fn is selected from the group consisting of Formulae II, III, IV and V:

Formula II

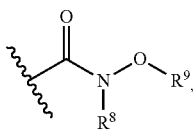

Formula III

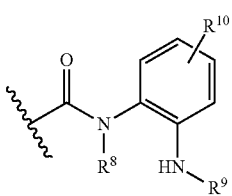

Formula IV

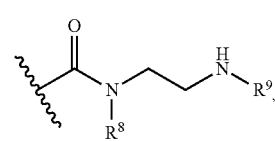

Formula V

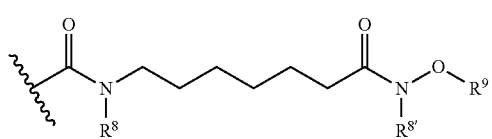

wherein in Formulae II, III, IV and V:

$R^8$, $R^{8'}$, and $R^{10}$ are each independently selected from the group consisting of H, halogen, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl may optionally be substituted, and $R^{10}$ can represent single, multiple, or no substitution;

$R^9$ is selected from the group consisting of H, halogen, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein the $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, heterocycloalkylalkyl may optionally be substituted;

m is an integer from 0-3; and n is an integer from 0-3.

2. The compound of claim 1, wherein the compound is selected from the group consisting of

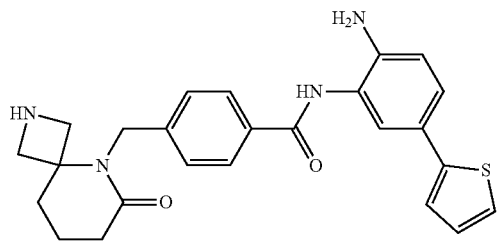

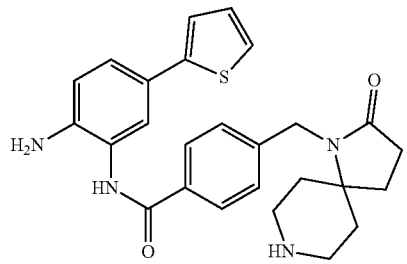

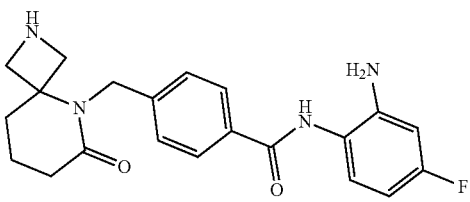

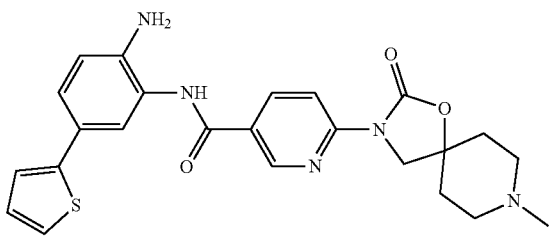

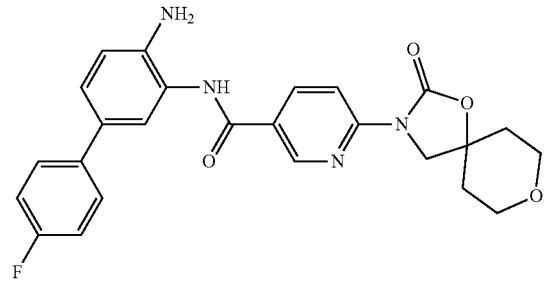

91
-continued
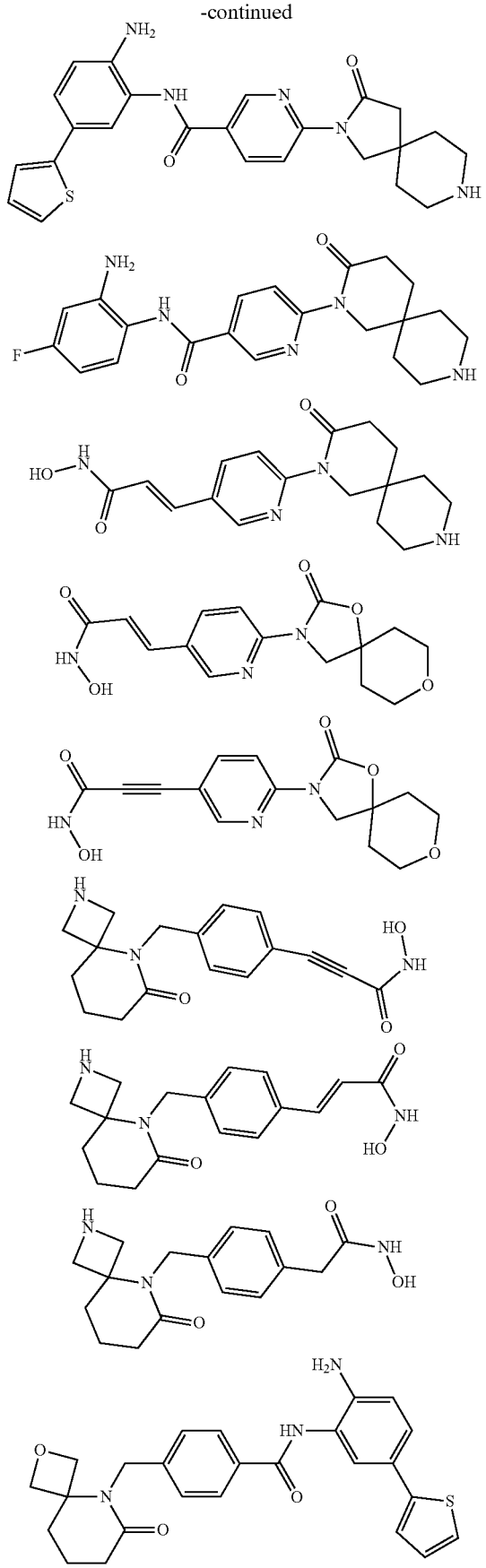
92
-continued
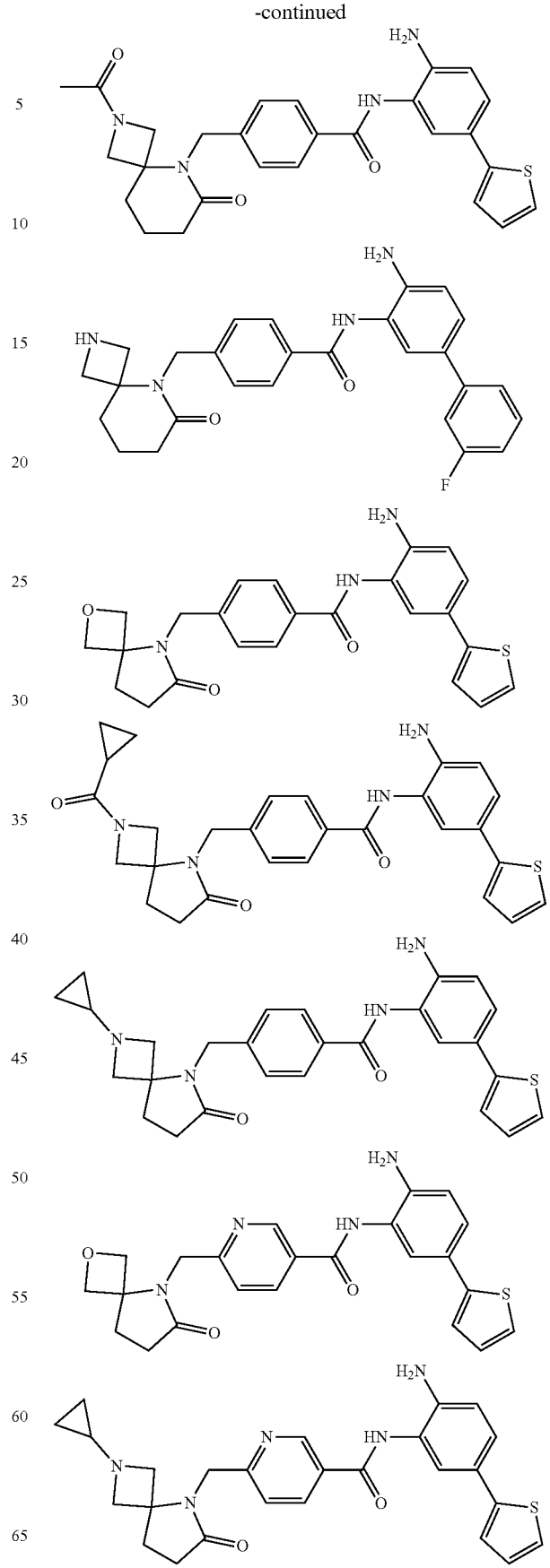

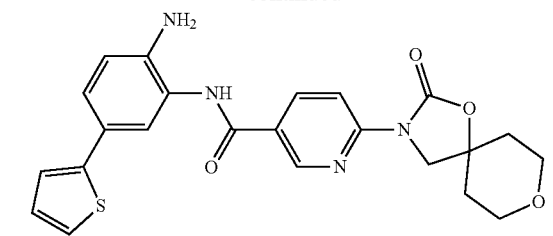
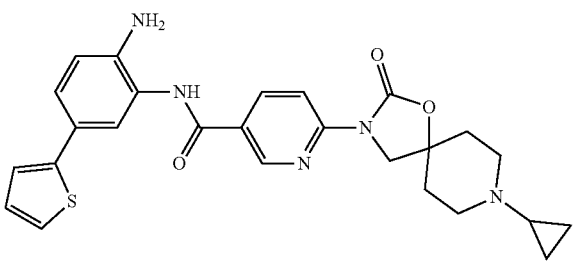
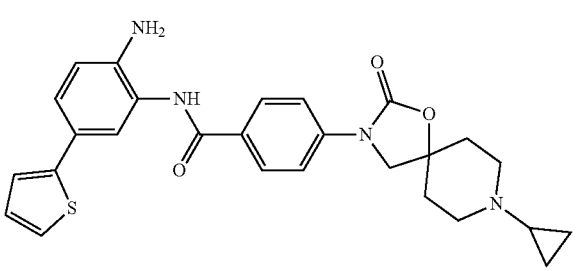
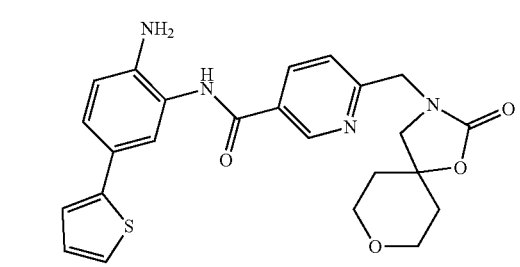
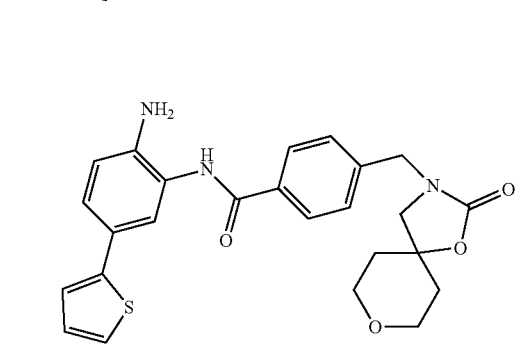
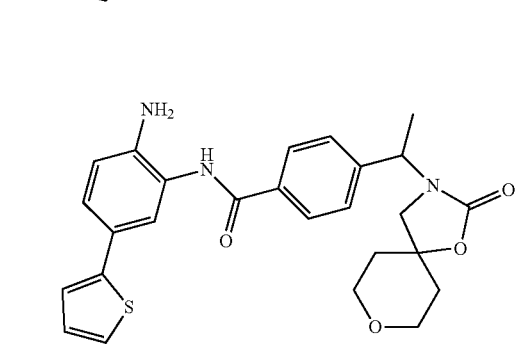

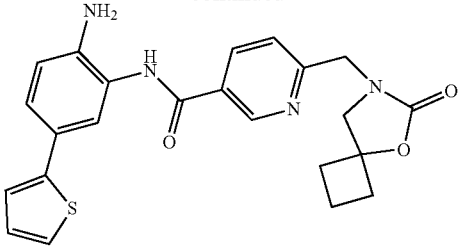
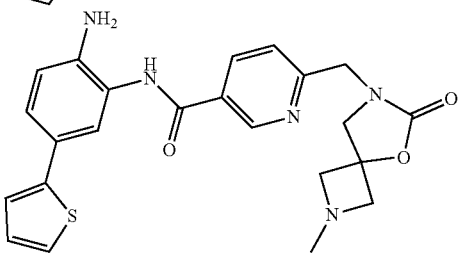
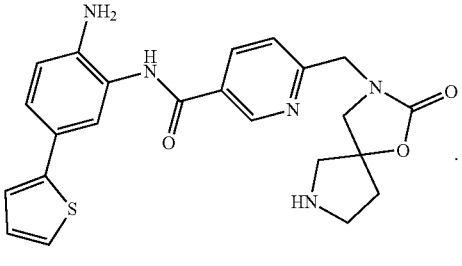

3. A compound of Formula I-A, or a salt or solvate thereof:

Formula I-A

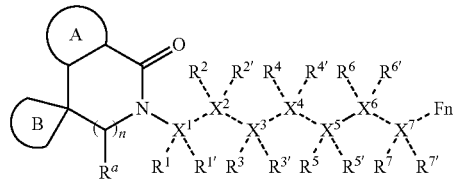

wherein in Formula I-A:
Ring A is an aromatic ring having 0-3 ring nitrogen atoms, and wherein Ring A may optionally be substituted by one or more $R^b$s;
Ring B is a saturated or unsaturated 3-7 membered carbocyclic ring or a saturated or unsaturated 3-7 membered heterocyclic ring having 1-3 ring atoms of O, S, SO, $SO_2$, or $NR^b$, and wherein Ring B may optionally be substituted by one or more $R^c$s;
$R^a$, $R^b$ and $R^c$ are each independently selected from the group consisting of H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NRdS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ can optionally be joined to form additional rings; and $R^a$, $R^b$ and $R^c$ can optionally be joined to form additional rings;

chain

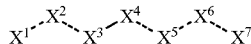

is an uninterrupted chain, wherein any bond can be a single, double or triple bond, consistent with the hybridization state of the connected atoms, and wherein a null selection for any of the $X^1$ to $X^7$ nodes results in a null selection for the adjacent R groups;

$X^1$, $X^2$, $X^3$, $X^4$, $X^5$, $X^6$, and $X^7$ are each independently selected from the group consisting of null, C, CH, $CH_2$, $C(=O)$, O, N, NH, S, $S(=O)$ and $S(=O)_2$;

$R^1$, $R^{1'}$, $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$ are each independently selected from the group consisting of null, H, F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is optionally substituted by 1, 2, 3, 4, or 5 substituents independently selected from F, Cl, Br, I, CN, $NO_2$, $OR^d$, $OC(=O)R^d$, $OC(=O)OR^d$, $OC(=O)NR^dR^e$, $CR^dR^eR^f$, $CR^dR^eOR^f$, $C(=O)R^d$, $C(=O)NR^dR^e$, $C(=O)OR^d$, $NR^dR^e$, $NR^dC(=O)R^e$, $NR^dC(=O)OR^e$, $NR^dC(=O)NR^eR^f$, $NR^dS(=O)_2R^e$, $NR^dS(=O)_2NR^eR^f$, $SR^d$, $S(=O)R^d$, $S(=O)_2R^d$, and $S(=O)_2NR^dR^e$, and wherein $R^d$, $R^e$ and $R^f$ are each independently selected from the group consisting of H, and optionally substituted $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and wherein any of $R^d$, $R^e$ or $R^f$ can optionally be joined to form additional rings; and any of R', $R^{1'}$, $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$ can optionally be connected to each other to form various carbocyclic or heterocyclic systems; and Fn is selected from the group consisting of Formulae II, III, IV and V:

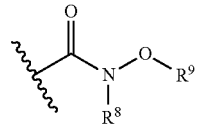
Formula II

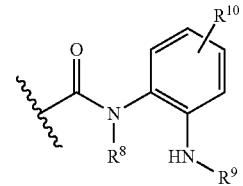
Formula III

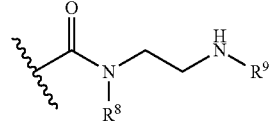
Formula IV

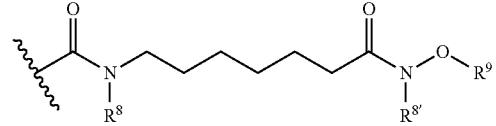
Formula V wherein in Formulae II, III, IV and V:

$R^8$, $R^{8'}$, $R^9$, and $R^{10}$ are each independently selected from the group consisting of null, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, and $R^{10}$ can represent single, multiple, or no substitution;

n is an integer of 0-3.

4. A kit for inhibiting an HDAC or for treating a disease or disorder associated with an HDAC in a subject, comprising an amount of a compound of claim 1, or a salt or solvate thereof, and an instruction manual for the use thereof.

5. A probe for imaging, diagnosing, or theragnosting a disease or disorder associated with an HDAC in a subject, comprising a compound of claim 1, or a salt or solvate thereof.

6. A kit for inhibiting an HDAC or for treating a disease or disorder associated with an HDAC in a subject, comprising an amount of a compound of claim 3, or a salt or solvate thereof, and an instruction manual for the use thereof.

7. A probe for imaging, diagnosing, or theragnosting a disease or disorder associated with an HDAC in a subject, comprising a compound of claim 3, or a salt or solvate thereof.

* * * * *